United States Patent
Ono et al.

(10) Patent No.: US 10,135,002 B2
(45) Date of Patent: Nov. 20, 2018

(54) ORGANIC ELECTROLUMINESCENT ELEMENT, AND LIGHTING DEVICE AND DISPLAY DEVICE WHICH ARE PROVIDED WITH SAME

(71) Applicant: Konica Minolta, Inc., Tokyo (JP)

(72) Inventors: Kaori Ono, Ichihara (JP); Norio Miura, Sagamihara (JP); Takamune Hattori, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 400 days.

(21) Appl. No.: 14/780,865

(22) PCT Filed: Mar. 28, 2014

(86) PCT No.: PCT/JP2014/059118
§ 371 (c)(1),
(2) Date: Sep. 28, 2015

(87) PCT Pub. No.: WO2014/157618
PCT Pub. Date: Oct. 2, 2014

(65) Prior Publication Data
US 2016/0056392 A1 Feb. 25, 2016

(30) Foreign Application Priority Data
Mar. 29, 2013 (JP) ................. 2013-072081

(51) Int. Cl.
*H01L 51/00* (2006.01)
*H01L 51/50* (2006.01)
(Continued)

(52) U.S. Cl.
CPC ........ *H01L 51/0072* (2013.01); *C07D 409/14* (2013.01); *C07F 9/65583* (2013.01);
(Continued)

(58) Field of Classification Search
CPC ............... C07D 409/14; C07F 9/65583; C07F 9/65586; C07F 9/65613; C09K 11/025;
(Continued)

(56) References Cited

U.S. PATENT DOCUMENTS

| 6,097,147 A | 8/2000 | Baldo et al. |
| 2012/0298966 A1 | 11/2012 | Zeng et al. |

(Continued)

FOREIGN PATENT DOCUMENTS

| JP | 2005112765 A | 4/2005 |
| JP | 2012049518 A | 3/2012 |

(Continued)

OTHER PUBLICATIONS

Machine translation for KR 10-2012-0020901 A (Publication date: Mar. 2012).*
(Continued)

*Primary Examiner* — Dawn L Garrett
(74) *Attorney, Agent, or Firm* — Lucas & Mercanti, LLP

(57) ABSTRACT

One objective of the present invention is to provide an organic EL element which is suppressed in change in the resistance of a light emitting layer after passing a current therethrough for a long period of time, thereby having good emission spectrum chromaticity, and which is suppressed in change in the emission characteristics over time. Another objective of the present invention is to provide a lighting device and a display device, each of which uses the organic EL element. An organic electroluminescent element of the present invention is provided with a pair of electrodes and one or more organic layers that are arranged between the pair of electrodes, and is characterized in that one or more layers among the organic layers contain a compound that has a structure represented by general formula (1).

11 Claims, 7 Drawing Sheets

(51) Int. Cl.
  *C07F 9/6558* (2006.01)
  *C07F 9/6561* (2006.01)
  *C09K 11/06* (2006.01)
  *H05B 33/14* (2006.01)
  *C07D 409/14* (2006.01)
  *C09K 11/02* (2006.01)

(52) U.S. Cl.
  CPC ...... *C07F 9/65586* (2013.01); *C07F 9/65613* (2013.01); *C09K 11/025* (2013.01); *C09K 11/06* (2013.01); *H01L 51/0073* (2013.01); *H01L 51/0085* (2013.01); *H01L 51/0087* (2013.01); *H01L 51/0094* (2013.01); *H01L 51/5016* (2013.01); *H05B 33/14* (2013.01); *C09K 2211/1029* (2013.01); *C09K 2211/185* (2013.01)

(58) Field of Classification Search
  CPC ............ C09K 11/06; C09K 2211/1029; C09K 2211/185; H01L 51/0072; H01L 51/0073; H01L 51/0085; H01L 51/0087; H01L 51/0094; H01L 51/5016; H05B 33/14
  See application file for complete search history.

(56) References Cited

U.S. PATENT DOCUMENTS

| | | | |
|---|---|---|---|
| 2013/0026909 A1 | 1/2013 | Zeng et al. | |
| 2013/0293094 A1* | 11/2013 | Dyatkin | H01L 51/0073 313/504 |

FOREIGN PATENT DOCUMENTS

| | | |
|---|---|---|
| JP | 2012-216818 A | 11/2012 |
| JP | 2013028605 A | 2/2013 |
| JP | 2013093432 A | 5/2013 |
| JP | 2013100239 A | 5/2013 |
| JP | 2013103937 A | 5/2013 |
| KR | 20120020901 A | 3/2012 |
| WO | 2007129702 A1 | 11/2007 |
| WO | 2007142083 A1 | 12/2007 |
| WO | 2010126234 A1 | 11/2010 |
| WO | 2012162325 A1 | 11/2012 |

OTHER PUBLICATIONS

Derwent abstract for KR 10-2012-0020901 A (Publication date: Mar. 2012).*
Derwent abstract for JP 2013-093432 A (publication date: May 2013).*
Machine translation for JP 2013-093432 A (publication date: May 2013).*
Office Action dated Apr. 19, 2017 from the corresponding Korean Application KR 10-2015-7026217 and English translation.; Applicant: Konica Minolta, Inc.: Total of 17 pages.
M.A. Baldo, et al; Nature; vol. 395; 1998; pp. 151-154.
M.A. Baldo, et al; Nature; vol. 403; No. 17; 2000; pp. 750-753.
International Preliminary Report on Patentability dated Sep. 29, 2015 for Application No. PCT/JP2014/059118 and English translation.
M.A. Baldo, et al; Nature; vol. 395; 1998; pp. 151-154 (not available).
M.A. Baldo, et al; Nature; vol. 403; No. 17; 2000; pp. 750-753 (not available).
International Search Report dated Apr. 15, 2014 for Application No. PCT/JP2014/050636 and English translation.
Notification of Reasons of Rejection dated Aug. 22, 2017 from the corresponding Japanese Patent Application No. JP 2014-067778 and English translation.
Office Action dated Sep. 21, 2017 from corresponding European Application No. 14775671.2.
Extended European Search Report dated Oct. 10, 2016 from corresponding European Application; Application No./ Patent No. 14775671.2-1555 / 2980878 PCT/JP2014059118; Applicant: Konica Minolta, Inc.; Total of 7 pages.

* cited by examiner

ORGANIC ELECTROLUMINESCENT ELEMENT, AND LIGHTING DEVICE AND DISPLAY DEVICE WHICH ARE PROVIDED WITH SAME

CROSS REFERENCE TO RELATED APPLICATION

This Application is a 371 of PCT/JP2014/059118 filed on Mar. 28, 2014 which, in turn, claimed the priority of Japanese Patent Application No. JP2013-072081 filed on Mar. 29, 2013, both applications are incorporated herein by reference.

TECHNICAL FILED

The present invention relates to an organic electroluminescent element, a display device and a lighting device provided with that organic electroluminescent element. More specifically, it relates to an organic electroluminescent element (hereafter, it is also called as an organic EL element) achieving a small resistance change of the light emitting layer when applying current over time. As a side effect of this property, it relates to an organic electroluminescent element excellent in chromaticity of the light emission spectrum with exhibiting a small change of light emission properties over time. It also relates to a lighting device and a display device provided with that organic electroluminescent element.

BACKGROUND

An organic electroluminescent element (hereafter, it is also called as an organic EL element) is a light emitting element having a constitution in which a light emitting layer containing a luminescent organic compound is interposed between a cathode and an anode. A hole injected from an anode and an electron injected from a cathode are recombined in the light emitting layer by applying an electric field, thus, an exciton is formed. It uses emitted light (fluorescence and phosphorescence) when the above exciton is deactivated. An organic EL element is a totally solid state element constituted by a film of an organic material having a thickness of only submicron and it enables to emit light at a voltage of several voltages to several ten voltages. Therefore, it is expected to be used for a flat display and an illumination of the next generation.

As a development of an organic EL device toward practical application, it was reported an organic EL element making use of phosphorescence emitted from an excited triplet state from Princeton University (refer to, for example, Non-patent document 1). Thereafter, there have been actively investigated materials emitting phosphorescence at room temperature (refer to, for example, Patent document 1 and Non-patent document 2). Further, organic EL elements operated by making use of phosphorescence emission make it possible to achieve a light emitting efficiency which is theoretically larger by about four times than those of conventional organic EL elements operated by making use of fluorescence emission. Therefore, starting from material development, a layer structure and electrodes of a light emitting element for the organic EL elements have been investigated and developed all over the world.

In the course of the research and development of the organic EL device, the most focused problem is the low durability of the organic EL device due to the fact the light emitting material itself is an organic compound. In order to improve the durability, many kinds of light emitting materials have been developed. At the same time, it has been made clear the importance of a host compound which receives and transfers an electron and a hole (they are generally called as a charge) to a light emitting material. The development of the host compound has been actively made (for example, refer to Patent documents 2, 3 and 4).

We have been focused on the clarification of the phenomenon in an interior of an organic EL element and we have eagerly analyzed the time-dependent change of the host compound contained in the light emitting layer. It was found that the fundamental primary factor which causes a various technical problems is a change of film resistance of the light emitting layer when applying current (to make luminescence) over time, and when keeping over time with non-luminescence condition.

Usually, it has been difficult to measure the resistance of a light emitting layer having a thickness of several tens of nm with a non-destructive method.

Recently, it has become possible to measure the resistance relatively easily by using impedance spectroscopy.

By using this method, it became possible to measure the resistance of a light emitting layer immediately after producing an organic EL element and at least one of the resistances during application of electric current and after keeping over time with non-light emitting state. It was found that the less the change of resistance, the less the voltage of the light emitting element, and that the chromaticity of the light emission spectrum is favorable. However, it was found that the change of resistance of a light emitting layer is still large and it is required to be further improved.

PRIOR ART

Patent Documents

Patent document 1: U.S. Pat. No. 6,097,147
Patent document 2: JP-A No. 2005-112765
Patent document 3: WO 2012/162325
Patent document 4: WO 2007/142083

Non-Patent Documents

Non-patent document 1: M. A. Baldo et al., Nature, vol. 395, p. 151 to 154 (1998)
Non-patent document 2: M. A. Baldo et al., Nature, vol. 403, no. 17, p. 750 to 753 (2000)

SUMMARY OF THE INVENTION

Problems to be Solved by the Invention

The present invention has been made in view of the above-described problems and situation. An object of the present invention is to provide an organic electroluminescent element achieving a small resistance change of the light emitting layer when applying current over time. As a side effect of this property, an object of the present invention is to provide an organic electroluminescent element excellent in chromaticity of the light emission spectrum with exhibiting a small change of light emission properties over time. In addition, an object of the present invention is to provide a lighting device provided with that organic electroluminescent element, and a display device.

Means to Solve the Problems

In order to solve the above-described problems, the present inventors have investigated the cause of the problems.

The present inventors examined many novel host compounds newly designed and conventionally known host compound for an organic electroluminescent element. It was searched for a compound which reduces the resistance change of an organic compound layer, in particular, a light emitting layer during application of current over time or after keeping over time with non-light emitting state.
The following mechanism of action was found and the present invention has been achieved.

In an element which is driven by applying an electric field such as an organic electroluminescent element, the compounds incorporated in the layers may take a plurality of electric states such as a neutral state, a radical state of an anion or a cation, and an excited state. Among these, it is considered that a radical state or an excited state in which an electric charge is localized in the molecule will likely interact with a neighborhood compound through an electric charge, and at the same time, it will be susceptible to be affected by the environmental change of the surrounding. The resistance change of the organic compound layer namely means the change of charge transporting property in the layer. The influence of the interaction or the environmental change will largely affect the resistance value of the layer. Consequently, it was found out a compound having a specific structure and an electrically neutral portion (neutral portion) as a technology to stabilize such a radical state.

A compound according to the present invention contains two or more aromatic heterocycles having 14 or more π electrons. Examples of these aromatic heterocycles are a condensed ring such as a carbazole ring or a dibenzofuran ring. These condensed rings have a large n-conjugated plane compared with a single ring. As a result it is favorable to receive or transfer a carrier. On the other hand, an electric charge will be localized in a radical state or an excited state of these condensed rings. In addition, due to the fact that they have a large n-conjugated plane, they will likely interact with each other. That is, these condensed rings are a portion which will be easily affected by the surrounding.

In the present invention, the specific feature of the compound is to contain two or more aromatic heterocycles having 14 or more π electrons, and further, to incorporate a portion in the molecule being sterically bulky and electrically neutral. By the introduction of a sterically bulky portion, it becomes possible to adjust the interaction between the aromatic heterocycles and the influence of the surrounding in an appropriate range. Moreover, since the sterically bulky portion is a neutral portion, the interaction of the neutral portions or the interaction of the neutral portion with electrically localized portion will be difficult to result in hardly affected. It will not affect the change of charge transport property. These are contained in the design policy of the compound.

Further, by uneven distribution of the aromatic heterocycles, in which an electric charge may be localized, the asymmetric property of the compound will be increased, and thus, it will prevent the molecule from becoming in the state of easily crystallization. This is one of the features of the compound.

By molecular designing based on the above-described design policy, it has become possible to provide an organic electroluminescent element containing an organic compound layer having a small change of film resistance value as described above.

Namely, the above-described problems of the present invention have been solved by the following embodiments.
1. An organic electroluminescent element comprising a pair of electrodes having therebetween one or a plurality of organic layers, wherein one or more of the organic layers contain a compound having a structure represented by Formula (1) shown below.

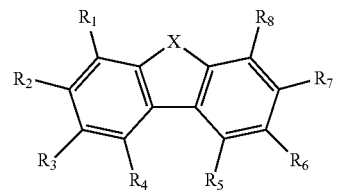

Formula (1)

In Formula (1), X represents O, S or $NR_9$. $R_1$ to $R_8$ each represent: a hydrogen atom, a deuterium atom, a halogen atom, a cyano group, an alkyl group, an alkenyl group, an alkynyl group, an alkoxy group, a carbonyl group, an amino group, a silyl group, a phosphine oxide group, an aromatic hydrocarbon ring group, an aromatic heterocyclic group, a non-aromatic hydrocarbon ring group, a non-aromatic heterocyclic group, or a substituent represented by Formula (2) shown below. At least one of $R_1$ to $R_8$ contains an aromatic heterocyclic group having 14 or more n electrons, and at least one of $R_1$ to $R_8$ is represented by Formula (2) shown below, provided that these groups may be further substituted with a substituent, and these groups may be the same or different. $R_9$ represent: a hydrogen atom, a deuterium atom, an alkyl group, an alkenyl group, an alkynyl group, an arylalkyl group, an aromatic hydrocarbon ring group, an aromatic heterocyclic group, a non-aromatic hydrocarbon ring group, or a non-aromatic heterocyclic group.

$$-(L)_n\text{-}Z\text{—}(R)_m \qquad \text{Formula (2)}$$

In Formula (2), L represents a linking group selected from the group consisting of an alkylene group, an alkenylene group, a m-phenylene group and a single ring aromatic heterocyclic group, the linking group may be substituted with a substituent. Z represents C, Si, Ge, P or P=O. R represents an alkyl group, an aromatic hydrocarbon ring group or an aromatic heterocyclic group each having a total carbon atom number of 1 to 20, provided that these groups may be further substituted with a substituent. "n" represents an integer of 2 to 8. "m" represents an integer of 2 to 3. When the compound contains a plurality of groups represented by Formula (2), a plurality of Ls, Zs an Rs each may be the same or different with each other, provided that adjacent Ls and adjacent Rs are not joined to form a ring.
2. An organic electroluminescent element described in the item 1, wherein L in Formula (2) represents a m-phenylene group
3. An organic electroluminescent element described in the items 1 or 2, wherein Z in Formula (2) represents Si.
4. An organic electroluminescent element described in any one of the items 1 to 3, wherein the compound represented by Formula (1) is a compound represented by Formula (3).

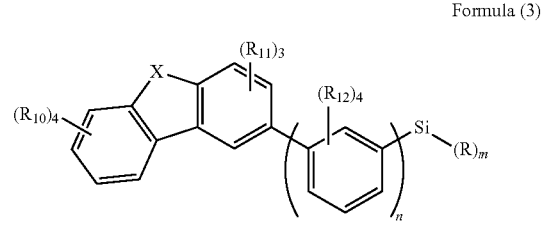

Formula (3)

In Formula (3), R, n, m and X each are synonymous with R, n, m and X in Formula (1) or Formula (2). $R_{10}$, $R_{11}$ and $R_{12}$ each represent: a hydrogen atom, a deuterium atom, a halogen atom, a cyano group, an alkyl group, an alkenyl group, an alkynyl group, an alkoxy group, a carbonyl group, an amino group, a silyl group, a phosphine oxide group, an aromatic hydrocarbon ring group, an aromatic heterocyclic group, a non-aromatic hydrocarbon ring group, or a non-aromatic heterocyclic group, provided that these groups may be further substituted with a substituent, and these groups may be the same or different.

5. An organic electroluminescent element described in any one of the items 1 to 4, wherein the compound having a structure represented by Formula (1) is a compound represented by Formula (4) or Formula (5) as shown below.

hydrogen atom, a deuterium atom, an alkyl group, an alkenyl group, an alkynyl group, an arylalkyl group, an aromatic hydrocarbon ring group, an aromatic heterocyclic group, a non-aromatic hydrocarbon ring group, or a non-aromatic heterocyclic group. $L_1$ and $L_2$ each represent a single bond or a divalent linking group.

6. An organic electroluminescent element described in any one of the items 1 to 4, wherein the compound having a structure represented by Formula (1) is a compound represented by Formula (6) as shown below.

Formula (4)

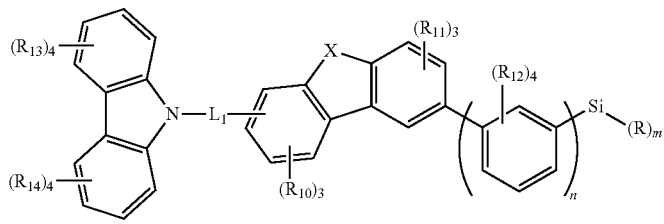

Formula (5)

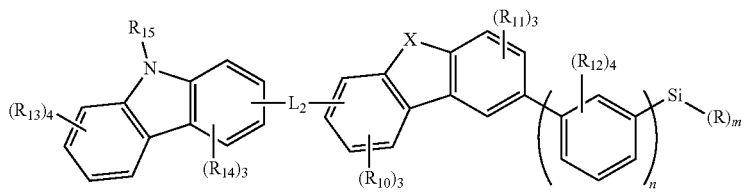

In Formula (4) and Formula (5), R, n, m and X each are synonymous with R, n, m and X in Formula (1) or Formula (2). $R_{10}$ to $R_{14}$ each represent: a hydrogen atom, a deuterium atom, a halogen atom, a cyano group, an alkyl group, an alkenyl group, an alkynyl group, an alkoxy group, a carbonyl group, an amino group, a silyl group, a phosphine oxide group, an aromatic hydrocarbon ring group, an aromatic heterocyclic group, a non-aromatic hydrocarbon ring group, or a non-aromatic heterocyclic group, provided that these groups may be further substituted with a substituent, and these groups may be the same or different. $R_{15}$ represent: a Formula (6)

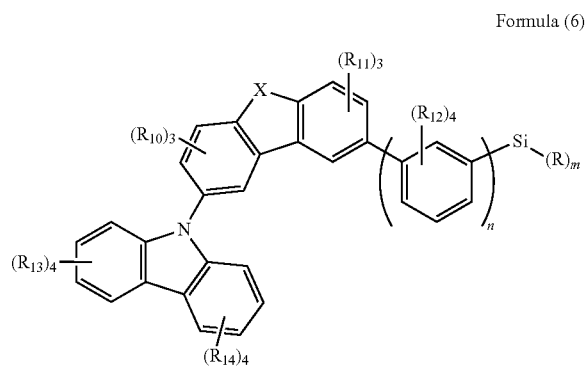

In Formula (6), R, n, m and X each are synonymous with R, n, m and X in Formula (1) or Formula (2). $R_{10}$ to $R_{14}$ each represent: a hydrogen atom, a deuterium atom, a halogen atom, a cyano group, an alkyl group, an alkenyl group, an alkynyl group, an alkoxy group, a carbonyl group, an amino group, a silyl group, a phosphine oxide group, an aromatic hydrocarbon ring group, an aromatic heterocyclic group, a non-aromatic hydrocarbon ring group, or a non-aromatic heterocyclic group, provided that these groups may be further substituted with a substituent, and these groups may be the same or different.

7. An organic electroluminescent element described in any one of the items 1 to 6, wherein one of the organic layers is a light emitting layer, and the light emitting layer contains the aforesaid compound as a host compound for organic electroluminescence.

8. An organic electroluminescent element described in any one of the items 1 to 7, wherein the aforesaid light emitting layer contains an iridium complex or a platinum complex, and the complex emits phosphorescence by applying current.

9. An organic electroluminescent element described in any one of the items 1 to 8, emitting white light.

10. A lighting device provided with an organic electroluminescent element described in any one of the items 1 to 9.

11. A display device provided with an organic electroluminescent element described in any one of the items 1 to 9.

Effects of the Invention

By the above-described embodiments of the present invention, it can provide an organic electroluminescent element achieving a small resistance change of the light emitting layer when applying current over time. As a side effect of this property, it can provide an organic electroluminescent element excellent in chromaticity (chromatic purity) of the light emission spectrum with exhibiting a small change of light emission properties over time. It can also provide a lighting device and a display device provided with that organic electroluminescent element.

EMBODIMENTS TO CARRY OUT THE INVENTION

Figure 1:
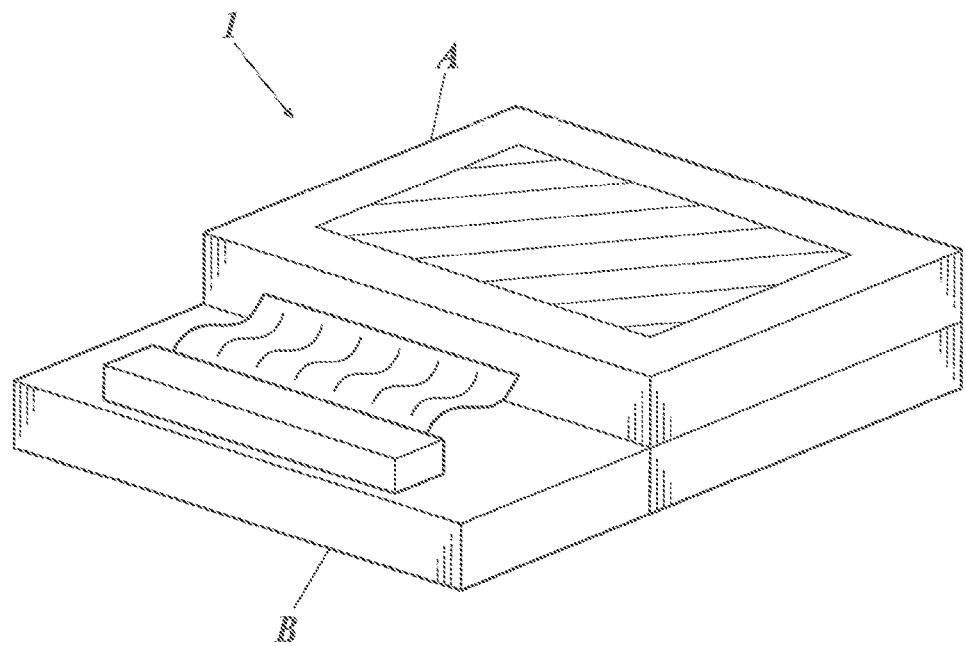
FIG. 1 is a schematic drawing to show an example of a display device constituted of an organic EL element.

An organic electroluminescent element of the present invention comprises a pair of electrodes having therebetween one or a plurality of organic layers, wherein one or more of the organic layers contain a compound having a structure represented by Formula (1). This feature is a technical feature commonly owned by the inventions relating to items 1 to 11.

As one of the embodiments of the present invention, it is preferable that L in Formula (2) represents a m-phenylene group from the viewpoint of exhibiting the effects of the present invention. In addition, it is preferable that Z in Formula (2) represents Si. Further, it is preferable that the compound represented by Formula (1) is a compound represented by Formula (3)

Further, it is preferable that the compound represented by Formula (1) is a compound represented by Formula (4) or Formula (5). Moreover, it is preferable that the compound represented by Formula (1) is a compound represented by Formula (6).

Further, it is preferable that one of the organic layers is a light emitting layer, and the light emitting layer contains the aforesaid compound as a host compound for organic electroluminescence. Moreover, it is preferable that the aforesaid light emitting layer contains an iridium complex or a platinum complex, and the complex emits phosphorescence by applying current. And it is preferable that an organic electroluminescent element emits white light.

An organic electroluminescent element of the present invention is suitable used for a lighting device and a display device.

The present invention and the constitution elements thereof, as well as configurations and embodiments, will be detailed in the following. In the present description, when two figures are used to indicate a range of value before and after "to", these figures are included in the range as a lowest limit value and an upper limit value.

<Molecular Orbital Calculation>

A compound having a structure represented by Formula (1) is a compound having a neutral portion in which a highest occupied molecular orbital (HOMO) and a lowest unoccupied molecular orbital (LUMO) show a small electron density, when it is calculated by the molecular orbital method, The neutral portion in the present invention indicates a portion in which a highest occupied molecular orbital (HOMO) and a lowest unoccupied molecular orbital (LUMO) show a small electron density, and being in a state of electrically neutral or close to neutral. More specifically, when a compound structure is calculated by molecular orbital calculations, there exist a portion where the electron cloud of HOMO is distributed, and a portion where the electron cloud of LUMO is distributed. Further, the portion having electron distributions of HOMO and LUMO are less than 10% is called a neutral portion. Here, the molecular orbital calculations referred to include from a calculation of the Hartree-Fock approximation called an ab initio method to a calculation called a density functional theory (DFT) method.

The molecular orbital methods relating to the present invention will be described. The molecular orbital calculation method in the present invention is preferably a density functional theory (DFT) method. In this case, there are used keywords such as B3LYP and B3PW91, for example. As a basis function for performing the calculation, it can be used 3-21G*, 6-31G, 6-31G*, cc-pVDZ, cc-pVTZ, LanL2DZ, and LanL2 MB.

Examples of software used for these molecular orbital calculations include Gaussian 03, QChem and Spartan. In the present invention, for a molecular orbital calculation, it is used a non-empirical molecular orbital calculation software Gaussian 03 (made by The US Gaussian Co. Ltd.): (Gaussian 03, Revision D.01, M. J. Frisch, G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, and J. A. Pople, Gaussian, Inc., Wallingford Conn., 2004)

<Specific Example of Molecular Orbital Calculation>

A neutral portion of the present invention will be described in detail with reference to a specific compound SH-1 described in the present application. The structure of SH-1 is shown below.

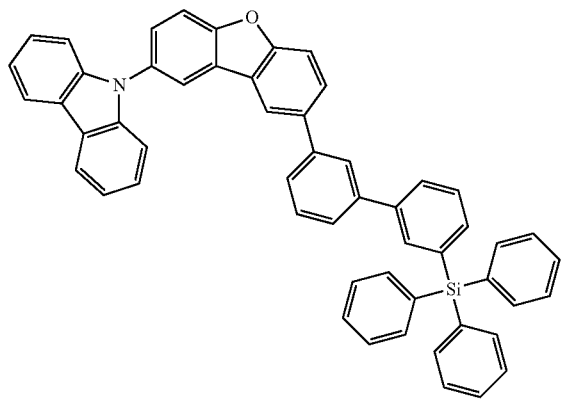

SH-1

At first, a stable structure and a molecular orbital in the stable structure were calculated using a molecular orbital calculation method. Specifically, SH-1 was modeled using a molecular modeling tool. Then, an optimization of the structure and a molecular orbital calculation were performed by using Gaussian 03 with specified conditions of: B3LYP as a functional, 6-31G* as a basis function, a spin multiplicity being 1, a charge being zero, "opt" for the keyword, and "pop=reg". In the log files after calculation, there were described a density distribution of a plurality of molecular orbitals including orbitals corresponding to HOMO and LUMO orbital energies in the respective wave functions for each atom.

Then, it was carried out calculation of an electron density distribution of HOMO and an electron density distribution of LUMO. Besides, the neutral portion of the present application is defined a site having substantially a small electron density distribution of HOMO and a small electron density distribution of LUMO and being in the state of neutral or close to neutral.

It will be detailed calculation of the electron density distribution of LUMO of the carbazole ring in SH-1 to show an example. From the molecular orbital corresponding to the LUMO orbital in the log files after completion of calculation (in the case of SH-1, it is 196th orbital), first, the orbital energies of the plural wave functions possessed by the nitrogen atom each are squared and added up. This value is defines as the LUMO existence ratio in the nitrogen atom. Further, for the carbon atoms and the hydrogen atoms other than nitrogen atom, which form the carbazole ring, it is carried out the same calculation done for the aforesaid nitrogen atom. In the present application, the sum of the electron density distribution of the total atoms which form the carbazole ring is defined as LUMO electron density distribution of the carbazole ring. In the same manner, the LUMO electron density distribution of other portion than the carbazole ring is calculated. Further, from the data of HOMO, it can calculate HOMO electron density distribution in the same manner as described above. For reference, the LUMO electron density distribution of the carbazole ring in SH-1 is 2.4%, the HOMO electron density distribution thereof is 85.1%. As a result of performing calculation for other portions of the molecule, it was revealed that the silicon atom and four benzene rings bonded to the silicon atom are the neutral portions which substantially have no electron cloud in HOMO and LUMO of SH-1.

Regarding the electron density distribution of the neutral portion, it is preferable that both HOMO and LUMO each have the electron density distribution of 10% or less, more preferably, 5% or less, and still more preferably, 3% or less.

A portion having a high electron density distribution in HOMO and LUMO can be defined by an electron density distribution in the same manner as a neutral portion. In this case, the portion having larger HOMO electron density distribution than LUMO electron density distribution may be defines as a HOMO portion, or the portion have larger HOMO electron density than the predetermined value may be defined as a HOMO portion. In the same way, the portion having larger LUMO electron density distribution than HOMO electron density distribution may be defines as a LUMO portion, or the portion having larger LUMO electron density than the predetermined value may be defined as a LUMO portion. When the portion having larger electron cloud than the predetermined value is defined as a HOMO portion or a LUMO portion, it is preferable that the existence ration is 50% or more, more preferably, 65% or more, still more preferably, 80% or more.

A compound having a structure represented by Formula (1) contains an atom having an atomic radius of 75 pm or more and a 3 or more valence in the aforesaid neutral portion. Examples of an atom having an atomic radius of 75 pm or more and a 3 or more valence include: a carbon atom, a nitrogen atom, a boron atom, a silicon atom, a phosphor atom, and a germanium atom. Preferable are a carbon atom and a silicon atom.

<Aromatic Heterocyclic Group Having 14 or More π Electrons>

The compound according to the present invention is characterized in having two or more aromatic heterocyclic groups each having 14 or more π electrons. Examples of an aromatic hydrocarbon ring having 14 or more π electrons include: a dibenzofuran ring, a dibenzothiophene ring, a carbazole ring, a xanthene ring, an acridine ring, a phenanthridine ring, a perimidine ring, a 1,10-phenanthroline ring, a phenazine ring, a phenalsadine ring, a tetrathiafulvalene ring, a thianthrene ring, a phenoxthine ring, a phenoxazine ring, a phenothiazine ring, a benzofuraindol ring, an indoloindole ring, and an indolocarbazole ring. Preferable are: a dibenzofuran ring, a dibenzothiophene ring, a carbazole ring, an indoloindole ring, and an indolocarbazoles ring. More preferable are: a dibenzofuran ring, a dibenzothiophene ring, and a carbazole ring.

The present invention and the constitution elements thereof, as well as configurations and embodiments, will be detailed in the following. In the present description, when two figures are used to indicate a range of value before and after "to", these figures are included in the range as a lowest limit value and an upper limit value.

<<Compound Represented by Formula (1)>>

An organic electroluminescent element of the present invention comprises a pair of electrodes having therebetween one or a plurality of organic layers, wherein one or more of the organic layers contain a compound having a structure represented by Formula (1).

It is preferable that a light emitting layer contains a compound represented by Formula (1) for an organic EL element material. In the present invention, an organic layer is a layer which contains an organic material.

It will be described a compound contained an organic EL element material in an organic EL element. A compound according to the present invention is represented by Formula (1).

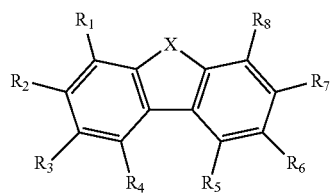

Formula (1)

In Formula (1), X represents O, S or $NR_9$. Preferably, X represents O, or S. $R_9$ represents: a hydrogen atom, a deuterium atom, an alkyl group, an alkenyl group, an alkynyl group, an aromatic hydrocarbon ring group, an aromatic heterocyclic group, a non-aromatic hydrocarbon ring group, or a non-aromatic heterocyclic group. Preferably, $R_9$ represents an alkyl group or an aromatic hydrocarbon ring group. More preferably, it represents an aromatic hydrocarbon ring group, and still more preferably, it represents a benzene ring.

Examples of an alkyl group are: a methyl group, an ethyl group, an n-propyl group, an isopropyl group, an n-butyl group, a t-butyl group, a 1-ethylpropyl group, a 2-methylhexyl group, a pentyl group, an adamantyl group, an n-decyl group, and an n-dodecyl group. Among them, preferable are a methyl group, an ethyl group, an n-propyl group, and an isopropyl group.

Examples of an aromatic hydrocarbon ring group include: a benzene ring, a biphenyl ring, a biphenylene ring, a naphthalene ring, an azulene ring, an anthracene ring, a phenanthrene ring, a pyrene ring, a chrysene ring, a naphthacene ring, a triphenylene ring, an o-terphenyl ring, a m-terphenyl ring, a p-terphenyl ring, an acenaphthene ring, a coronene ring, a fluorene ring, a fluoranthrene ring, a naphthacene ring, a pentacene ring, a perylene ring, a pentaphene ring, a picene ring, a pyrene ring, a pyranthrene ring, and an athranthrene ring. Among them, preferable is a benzene ring.

In Formula (1), $R_1$ to $R_8$ each represent: a hydrogen atom, a deuterium atom, a halogen atom, a cyano group, an alkyl group, an alkenyl group, an alkynyl group, an alkoxy group, a carbonyl group, an amino group, a silyl group, a phosphine oxide group, an aromatic hydrocarbon ring group, an aromatic heterocyclic group, a non-aromatic hydrocarbon ring group, a non-aromatic heterocyclic group, or a group represented by Formula (2) shown below, and at least one of $R_1$ to $R_8$ contains a group having an aromatic heterocyclic group having 14 or more π electrons.

-(L)$_n$-Z—(R)$_m$  Formula (2)

In Formula (1), preferably, $R_1$ to $R_8$ each represent a hydrogen atom, an alkyl group, an aromatic hydrocarbon ring group, or an aromatic heterocyclic group. More preferably, it is a hydrogen atom, an aromatic hydrocarbon ring group, or an aromatic heterocyclic group.

Examples of an aromatic hydrocarbon ring group include: a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, a m-terphenyl ring, a p-terphenyl ring, an acenaphthene ring, a coronene ring, a fluorene ring, a fluoranthrene ring, a naphthacene ring, a pentacene ring, a perylene ring, a pentaphene ring, a picene ring, a pyrene ring, a pyranthrene ring, and an athranthrene ring. Among them, preferable is a benzene ring.

Examples of an aromatic heterocyclic group include: a furan ring, a thiophene ring, an oxazole ring, a pyrrole ring, a pyridine ring, a pyridazine ring, a pyrimidine ring, a pyrazine ring, a triazine ring, an oxadiazole ring, a triazole ring, an imidazole ring, a pyrazole ring, a triazole ring, an indole ring, a benzimidazole ring, a benzothiaxole ring, a benzoxazole ring, quinoxaline ring, a quinazoline ring, a phthalazine ring, a thienothiophene ring, a carbazole ring, an azacarbazole ring (indicating a ring structure in which one of the carbon atoms constituting the carbazole ring is replaced with nitrogen atoms), a dibenzofuran ring, a dibenzothiophene ring, a ring obtained by substituting at least one of arbitral carbon atoms constituting a benzothiophene ring or a benzofuran ring with a nitrogen atom, a benzodifuran ring, a benzodithiophene ring, an acridine ring, a benzoquinoline ring, a phenazine ring, a phenanthridine ring, a phenanthroline ring, a cyclazine ring, a quindoline ring, a tepenidine ring, a quinindoline ring, a triphenodithiazine ring, a triphenodioxazine ring, a phenanthrazine ring, an anthrazine ring, a perimidine ring, a naphthofuran ring, a naphthothiophene ring, a naphthodifuran ring, a naphthodithiophene ring, an anthrafuran ring, an anthradifuran ring, an anthrathiophene ring, an anthradithiophene ring, a thianthrene ring, a phenoxatiin ring, a dibenzocarbazole ring, an indolocarbazole ring, a dithienobenzene ring, an indoloindole ring, and a benzofuroindole ring. Preferable are a dibenzofuran ring, a dibenzothiophene ring, a carbazole ring, an indoloindole ring and a benzofuroindole ring. More preferable is a carbazole ring.

In Formula (2), L represents a linking group selected from the group consisting of an alkylene group, an alkenylene group, a m-phenylene group and a single ring aromatic heterocyclic group, the linking group may be substituted with a substituent. Preferably, it is a m-phenylene group.

Examples of an alkylene group represented by L in Formula (2) include: a methylene group, a methylmethylene group, a dimethylmethylene group, an ethylene group, a propylene group, a butylene group, a hexylene group, an octylene group, a dodecanylene group, a divalent cycloalkylene group (including a cycloalkylidene group) such as a 2-cyclopentylene group, a 1,3-cyclopentylene group, a cyclopentylidene group, a 1,2-cyclohexylene group, 1,3- cyclohexylene, 1,4-cyclohexylene group, and a cyclohexylidene group. Preferable is a methylene group.

Examples of an alkenylene group are: an ethynylene group, a propenylene group, and a butenylene group. Preferable is an ethynylene group.

Examples of a single ring aromatic heterocyclic group are: a furan ring, a thiophene ring, an oxazole ring, a pyrrole ring, a pyridine ring, a pyridazine ring, a pyrimidine ring, a pyrazine ring, a triazine ring, an oxadiazole ring, a triazole ring, an imidazole ring, a pyrazole ring, and a triazole ring. Preferable are: a furan ring, a thiophene ring, a pyridine ring, a pyrimidine ring, a pyrazine ring, and a triazine ring. More preferable are: a thiophene ring, a pyridine ring, a pyrimidine ring, and a pyrazine ring.

In Formula (2), Z represents C, Si, Ge, P or P=O. Preferably, Z represents C, Si, and more preferably, Z represents Si. When Z is C, Si, Ge, P or P=O, it becomes possible that Z has two or three substituents thereon. Since Z can have a sterically bulky substituent, it is supposed that it will prevent the molecule from being in a state of easily crystallized and it will improve the stability over time.

In Formula (2), R represents an alkyl group, an aromatic hydrocarbon ring group or an aromatic heterocyclic group each having a total carbon atom number of 1 to 20, provided that these groups may be further substituted with a substituent. Here, the total carbon atom number indicates the number of carbon atoms including the substituent. By setting R to have the total carbon atom number of 1 to 20, it becomes possible to achieve compatibility of both thin film morphology and sublimation property. Thus, it can maintain a production aptitude by evaporation deposition method, and a long life can be achieved by improvement of morphology.

In Formula (2), examples of an alkyl group represented by R include: a methyl group, an ethyl group, an n-propyl group, an isopropyl group, an n-butyl group, a t-butyl group, a 1-ethylpropyl group, a 2-methylhexyl group, a pentyl group, an adamantyl group, an n-decyl group, and an n-dodecyl group. Among them, preferable are a methyl group, an ethyl group, an n-propyl group, and an isopropyl group.

Examples of an aromatic hydrocarbon ring group are: a benzene ring, a biphenyl ring, a biphenylene ring, a naphthalene ring, an azulene ring, an anthracene ring, a phenanthrene ring, a pyrene ring, a chrysene ring, a naphthacene ring, a triphenylene ring, an o-terphenyl ring, a m-terphenyl ring, a p-terphenyl ring, an acenaphthene ring, a coronene ring, a fluorene ring, a fluoranthrene ring, a naphthacene ring, a pentacene ring, a perylene ring, a pentaphene ring, a picene ring, a pyrene ring, a pyranthrene ring, and an athranthrene ring. Preferable is a benzene ring.

Examples of an aromatic heterocyclic group include: a furan ring, a thiophene ring, an oxazole ring, a pyrrole ring, a pyridine ring, a pyridazine ring, a pyrimidine ring, a pyrazine ring, a triazine ring, an oxadiazole ring, a triazole ring, an imidazole ring, a pyrazole ring, and a triazole ring, an indole ring, a benzimidazole ring, a benzothiaxole ring, a benzoxazole ring, quinoxaline ring, a quinazoline ring, a phthalazine ring, a thienothiophene ring, a carbazole ring, an azacarbazole ring (indicating a ring structure in which one of the carbon atoms constituting the carbazole ring is replaced with nitrogen atoms), a dibenzofuran ring, a dibenzothiophene ring, a ring obtained by substituting at least one of arbitral carbon atoms constituting a benzothiophene ring or a benzofuran ring with a nitrogen atom, a benzodifuran ring, a benzodithiophene ring, an acridine ring, a benzoquinoline ring, a phenazine ring, a phenanthridine ring, a phenanthroline ring, a cyclazine ring, a quindoline ring, a tepenidine ring, a quinindoline ring, a triphenodithiazine ring, a triphenodioxazine ring, a phenanthrazine ring, an anthrazine ring, a perimidine ring, a naphthofuran ring, a naphthothiophene ring, a naphthodifuran ring, a naphthodithiophene ring, an anthrafuran ring, an anthradifuran ring, an anthrathiophene ring, an anthradithiophene ring, a thianthrene ring, a phenoxatiin ring, a dibenzocarbazole ring, an indolocarbazole ring, and a dithienobenzene ring. Preferable are a thiophene ring and a pyridine ring.

In Formula (2), "n" represents an integer of 2 to 8. Preferably, "n" represents an integer of 2 to 4. "m" represents an integer of 2 to 3. Preferably, "m" represents an integer of 3. When the compound contains a plurality of groups represented by Formula (2), a plurality of Ls, Z an R each may be the same or different with each other, provided that adjacent Ls and adjacent Rs are not joined to form a ring.

By suitably designing Formula (2), it can adjust the interaction of the compounds and effects of the environment in the appropriate range. Thus, it is possible to provide an organic electroluminescent element without giving large effect to the electron transporting property had having a small film resistance change.

<<Compound Represented by Formula (3)>>

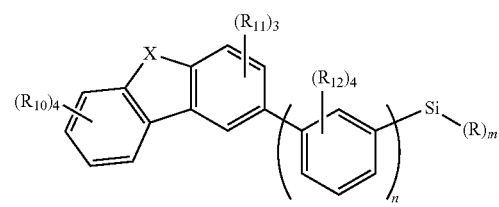

Formula (3)

In Formula (3), X is synonymous with X in Formula (1), and R, n, and m each are synonymous with R, n, and m in Formula (2). In Formula (3), $R_{10}$ to $R_{12}$ each represent: a hydrogen atom, a deuterium atom, a halogen atom, a cyano group, an alkyl group, an alkenyl group, an alkynyl group, an alkoxy group, a carbonyl group, an amino group, a silyl group, a phosphine oxide group, an aromatic hydrocarbon ring group, an aromatic heterocyclic group, a non-aromatic hydrocarbon ring group, or a non-aromatic heterocyclic group. Preferable are a hydrogen atom, an alkyl group, an aromatic hydrocarbon ring group, and an aromatic heterocyclic group. More preferable are a hydrogen atom, an aromatic hydrocarbon ring group, and an aromatic heterocyclic group.

At least one of $R_{10}$ and $R_{11}$ is a substituent containing an aromatic heterocyclic group having 14 or more π electrons. Preferably, at least one of $R_{10}$ is a group containing an aromatic heterocyclic group having 14 or more π electrons.

Examples of an aromatic hydrocarbon ring group include: a benzene ring, a biphenyl ring, a biphenylene ring, a naphthalene ring, an azulene ring, an anthracene ring, a phenanthrene ring, a pyrene ring, a chrysene ring, a naphthacene ring, a triphenylene ring, an o-terphenyl ring, a m-terphenyl ring, a p-terphenyl ring, an acenaphthene ring, a coronene ring, a fluorene ring, a fluoranthrene ring, a naphthacene ring, a pentacene ring, a perylene ring, a pentaphene ring, a picene ring, a pyrene ring, a pyranthrene ring, and an athranthrene ring. Among them, preferable is a benzene ring.

Examples of an aromatic heterocyclic group include: a furan ring, a thiophene ring, an oxazole ring, a pyrrole ring, a pyridine ring, a pyridazine ring, a pyrimidine ring, a pyrazine ring, a triazine ring, an oxadiazole ring, a triazole ring, an imidazole ring, a pyrazole ring, a triazole ring, an indole ring, a benzimidazole ring, a benzothiaxole ring, a benzoxazole ring, quinoxaline ring, a quinazoline ring, a phthalazine ring, a thienothiophene ring, a carbazole ring, an azacarbazole ring (indicating a ring structure in which one of the carbon atoms constituting the carbazole ring is replaced with nitrogen atoms), a dibenzofuran ring, a dibenzothiophene ring, a ring obtained by substituting at least one of arbitral carbon atoms constituting a benzothiophene ring or a benzofuran ring with a nitrogen atom, a benzodifuran ring, a benzodithiophene ring, an acridine ring, a benzoquinoline ring, a phenazine ring, a phenanthridine ring, a phenanthroline ring, a cyclazine ring, a quindoline ring, a tepenidine ring, a quinindoline ring, a triphenodithiazine ring, a triphenodioxazine ring, a phenanthrazine ring, an anthrazine ring, a perimidine ring, a naphthofuran ring, a naphthothiophene ring, a naphthodifuran ring, a naphthodithiophene ring, an anthrafuran ring, an anthradifuran ring, an anthrathiophene ring, an anthradithiophene ring, a thianthrene ring, a phenoxatiin ring, a dibenzocarbazole ring, an indolocarbazole ring, a dithienobenzene ring, an indoloindole ring, and a benzofuroindole ring. Preferable are a dibenzofuran ring, a dibenzothiophene ring, and a carbazole ring. More preferable is a carbazole ring.

In Formula (3), $R_{10}$ to $R_{12}$ each may further have a substituent, and $R_{10}$ to $R_{12}$ each may be the same or different.

<<<Compound Represented by Formula (4) or Formula (5)>>>

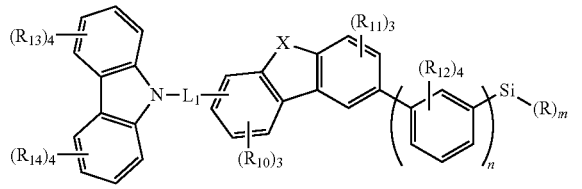

Formula (4)

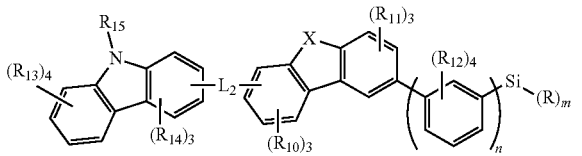

Formula (5)

In Formulas (4) and (5), X, R, n, and m each are synonymous with X, R, n, and m in Formula (3).

In Formulas (4) and (5), $R_{10}$ to $R_{14}$ each represent: a hydrogen atom, a deuterium atom, a halogen atom, a cyano group, an alkyl group, an alkenyl group, an alkynyl group, an alkoxy group, a carbonyl group, an amino group, a silyl group, a phosphine oxide group, an aromatic hydrocarbon ring group, an aromatic heterocyclic group, a non-aromatic hydrocarbon ring group, or a non-aromatic heterocyclic group. Preferable are a hydrogen atom, an alkyl group, an aromatic hydrocarbon ring group, and an aromatic heterocyclic group. More preferable are a hydrogen atom, an aromatic hydrocarbon ring group, and an aromatic heterocyclic group.

As an aromatic hydrocarbon ring group, it can be cited the groups cited for $R_{10}$ to $R_{12}$ in the aforesaid Formula (3).

As an aromatic heterocyclic group, it can be cited the groups cited for $R_{10}$ to $R_{12}$ in the aforesaid Formula (3). Preferable are a dibenzofuran ring, a dibenzothiophene ring and a carbazole ring. More preferable is a carbazole ring.

In Formulas (4) and (5), $R_{10}$ to $R_{14}$ each may further have a substituent, and $R_{10}$ to $R_{14}$ each may be the same or different.

In Formula (5), $R_{15}$ represents: a hydrogen atom, a deuterium atom, an alkyl group, an alkenyl group, an alkynyl group, an aromatic hydrocarbon ring group, an aromatic heterocyclic group, a non-aromatic hydrocarbon ring group, or a non-aromatic heterocyclic group. Preferable are an alkyl group and an aromatic hydrocarbon ring group. More preferable is an aromatic hydrocarbon ring group. In particular, a benzene ring is preferable.

Examples of an alkyl group are: a methyl group, an ethyl group, an n-propyl group, an isopropyl group, an n-butyl group, a t-butyl group, a 1-ethylpropyl group, a 2-methylhexyl group, a pentyl group, an adamantyl group, an n-decyl group, and an n-dodecyl group. Among them, preferable are a methyl group, an ethyl group, an n-propyl group, and an isopropyl group.

Examples of an aromatic hydrocarbon ring group include: a benzene ring, a biphenyl ring, a biphenylene ring, a naphthalene ring, an azulene ring, an anthracene ring, a phenanthrene ring, a pyrene ring, a chrysene ring, a naphthacene ring, a triphenylene ring, an o-terphenyl ring, a m-terphenyl ring, a p-terphenyl ring, an acenaphthene ring, a coronene ring, a fluorene ring, a fluoranthrene ring, a naphthacene ring, a pentacene ring, a perylene ring, a pentaphene ring, a picene ring, a pyrene ring, a pyranthrene ring, and an athranthrene ring. Among them, preferable is a benzene ring.

In Formulas (4) and (5), L1 and L2 each represent a single bond or a divalent linking group.

Examples of a divalent linking group include: an alkylene group, an alkenylene group, an ether group, an ester group, a carbonyl group, an amino group, an amide group, a silyl group, a phosphine oxide group, a benzene ring group, a carbazole ring group, a dibenzofuran ring, a dibenzothiophene ring, a pyridine ring group, a pyrazine ring group, an indoloindole ring group, an indole ring group, a benzofuran ring group, a benzothiophene ring group, and an imidazole ring group. Preferable are a single bond, a benzene ring group, a carbazole ring group, a dibenzofuran ring, and a dibenzothiophene ring. More preferable is a single bond.

Examples of a divalent linking group are shown below. These divalent linking groups may be further substituted with a substituent. The present invention is not limited to them.

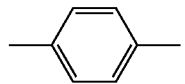

L-1

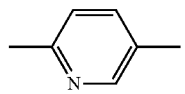

L-2

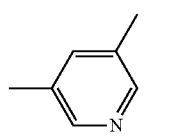

L-3

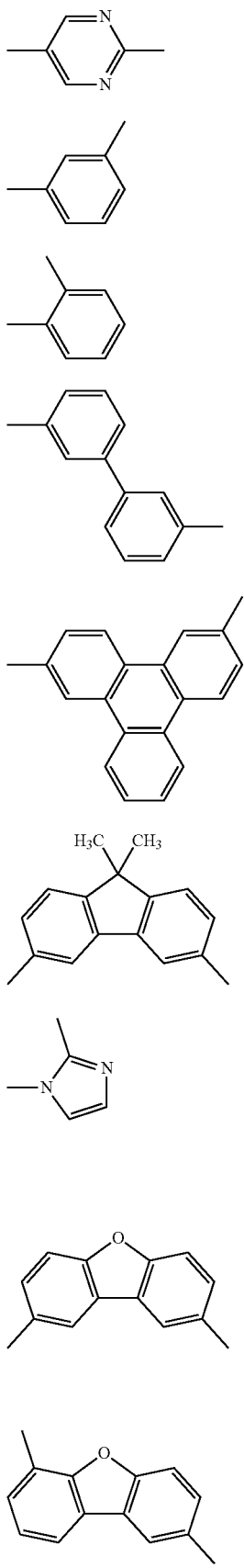
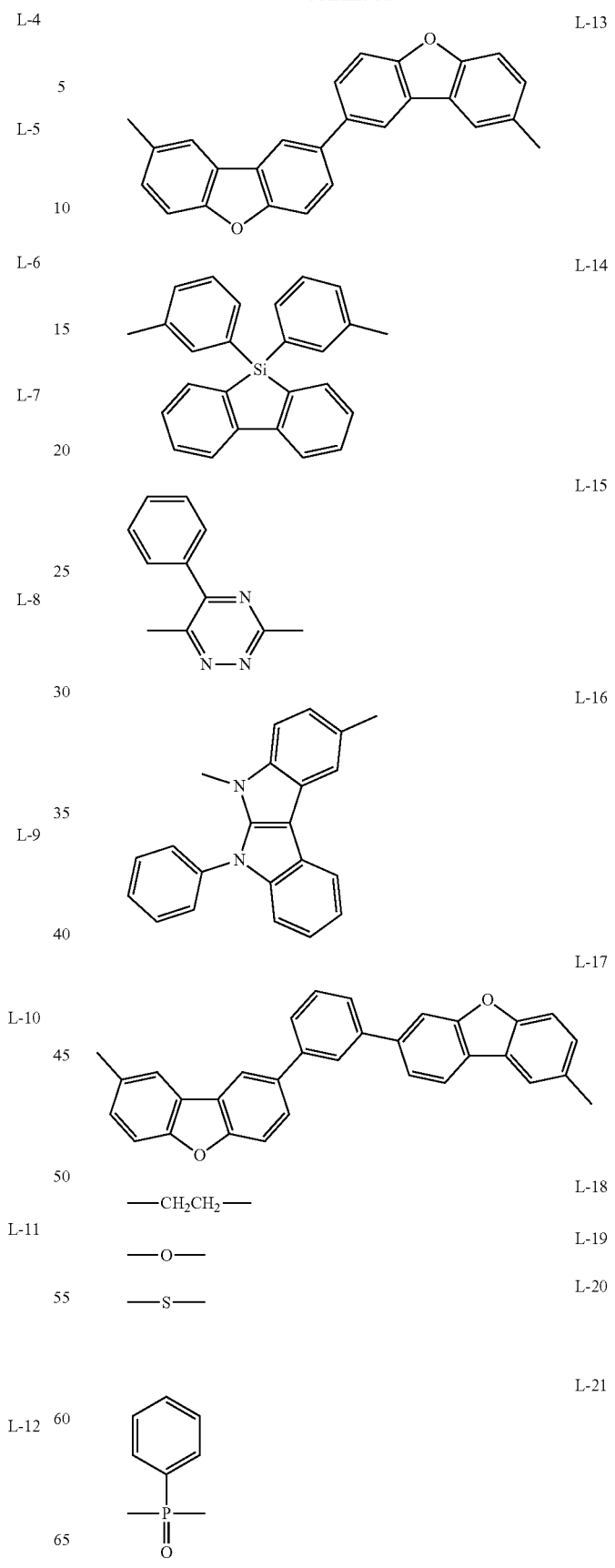

L-22 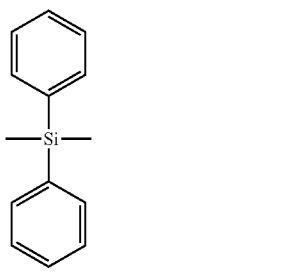
L-23 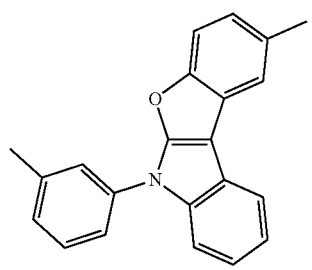
L-24 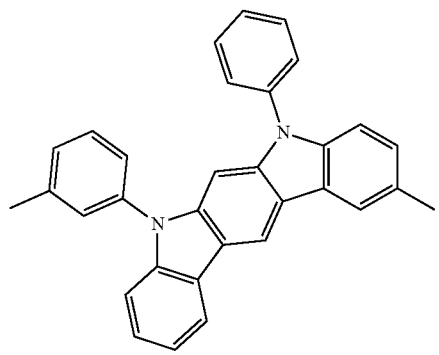
L-25 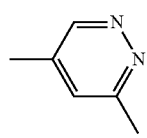
L-26 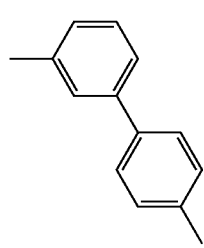
L-27 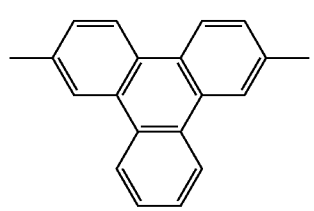
L-28 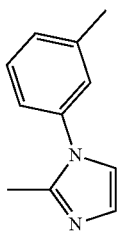
L-29 
L-30 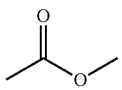
L-31 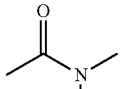
L-32 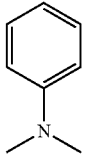
L-33 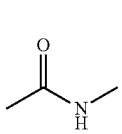
L-34 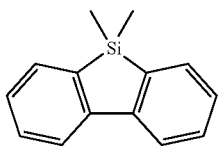
L-35 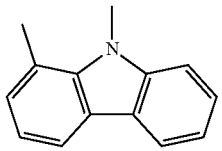
L-36 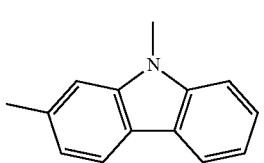
L-37
L-38

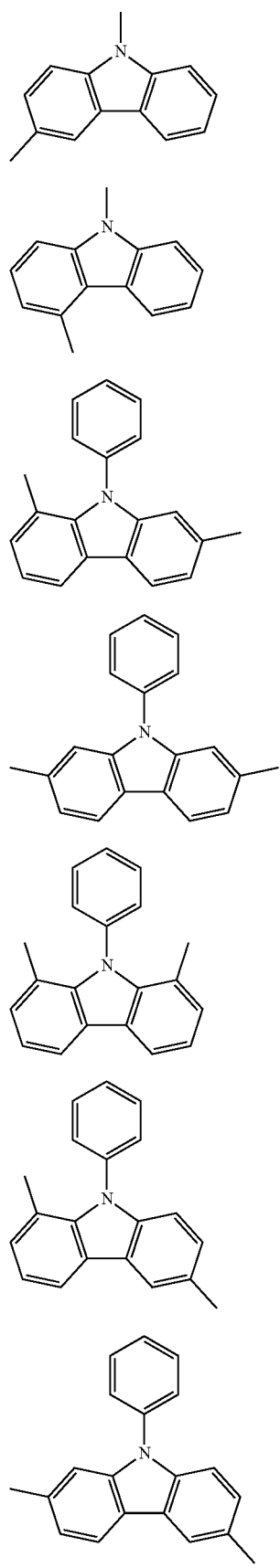
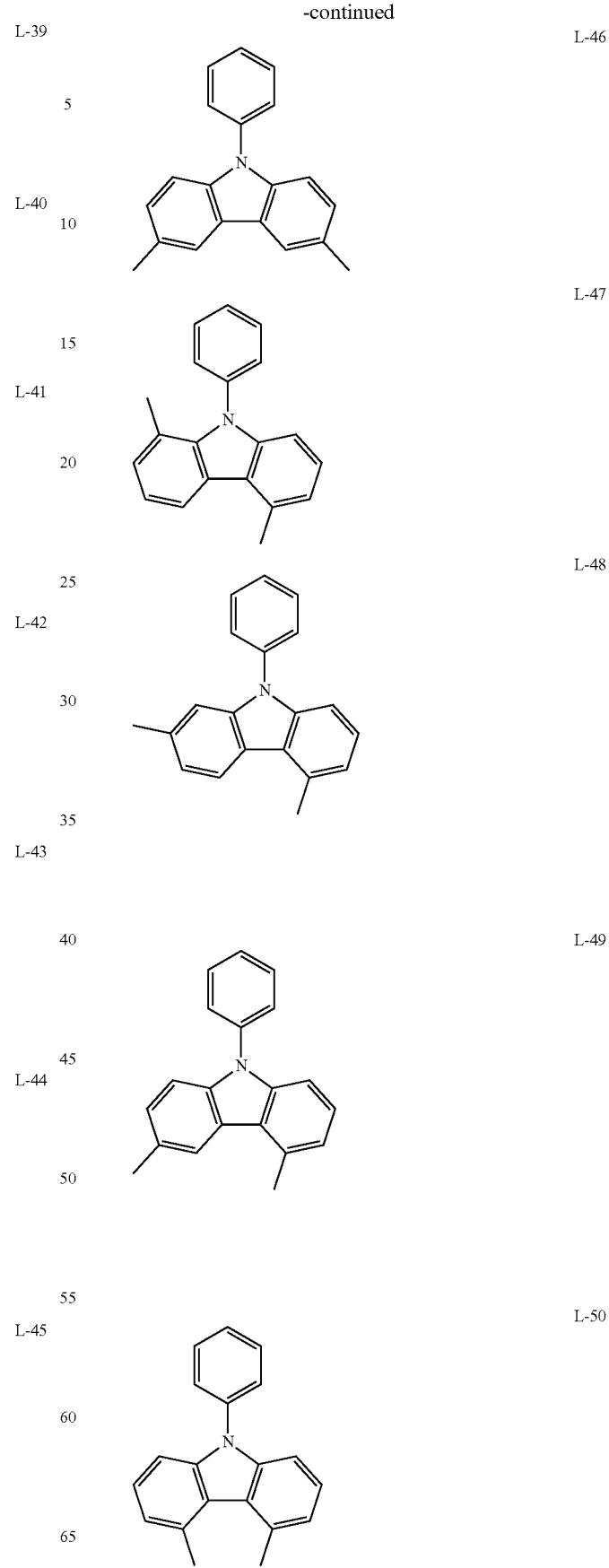

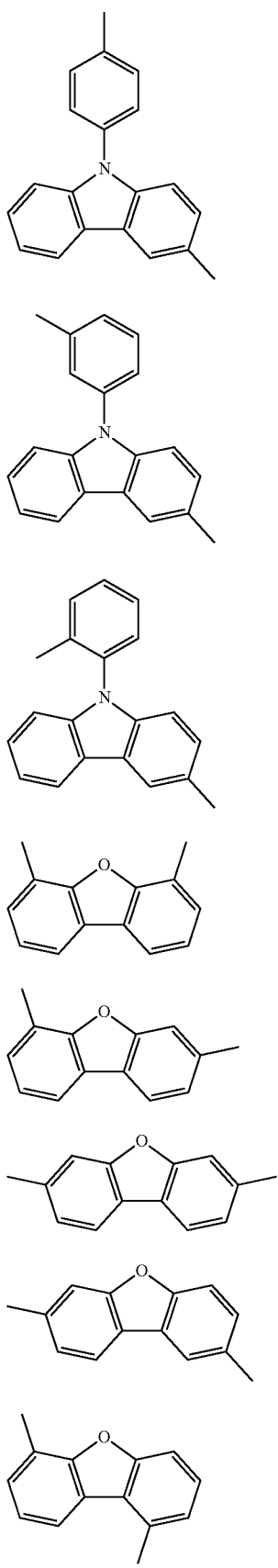
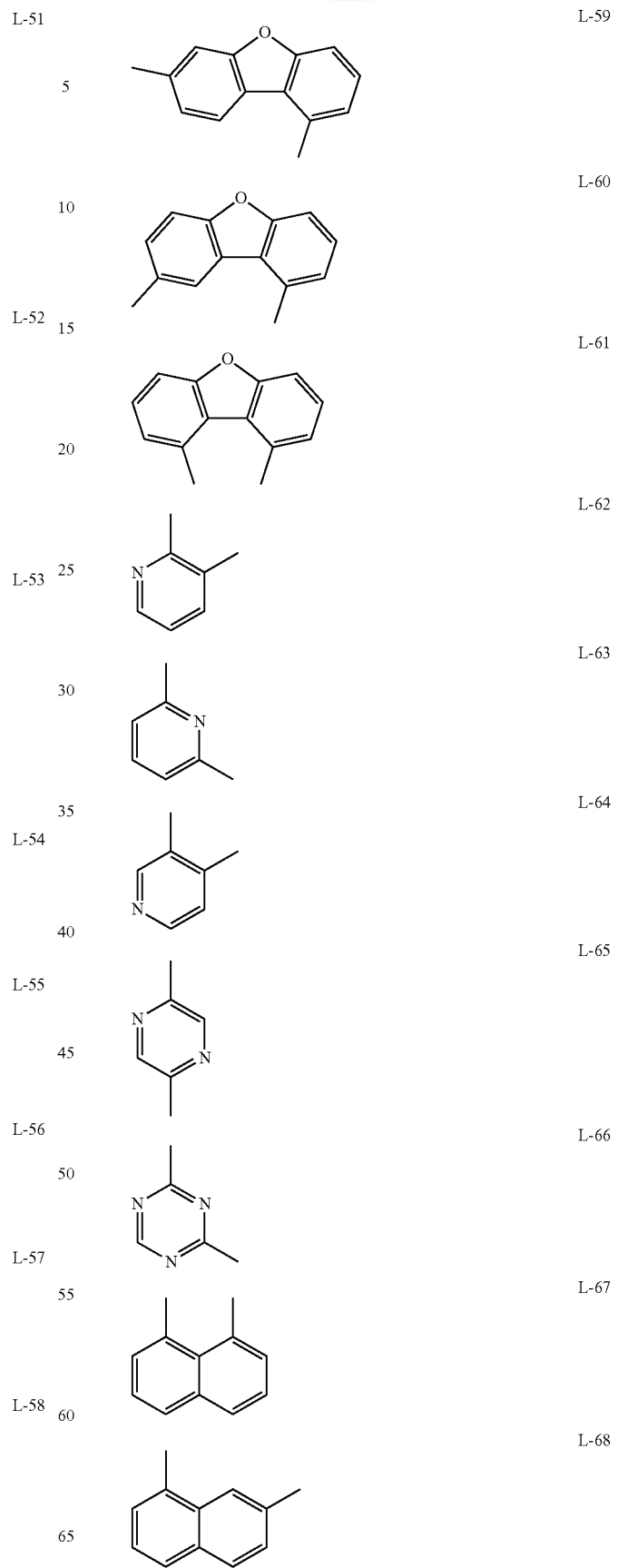

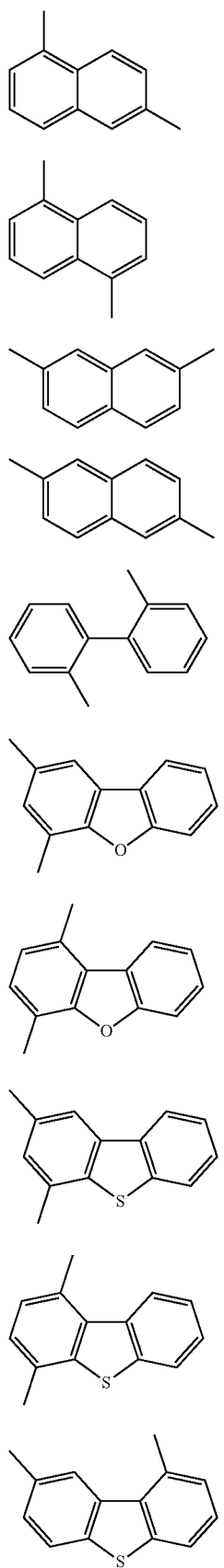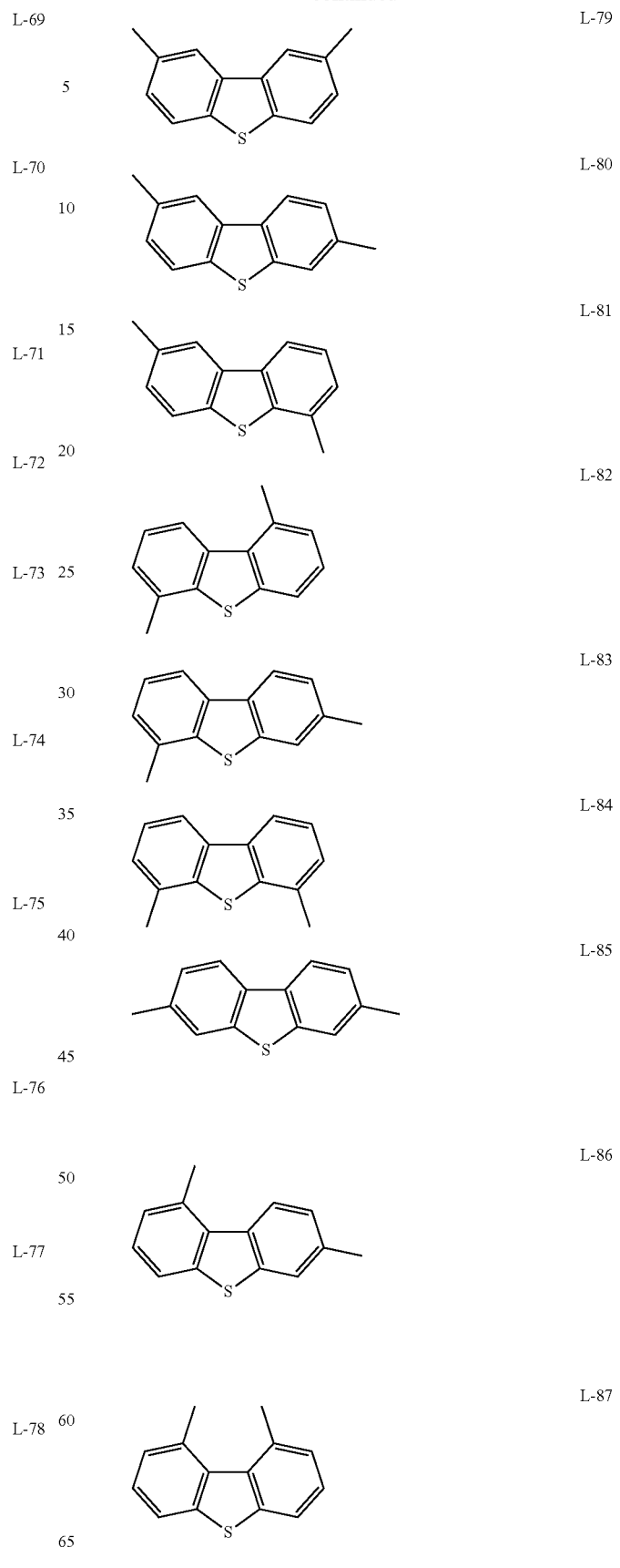

<<<Compound Represented by Formula (6)>>>
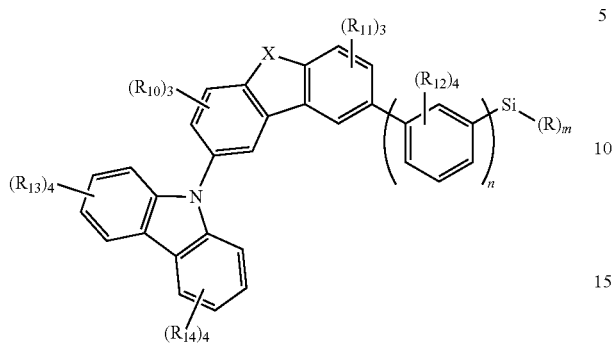
Formula (6)
In Formula (6), R, n, m and X each are synonymous with R, n, m and X in Formula (1) or Formula (2). In Formula (6), $R_{10}$ to $R_{14}$ each synonymous with $R_{10}$ to $R_{14}$ in Formula (14)
Specific examples of a compound represented by Formulas (1) to (6) are shown in the following. However, the present invention is not limited to them.
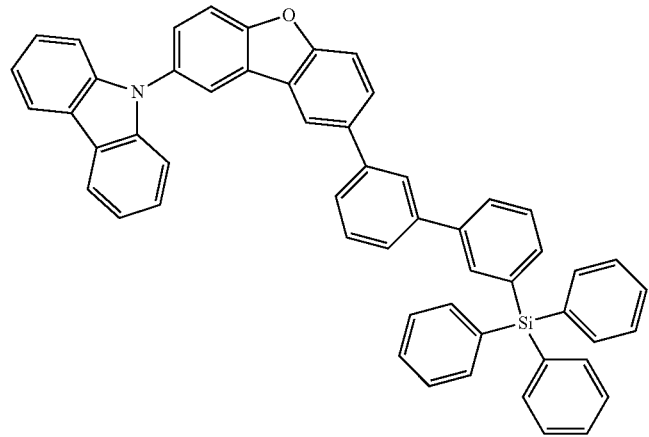
SH-1
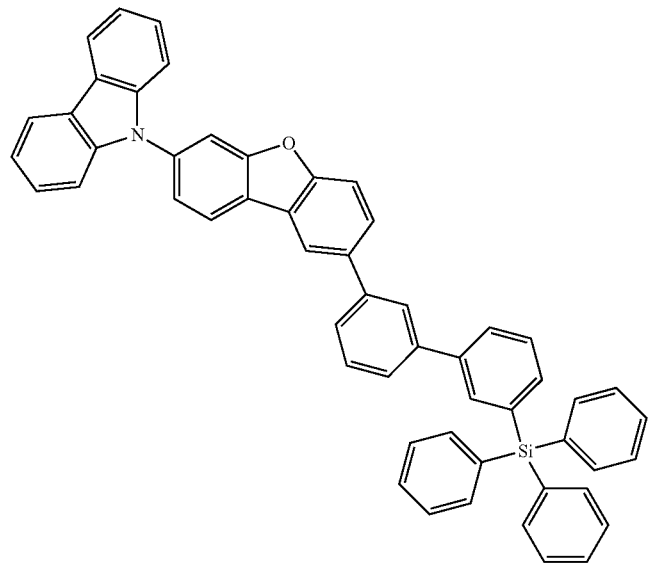
SH-2

-continued
SH-3
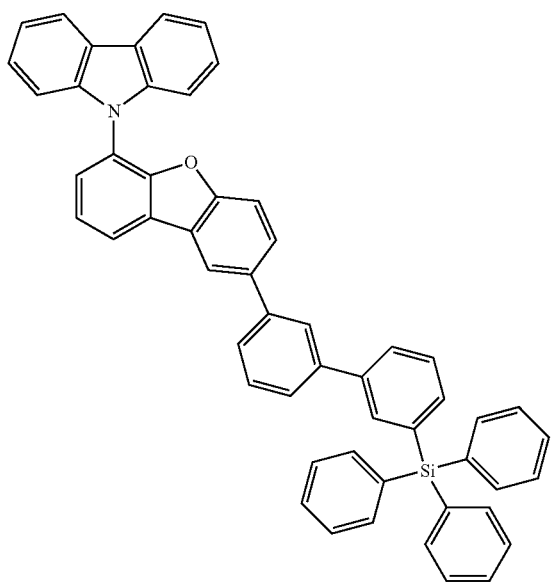
SH-4
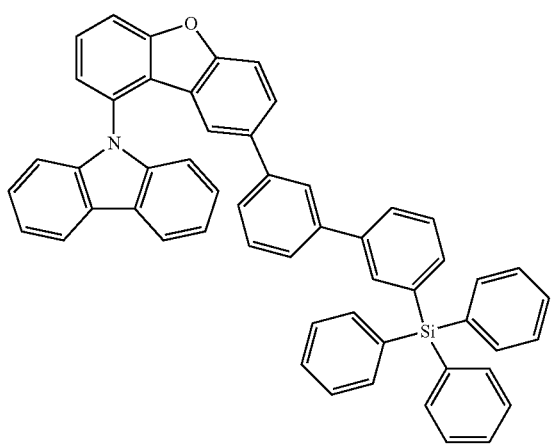
SH-5
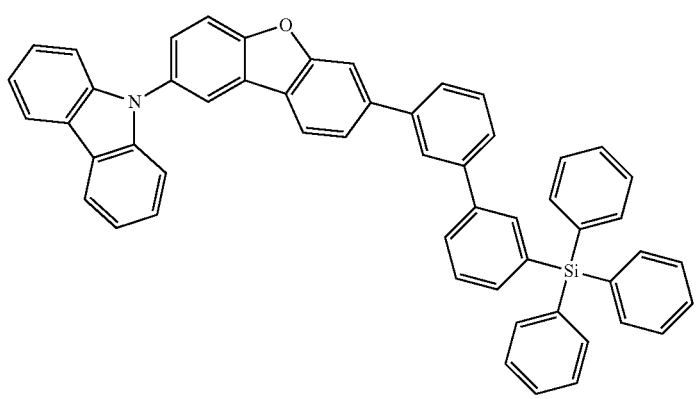

SH-6
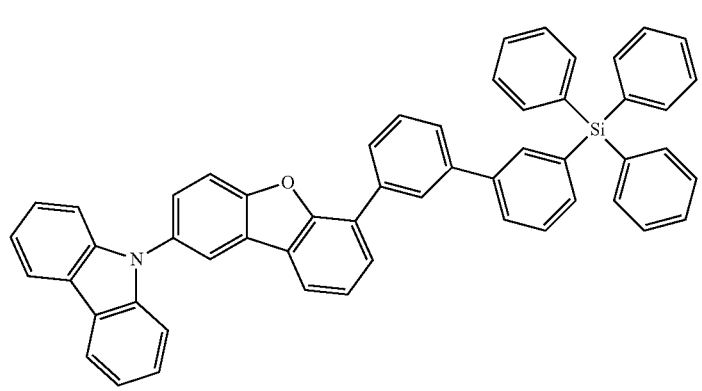
SH-7
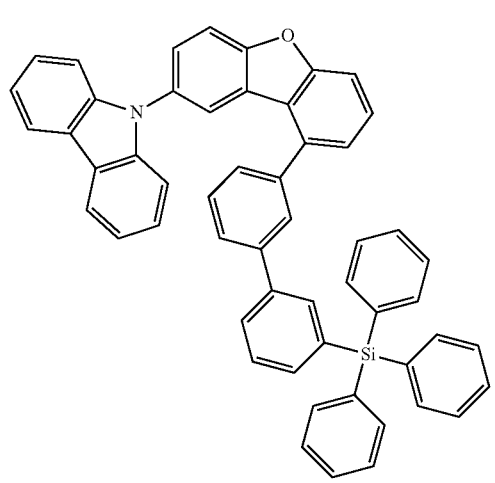
SH-8
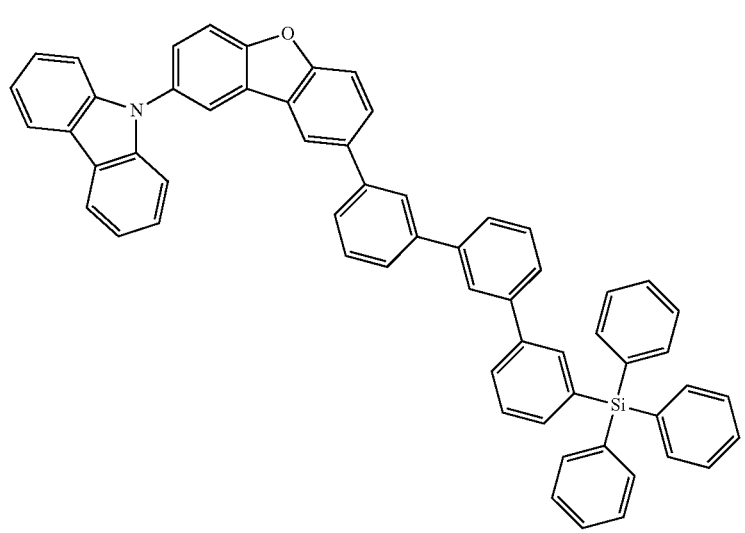

SH-9
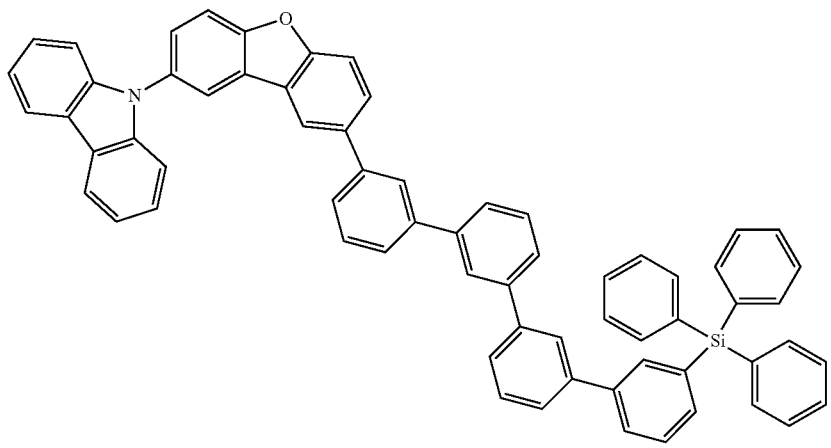
SH-10
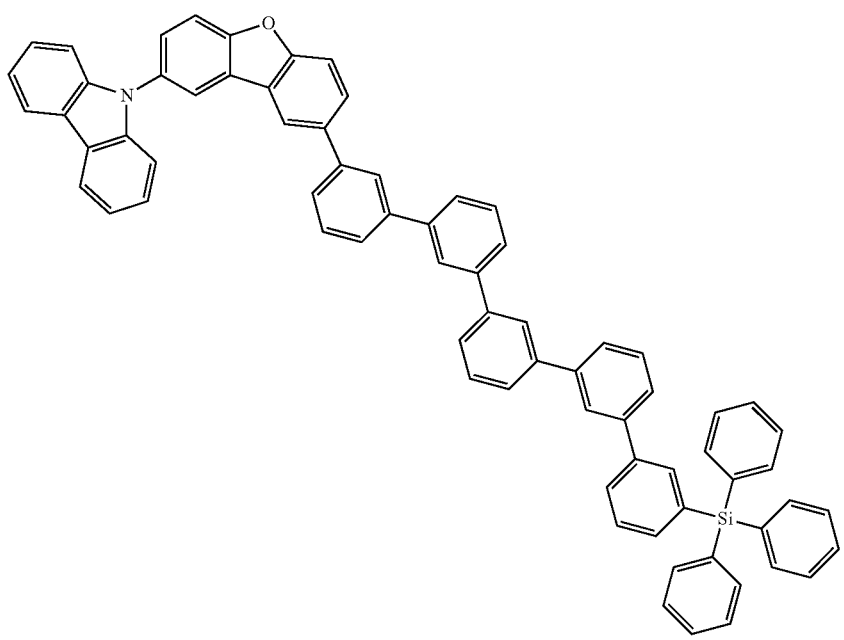
SH-11
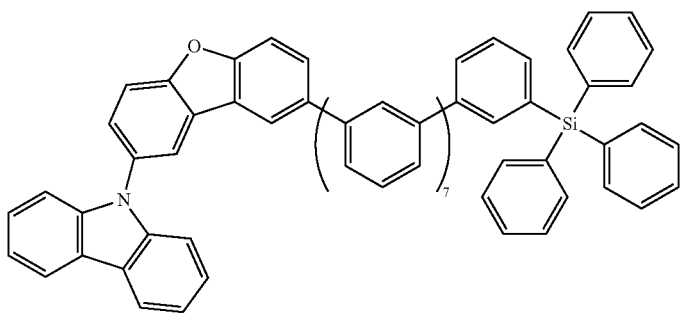

-continued
SH-12
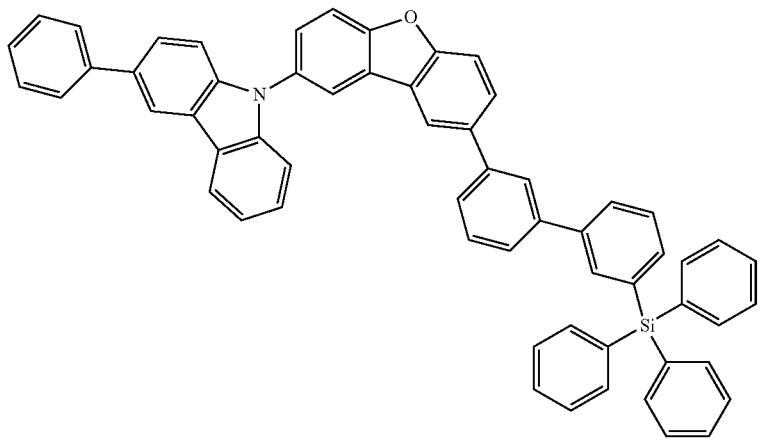
SH-13
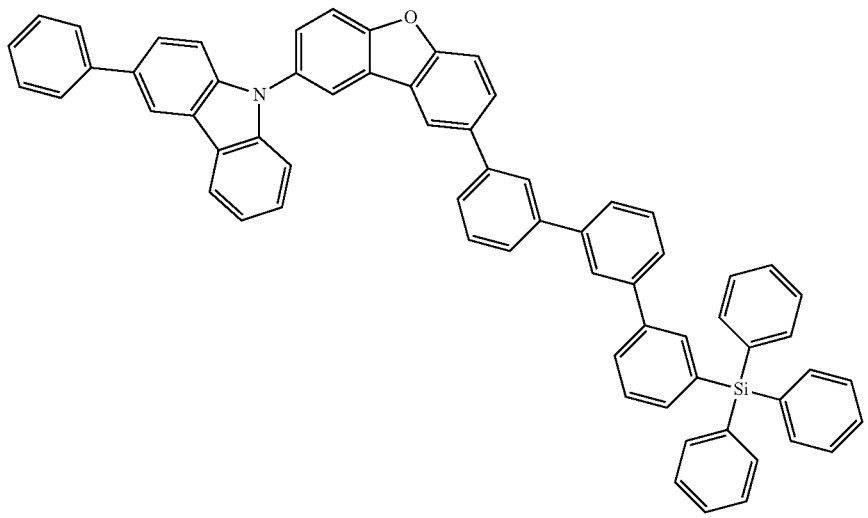
SH-14
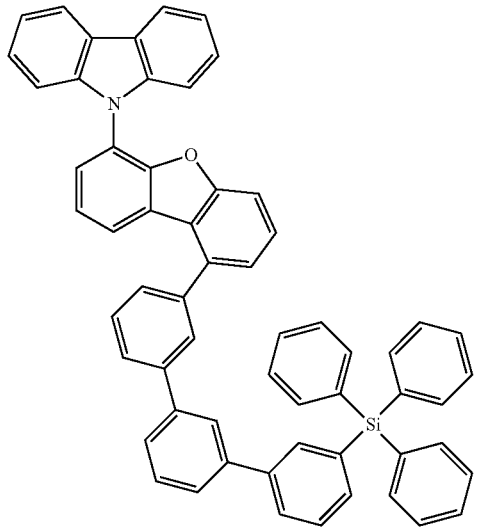

-continued
SH-15
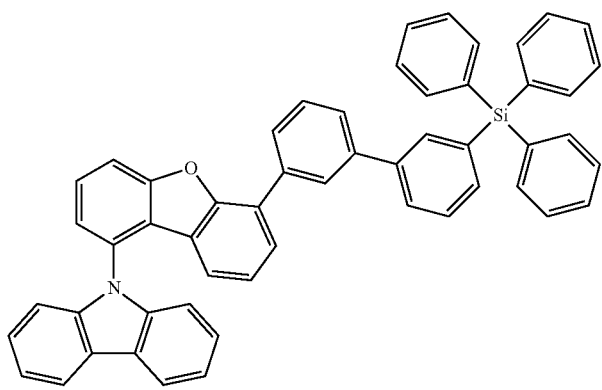
SH-16
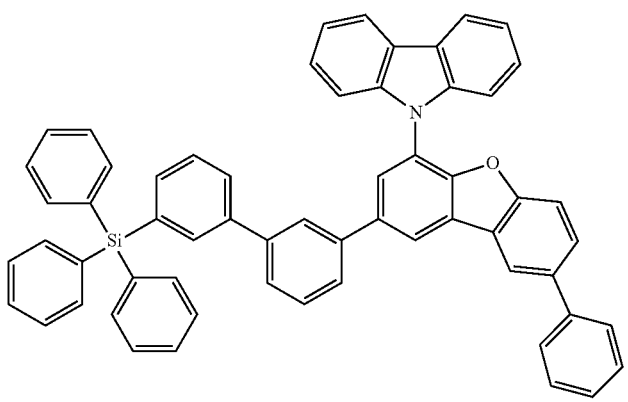
SH-17
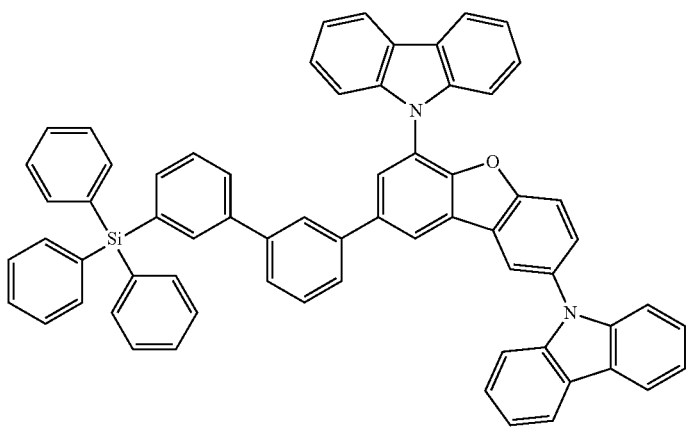
SH-18
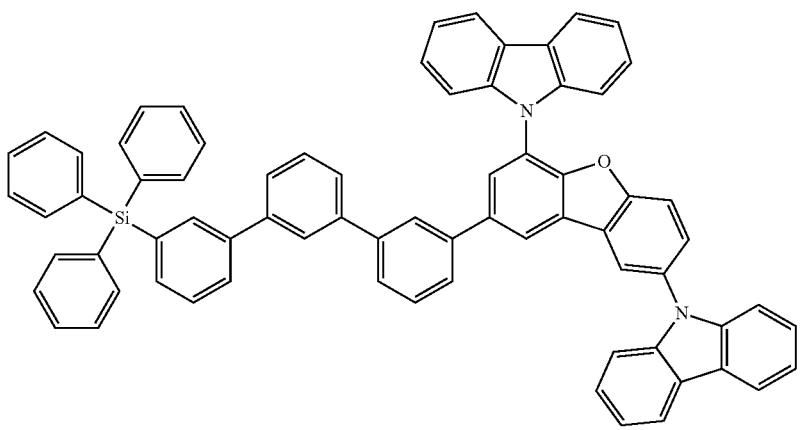

SH-19
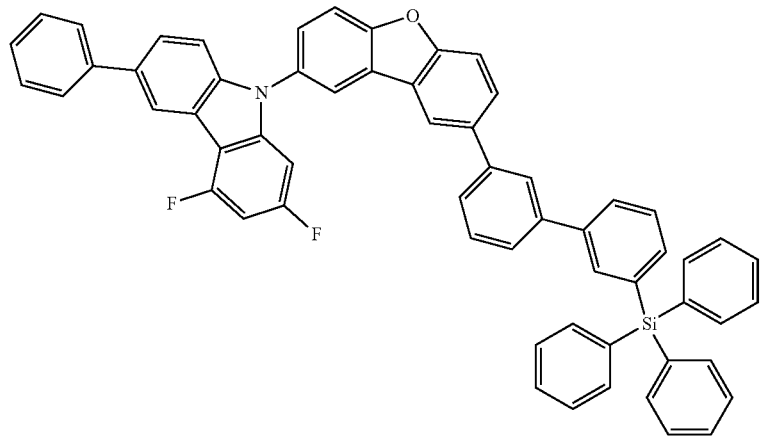
SH-20
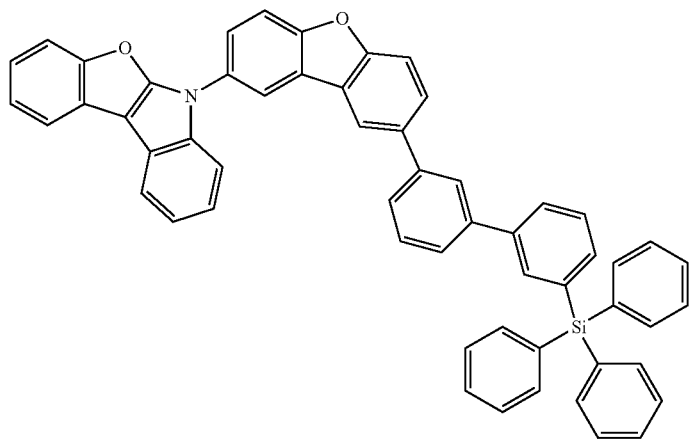
SH-21
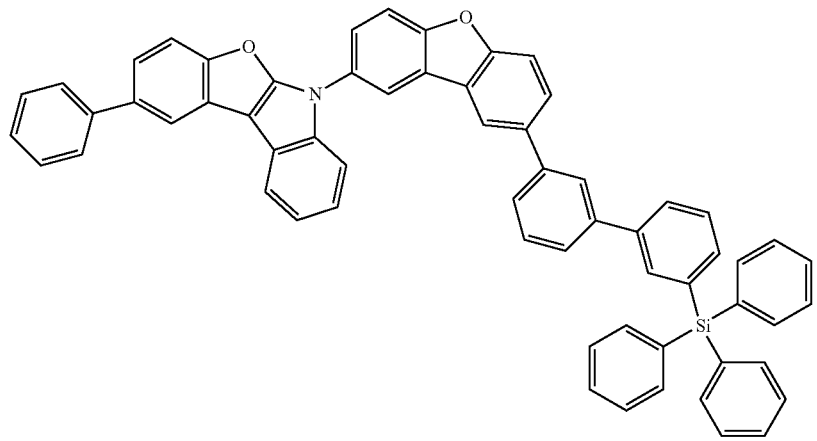

-continued
SH-22
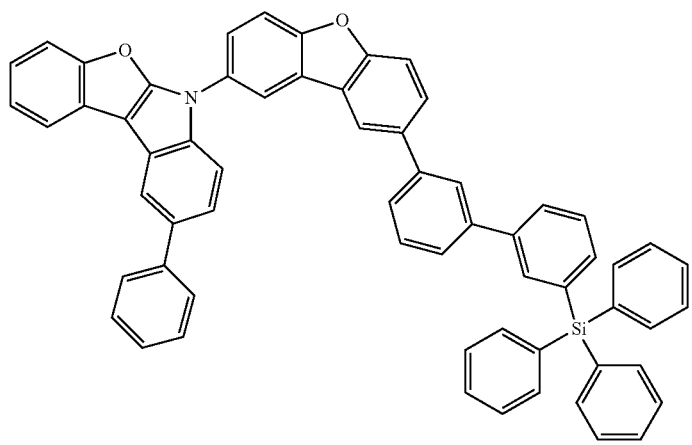
SH-23
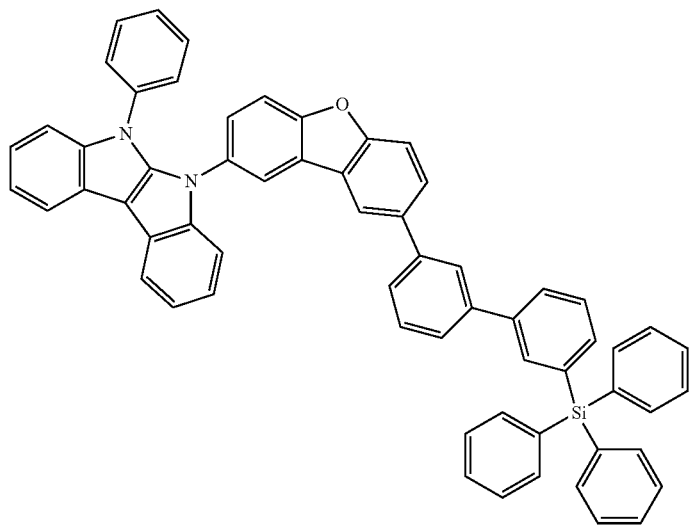
SH-24
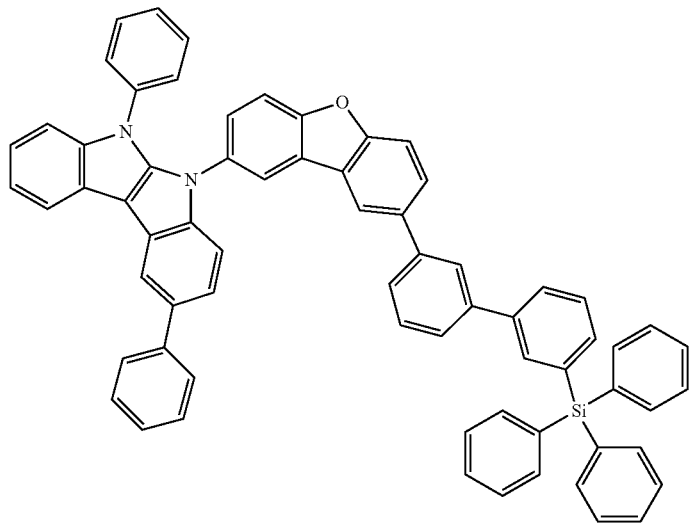

-continued
SH-25
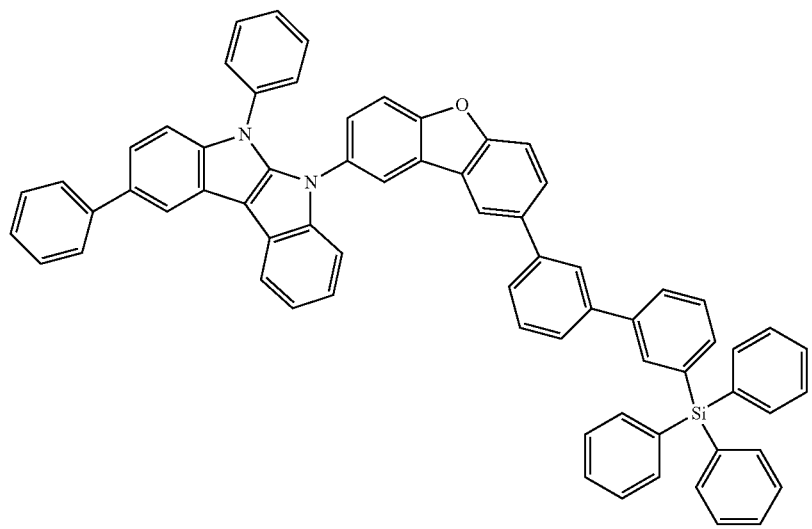
SH-26
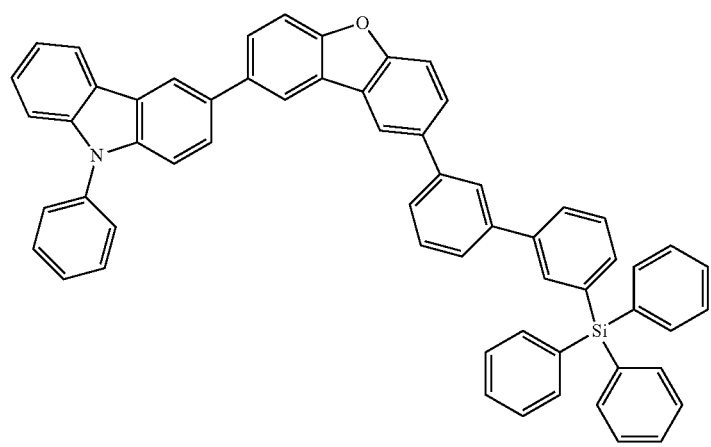
SH-27
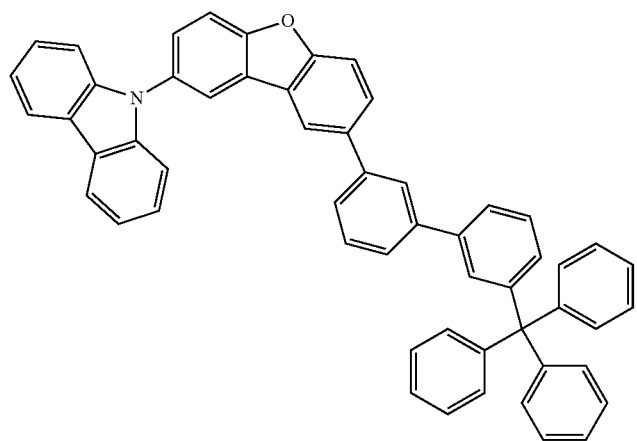

-continued
SH-28
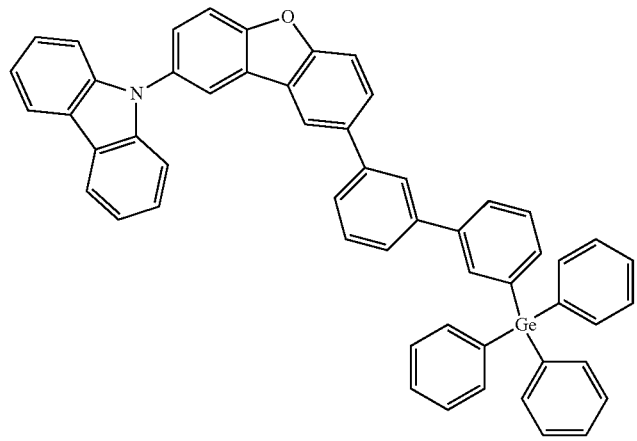
SH-29
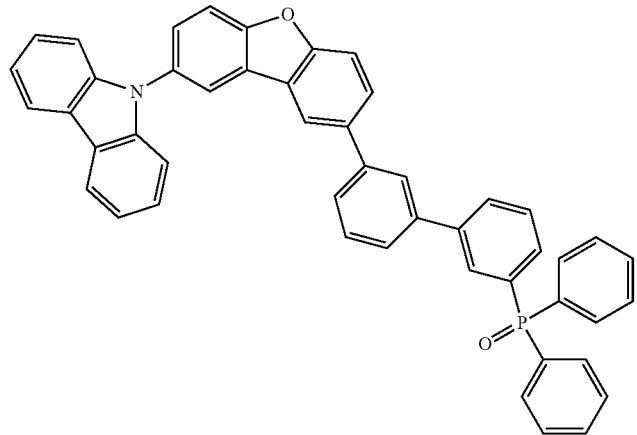
SH-30
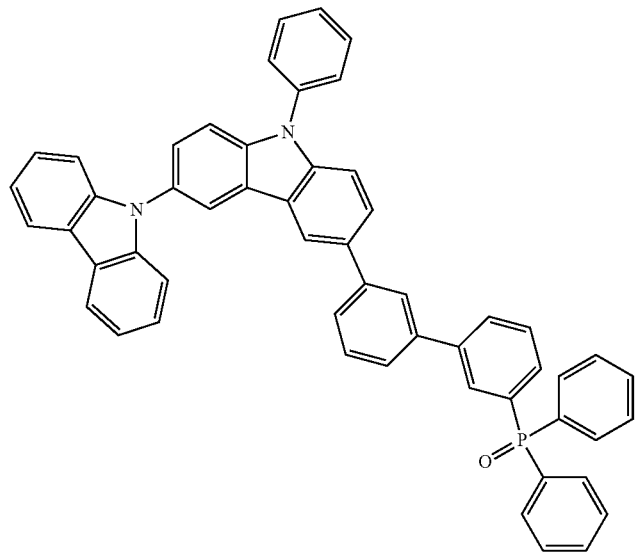

SH-31
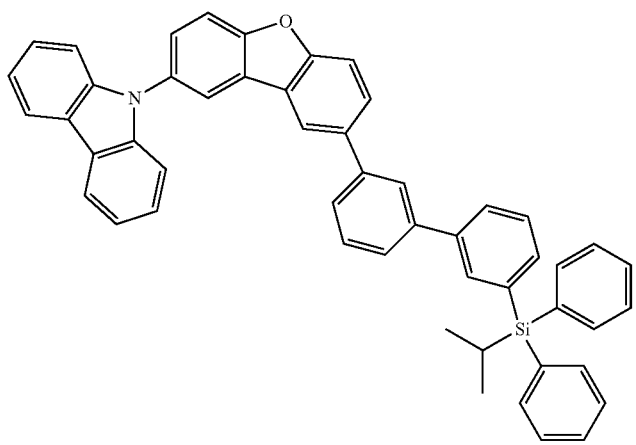
SH-32
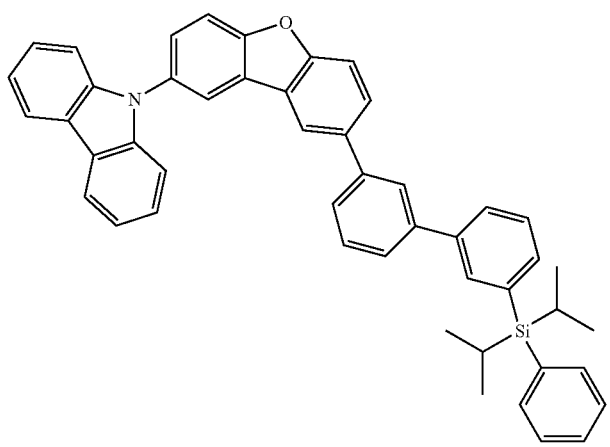
SH-33
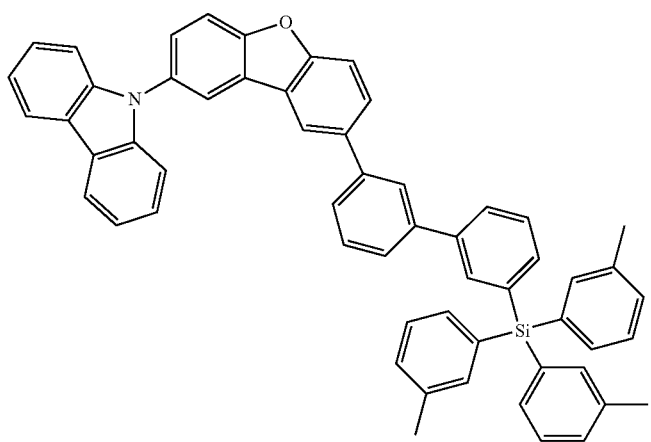

-continued
SH-34
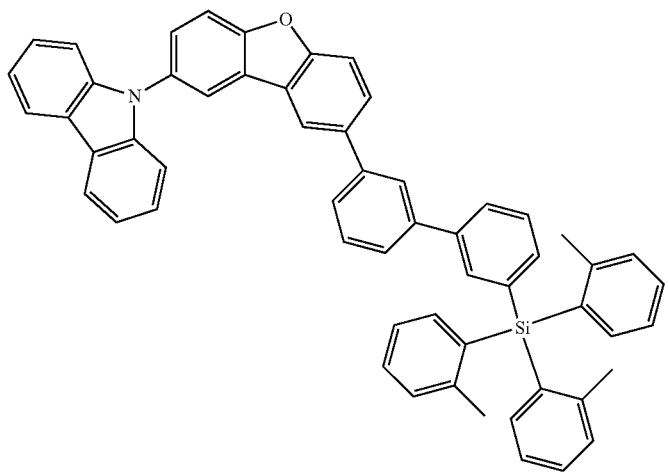
SH-35
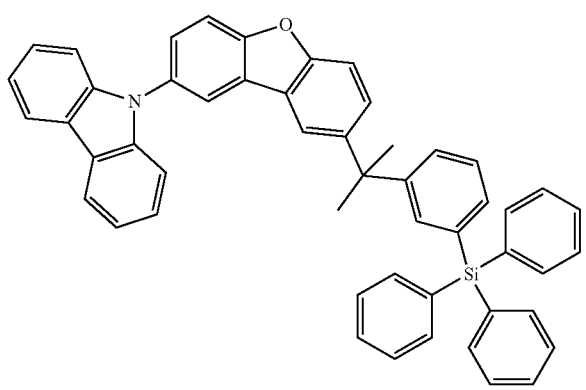
SH-36
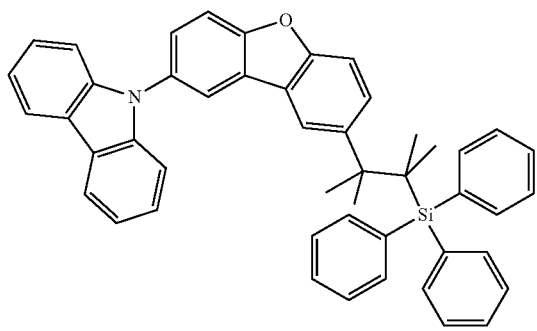
SH-37
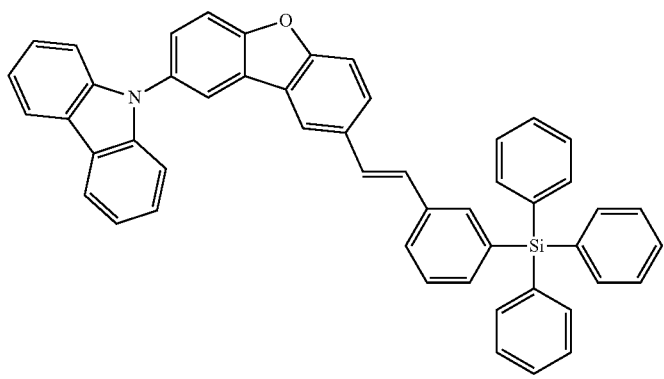

-continued
SH-38
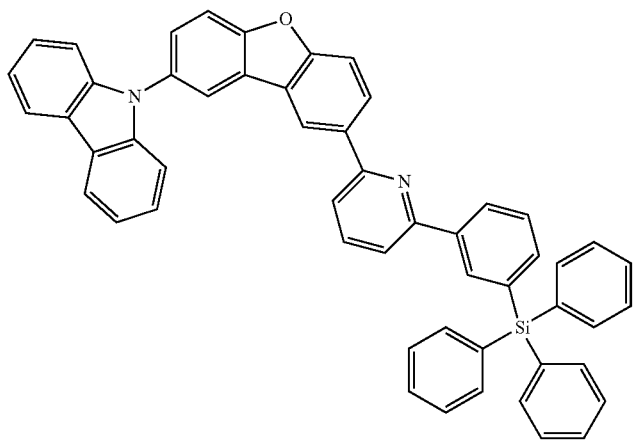
SH-39
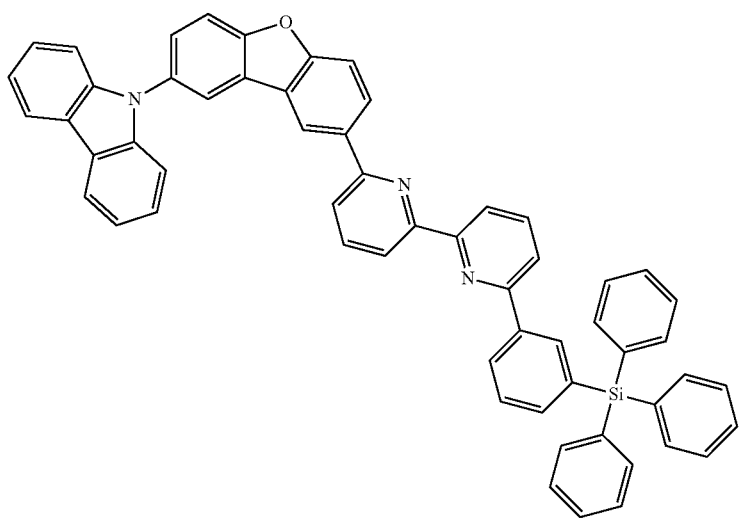
SH-40
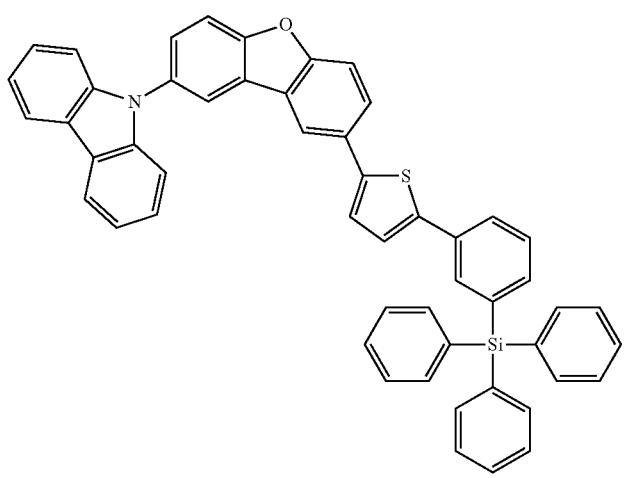

-continued
SH-41
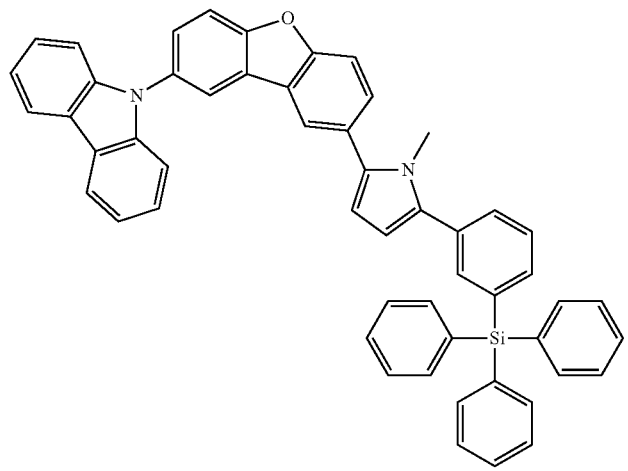
SH-42
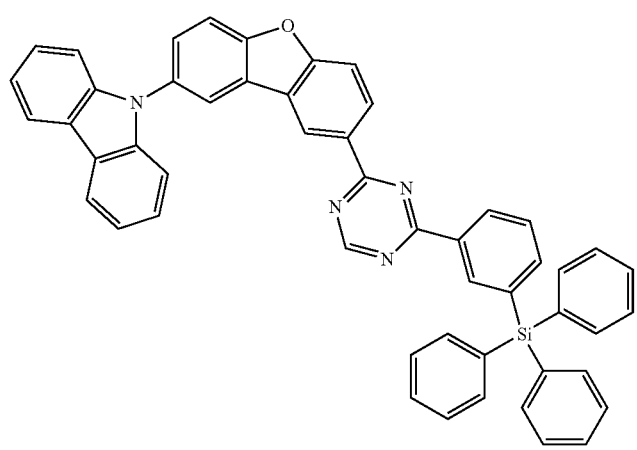
SH-43
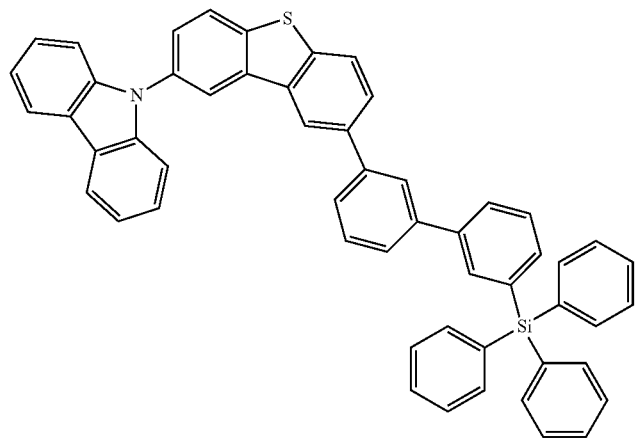

-continued
SH-44
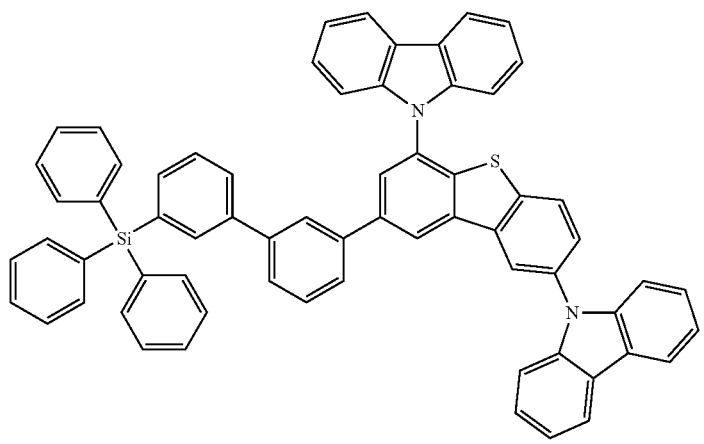
SH-45
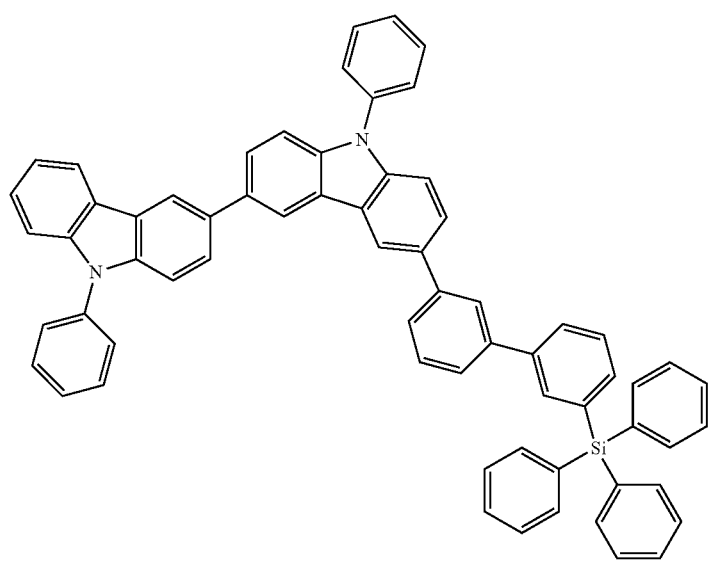
SH-46
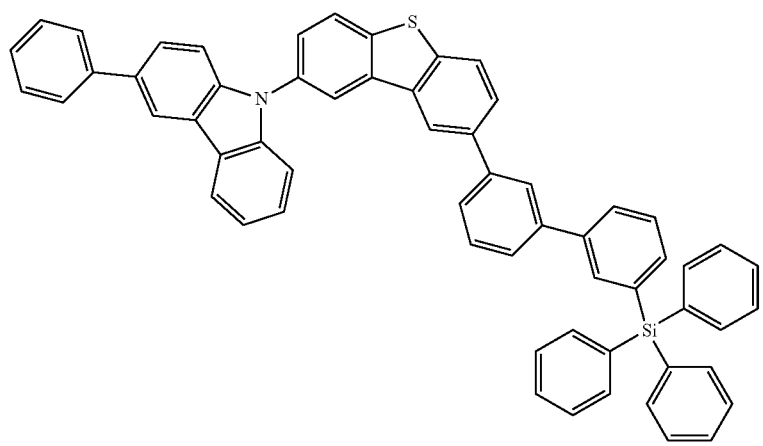

SH-47
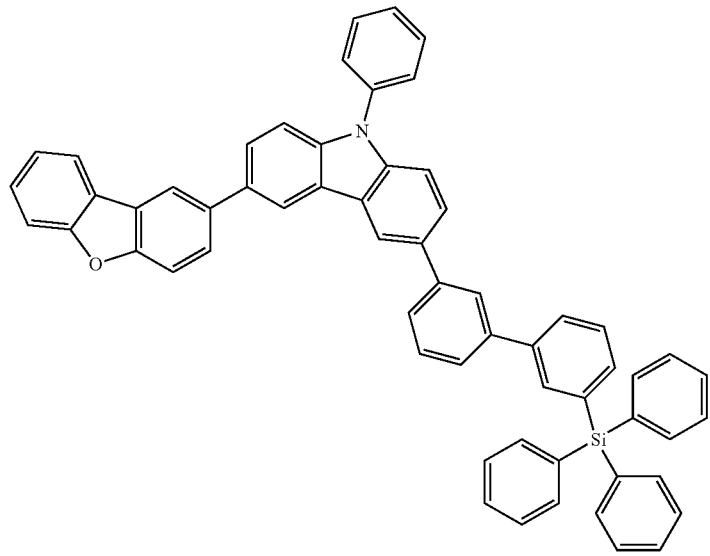
SH-48
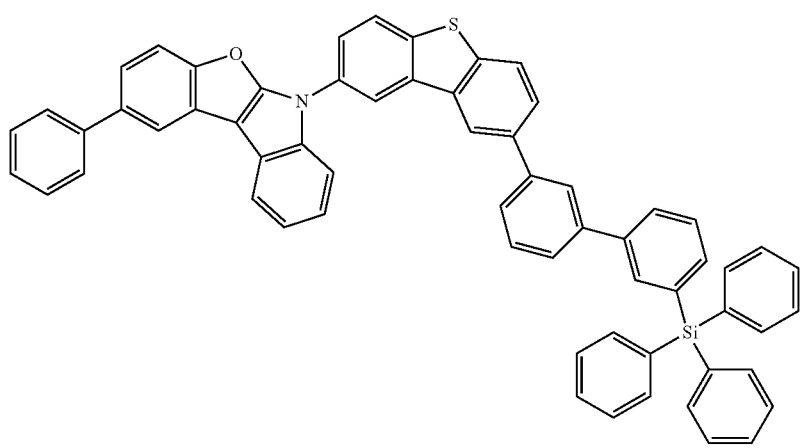
SH-49
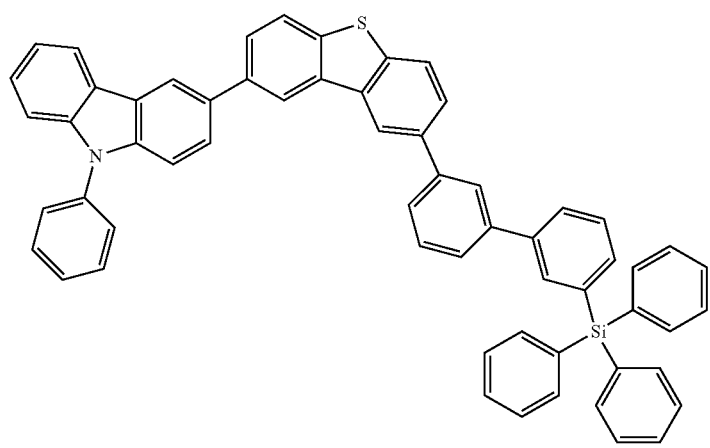

-continued
SH-50
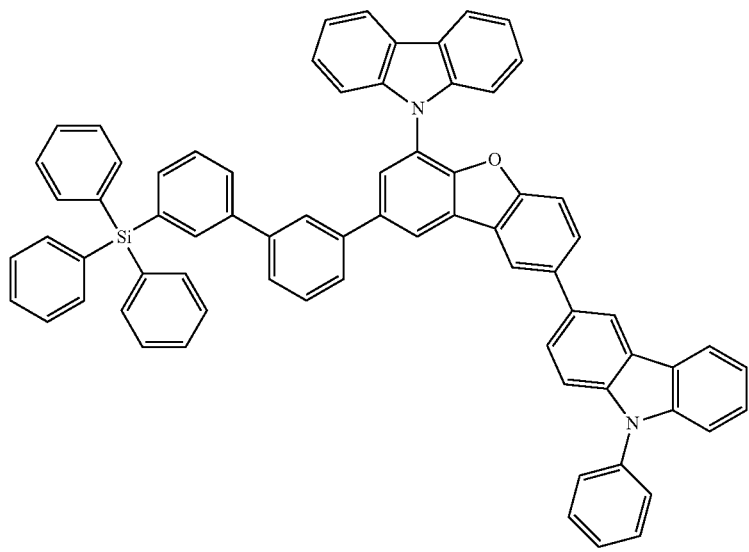
SH-51
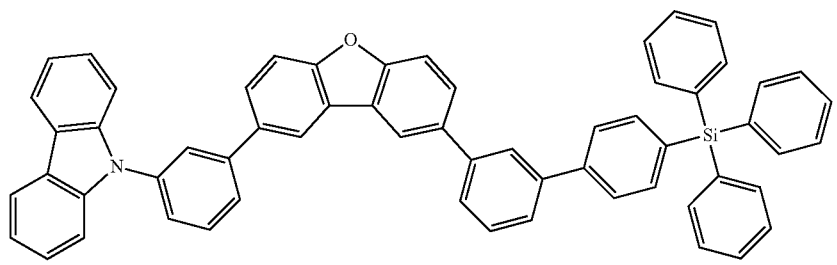
SH-52
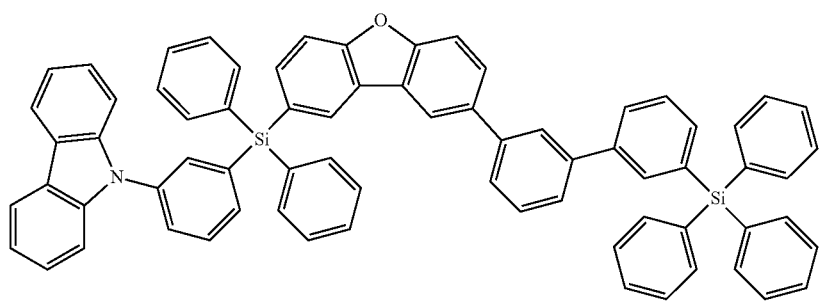

SH-53
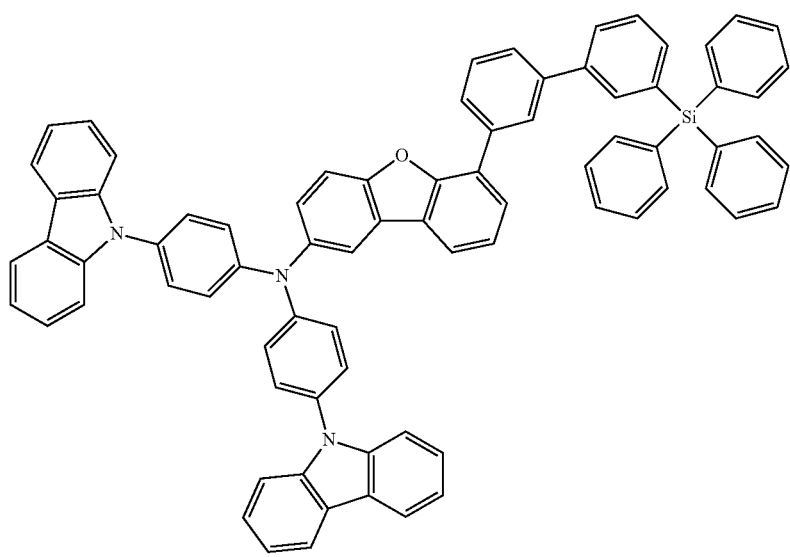
SH-54
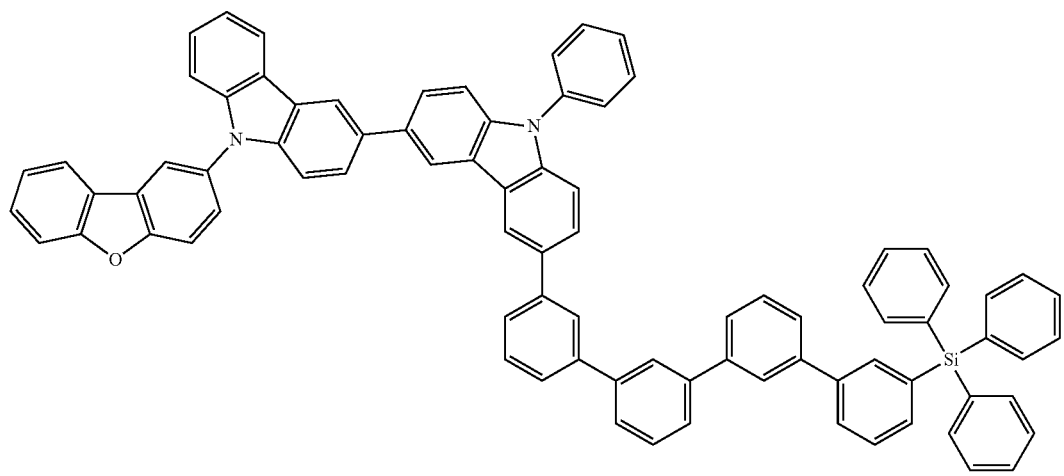
SH-55
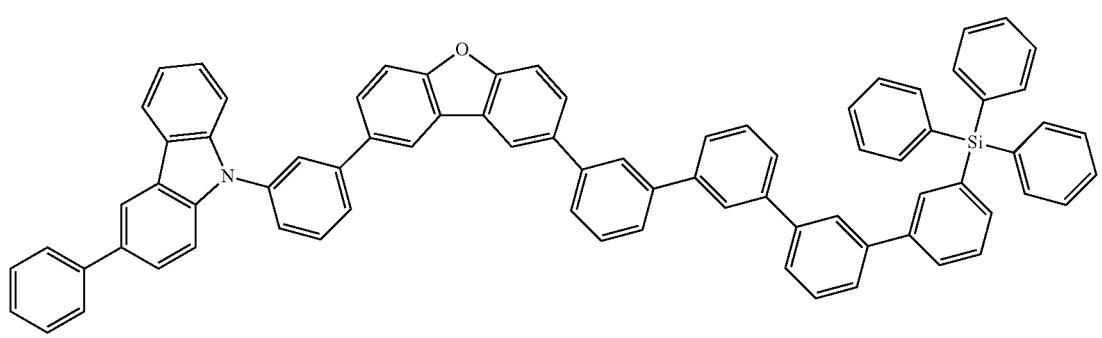

-continued
SH-56
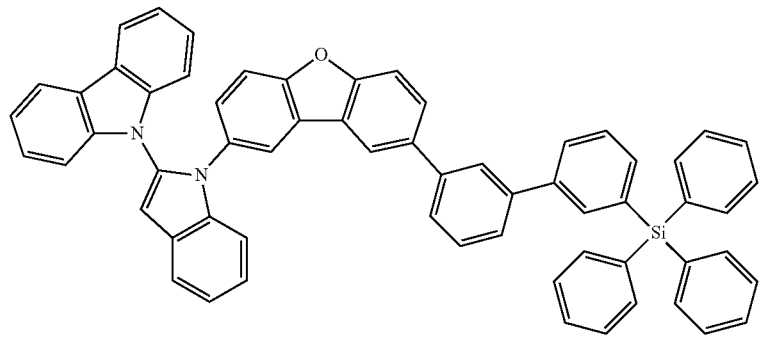
SH-57
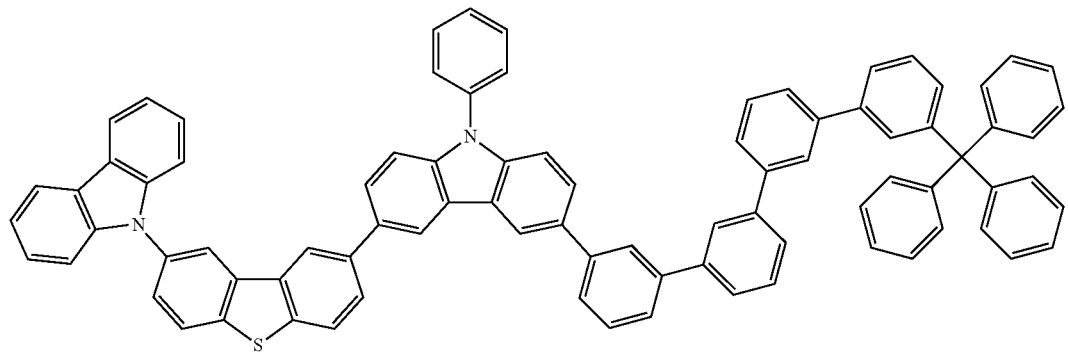
SH-58
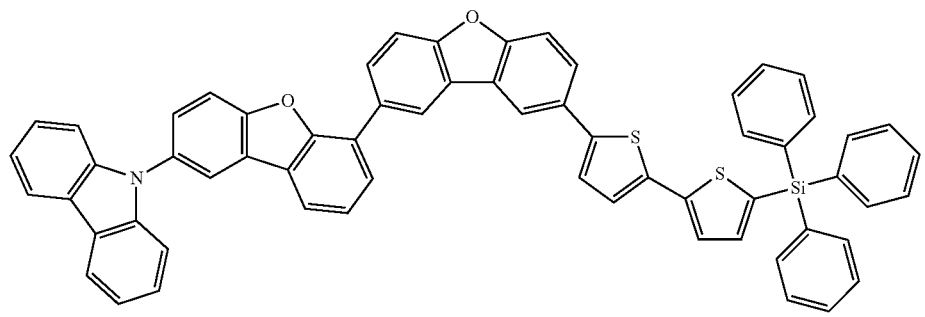
SH-59
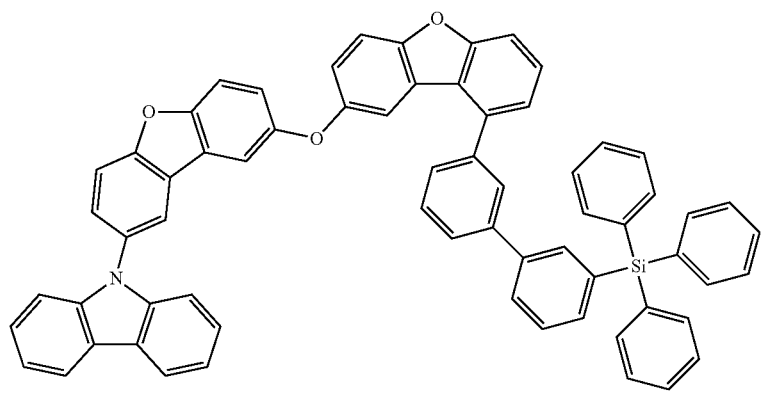

-continued
SH-60
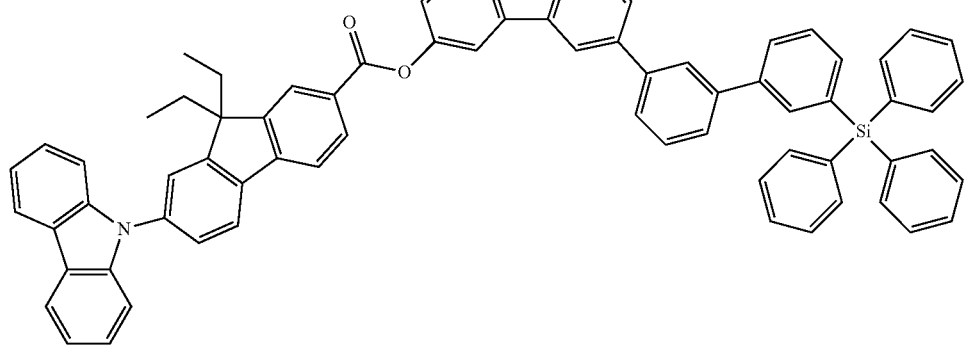
SH-61
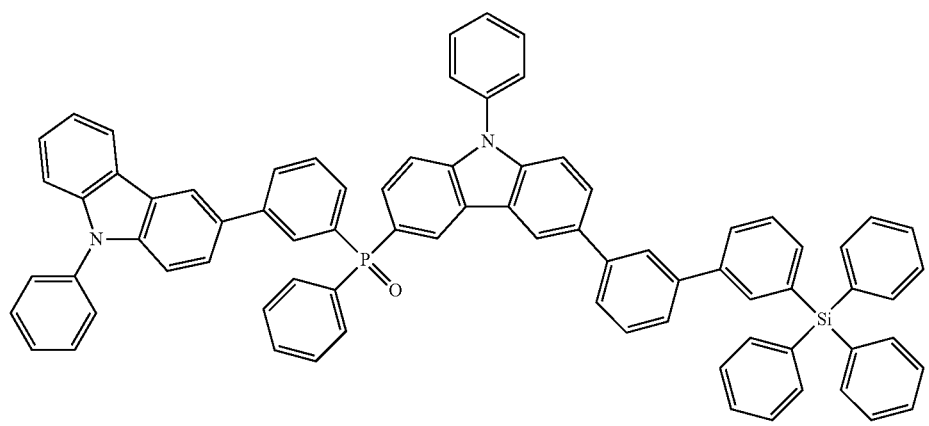
SH-62
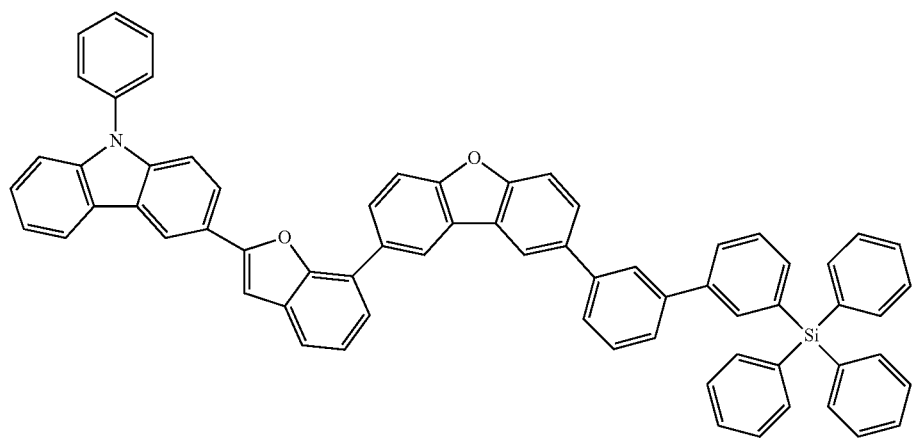
SH-63
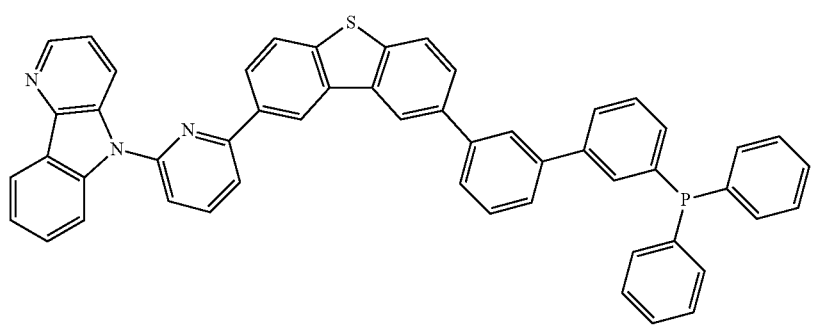

-continued
SH-64
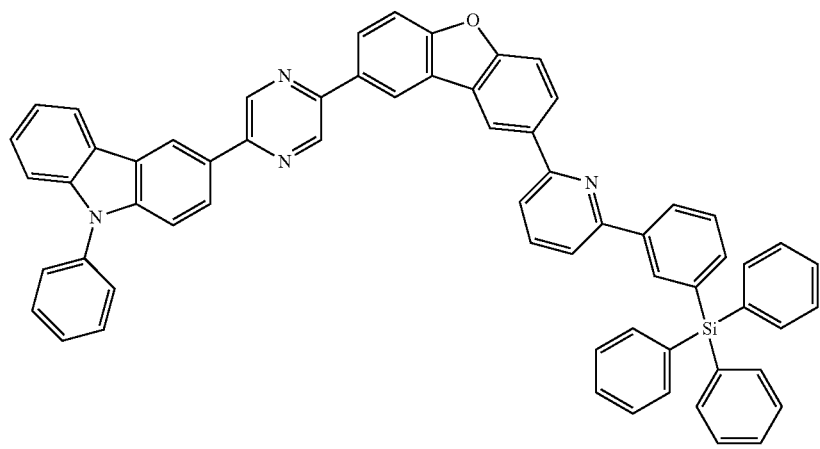
SH-65
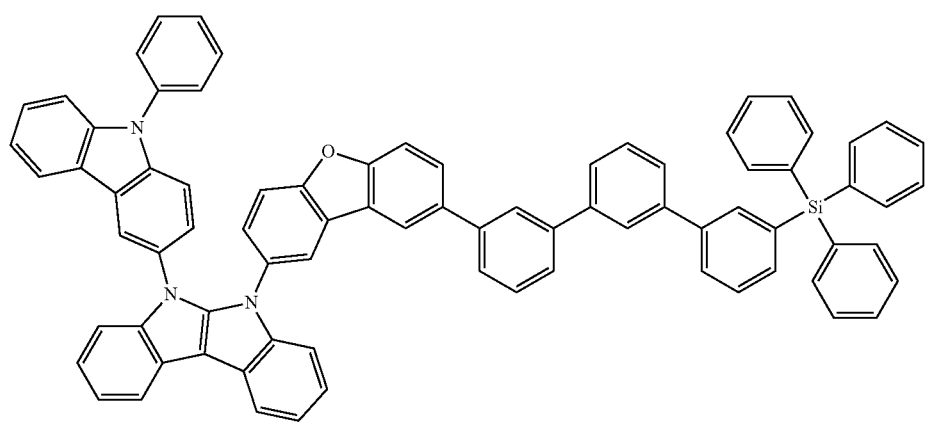
SH-66
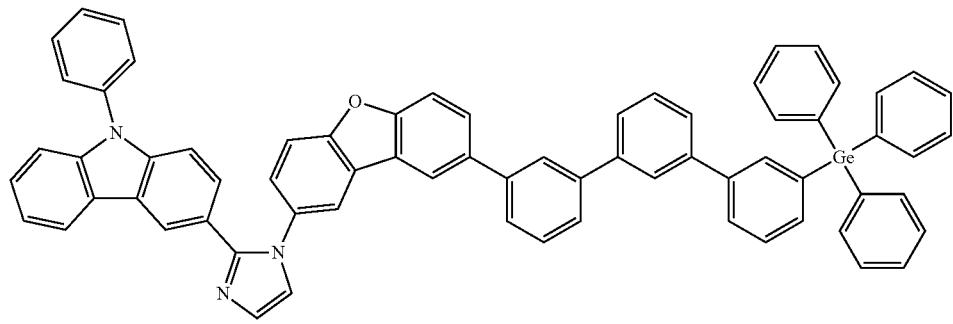
SH-67
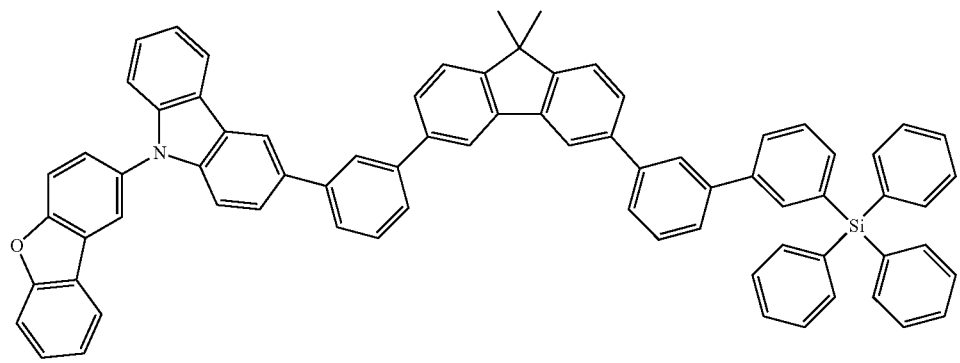

-continued
SH-68
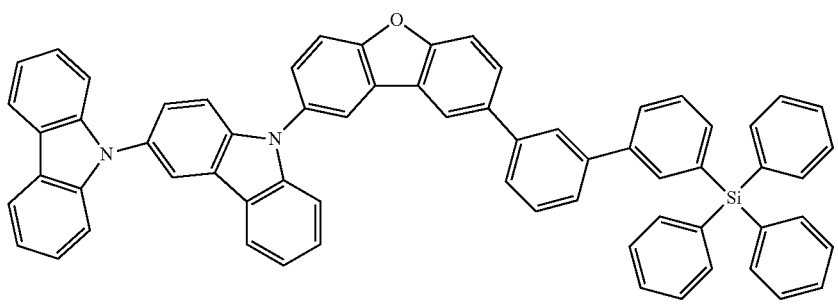
SH-69
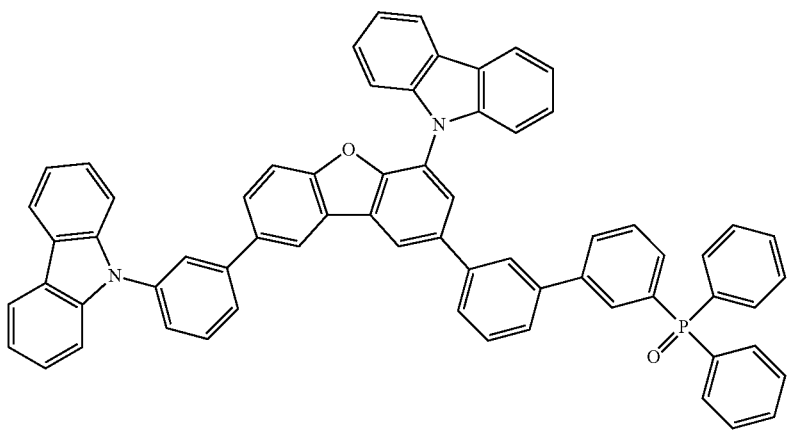
SH-70
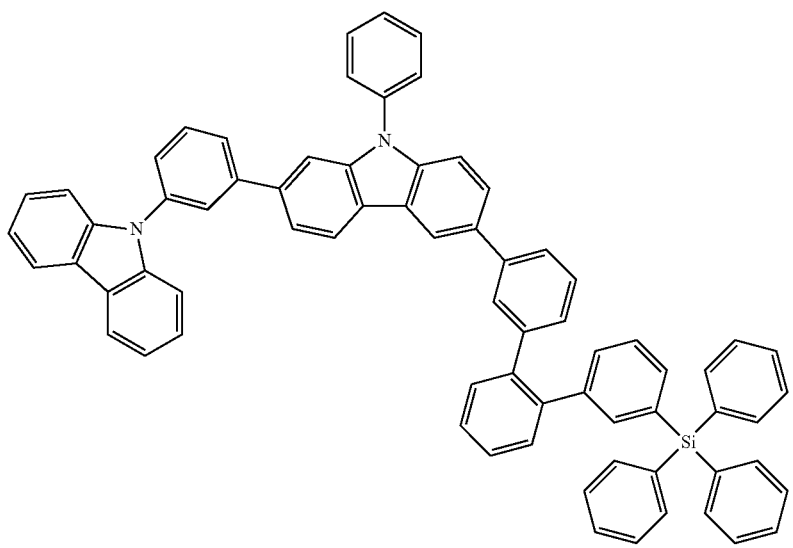

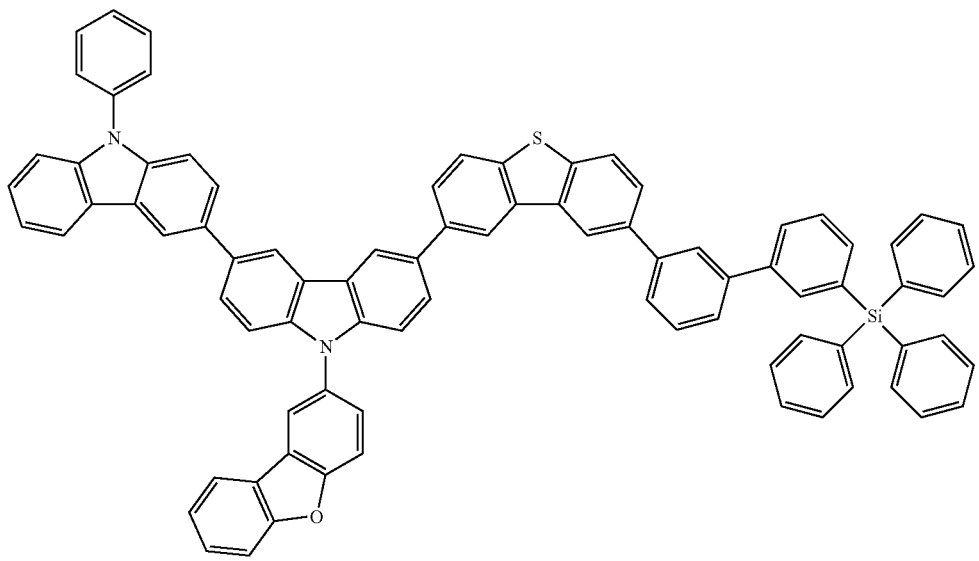
SH-71
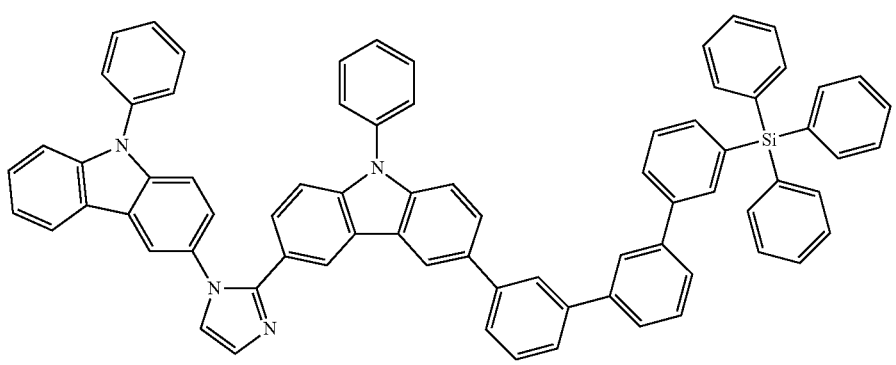
SH-72
Synthetic Example
A synthetic example of a compound represented by Formulas (1), (2) or (4) will be described in the following. However, the present invention will not be limited to this.
Among specific examples as described above, a synthetic example of SH-1 will be described as an example.
SH-1 can be synthesized according to the following scheme.
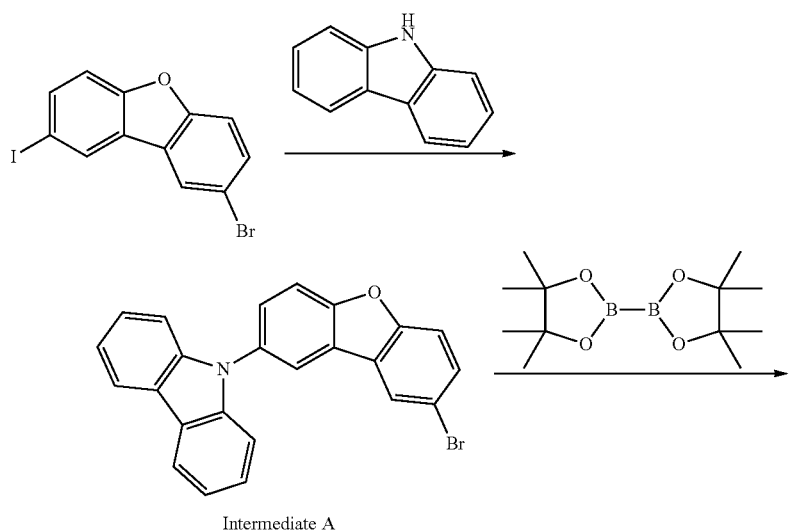
Intermediate A

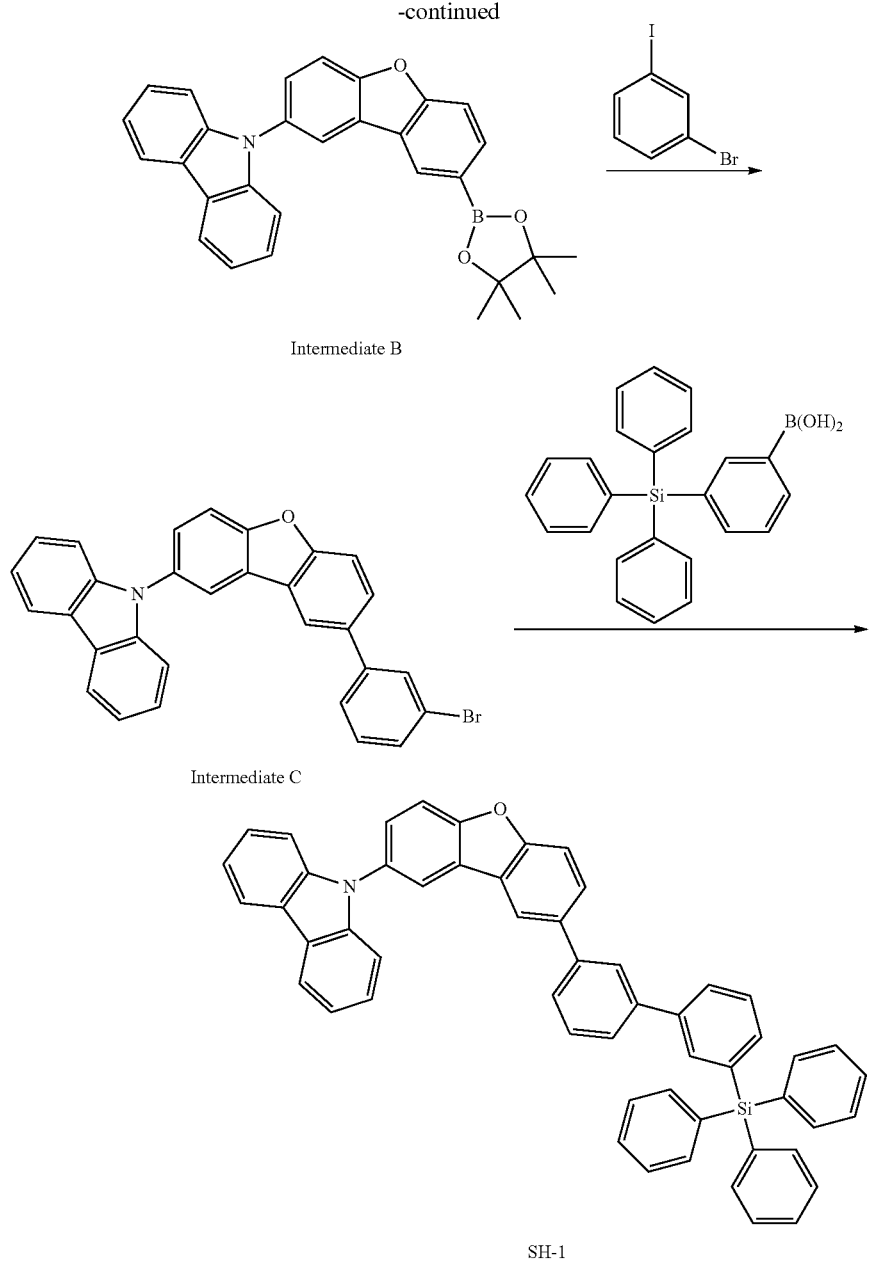

Intermediate B

Intermediate C

SH-1

In a 200 ml four-necked flask were placed 11.0 g of 2-bromo-8-iododibenzofuran, 4.9 g of carbazole, 5.6 g of copper powder, 6.1 g of potassium carbonate and 100 ml of dimethyl acetamide. A nitrogen gas introducing tube, a thermometer and a condenser were attached to the flask and it was set on an oil bath stirrer. Under the nitrogen gas flow, the mixture was heated to reflux at an inner temperature of about 130° C. for 36 hours to complete the reaction.

After completion of the reaction, the reaction mixture was cooled to a room temperature, then, tetrahydrofuran was added. After removing an insoluble substance and a residual component with a short column, the obtained solution was condensed under a reduced pressure until the amount of dimethyl acetamide became about 50 ml. Ethanol was added to the residue and the precipitated crystal was collected with a filter. The obtained solid was recrystallized with toluene to obtain 5.6 g (45.6%) of an intermediate A.

In a 100 ml four-necked flask were placed 5.6 g of the intermediate A, 4.6 g of bispinacolate diboron, 0.53 g of PdCl2 (dppf), 3.9 g of potassium acetate, and 50 ml of dimethyl acetamide. A nitrogen gas introducing tube, a thermometer and a condenser were attached to the flask and it was set on an oil bath stirrer. Under the nitrogen gas flow, the mixture was heated to reflux at an inner temperature of about 90° C. for 48 hours to complete the reaction.

After completion of the reaction, the reaction mixture was poured into toluene. After filtering an insoluble substance, the toluene solution was washed with city water, then, with salt water. Subsequently, it was dried with magnesium sulfate. After purifying that solution with a short column, it was recrystallized with heptane to obtain 4.9 g (78.8%) of an intermediate B.

In a 100 ml four-necked flask were placed 4.9 g of the intermediate B, 6.0 g of 1,3-iodobromobenzene, 0.25 g of tetrakis(triphenylphosphine) palladium, 100 ml of dimethoxy ethane, and 15 ml of 2M aqueous sodium carbonate solution. A nitrogen gas introducing tube, a thermometer and a condenser were attached to the flask and it was set on an oil bath stirrer. Under the nitrogen gas flow, the mixture was heated to reflux at an inner temperature of about 75° C. for 14 hours to complete the reaction.

After completion of the reaction, the reaction mixture was extracted with toluene. Then, toluene solution was condensed under a reduced pressure. The obtained residue was purified with a silica gel column chromatography to obtain 3.3 g (64.2%) of an intermediate C.

In a 100 ml four-necked flask were placed 3.3 g of the intermediate C, 3.1 g of [3-(triphenylsiliy)phenyl]boronic acid, 0.16 g of tetrakis(triphenylphosphine) palladium, 50 ml of dioxane, and 9 ml of 2M aqueous sodium carbonate solution. A nitrogen gas introducing tube, a thermometer and a condenser were attached to the flask and it was set on an oil bath stirrer. Under the nitrogen gas flow, the mixture was heated to reflux at an inner temperature of about 80° C. for 15 hours to complete the reaction.

After completion of the reaction, the reaction mixture was cooled to a room temperature. Then it was poured into city water. The precipitated crystal was collected with a filter. The obtained crystal was purified with a silica gel column chromatography. Subsequently, it was recrystallized with heptane to obtain 3.7 g (73.2%) of SH-1. The structure of SH-1 was confirmed with mass spectroscopy and $^1$H-NMR.

MASS Spectrum (ESI): m/z=744 (M+)

$^1$H-NMR (THF-d8, 400 MHz): δ 8.14 ($^1$H, d), δ 8.01 ($^1$H, d), δ 7.78 ($^1$H, d), δ 7.25-7.74 (34H, m)

It is preferable that the compounds represented by Formulas (1), (2) and (4) are used for a hole blocking material, an electron blocking material and a host. More preferably, they are used for a host.

In addition, known hosts described later can be used in combination therewith.

<<Constitution Layers of Organic EL Element>>

Constitution layers of an organic EL element of the present invention will be described. Representative element constitutions used for an organic EL element of the present invention are as follows, however, the present invention is not limited to these.

(i) Anode/light emitting layer/cathode
(ii) Anode/light emitting layer/electron transport layer/cathode
(iii) Anode/hole transport layer/light emitting layer/cathode
(iv) Anode/hole transport layer/light emitting layer/electron transport layer/cathode
(v) Anode/hole transport layer/light emitting layer/electron transport layer/electron injection layer/cathode
(vi) Anode/hole injection layer/hole transport layer/light emitting layer/electron transport layer/cathode
(vii) Anode/hole injection layer/hole transport layer/(electron blocking layer)/light emitting layer/(hole blocking layer)/electron transport layer/electron injection layer/cathode Among these, the embodiment (vii) is preferably used. However, the present invention is not limited to this.

According to necessity, it may be provided with a hole blocking layer (it is also called as a hole barrier layer) or an electron injection layer (it is also called as a cathode buffer layer) between the light emitting layer and the cathode. Further, it may be provided with an electron blocking layer (it is also called as an electron barrier layer) or an hole injection layer (it is also called as an anode buffer layer) between the light emitting layer and the anode.

An electron transport layer according to the present invention is a layer having a function of transporting an electron. An electron transport layer includes an electron injection layer, and a hole blocking layer in a broad sense. Further, an electron transport layer unit may be composed of plural layers.

A hole transport layer according to the present invention is a layer having a function of transporting a hole. A hole transport layer includes a hole injection layer, and an electron blocking layer in a broad sense. Further, a hole transport layer unit may be composed of plural layers.

In the representative element constitutions as described above, the layers eliminating an anode and a cathode are also called as "organic layers".

(Tandem Structure)

An organic EL element according to the present invention may be so-called a tandem structure element in which plural light emitting units each containing at least one light emitting are laminated.

A representative example of an element constitution having a tandem structure is as follows.

Anode/first light emitting unit/intermediate layer/second light emitting unit/intermediate layer/third light emitting unit/cathode Here, the above-described first light emitting unit, second light emitting unit, and third light emitting unit may be the same or different. It may be possible that two light emitting units are the same and the remaining one light emitting unit is different.

The plural light emitting units each may be laminated directly or they may be laminated through an intermediate layer. Examples of an intermediate layer are: an intermediate electrode, an intermediate conductive layer, a charge generating layer, an electron extraction layer, a connecting layer, and an intermediate insulating layer. Known composing materials may be used as long as it can form a layer which has a function of supplying an electron to an adjacent layer to the anode, and a hole to an adjacent layer to the cathode.

Examples of a material used in an intermediate layer are: conductive inorganic compounds such as ITO (indium tin oxide), IZO (indium zinc oxide), $ZnO_2$, TiN, ZrN, HfN, $TiO_X$, $VO_X$, CuI, InN, GaN, $CuAlO_2$, $CuGaO_2$, $SrCu_2O_2$, $LaB_6$, $RuO_2$, and Al; a two-layer film such as $Au/Bi_2O_3$; a multi-layer film such as $SnO_2/Ag/SnO_2$, $ZnO/Ag/ZnO$, $Bi_2O_3/Au/Bi_2O_3$, $TiO_2/TiN/TiO_2$, and $TiO_2/ZrN/TiO_2$; fullerene such as $C_{60}$; and a conductive organic layer such as oligothiophene, metal phthalocyanine, metal-free phthalocyanine, metal porphyrin, and metal-free porphyrin. The present invention is not limited to them.

Examples of a preferable constitution in the light emitting unit are the constitutions of the above-described (i) to (vii) from which an anode and a cathode are removed. However, the present invention is not limited to them.

Examples of a tandem type organic EL element are described in: U.S. Pat. No. 6,337,492, U.S. Pat. No. 7,420,203, U.S. Pat. No. 7,473,923, U.S. Pat. No. 6,872,472, U.S. Pat. No. 6,107,734, U.S. Pat. No. 6,337,492, WO 2005/009087, JP-A 2006-228712, JP-A 2006-24791, JP-A 2006-49393, JP-A 2006-49394, JP-A 2006-49396, JP-A 2011-96679, JP-A 2005-340187, JP Patent 4711424, JP Patent 3496681, JP Patent 3884564, JP Patent 4213169, JP-A 2010-192719, JP-A 2009-076929, JP-A 2008-078414, JP-A 2007-059848, JP-A 2003-272860, JP-A 2003-045676, and WO 2005/094130. The constitutions of the elements and the composing materials are described in these documents, however, the present invention is not limited to them.

Each layer that constitutes an organic EL element of the present invention will be described in the following.

<<Light Emitting Layer>>

A light emitting layer relating to the present invention is a layer which provide a place of emitting light via an exciton produce by recombination of electrons and holes injected from an electrode or an adjacent layer. The light emitting portion may be either within the light emitting layer or at an interface between the light emitting layer and an adjacent layer thereof.

A total thickness of the light emitting layer is not particularly limited. However, in view of layer homogeneity, required voltage during light emission, and stability of the emitted light color against a drive electric current, a layer thickness is preferably adjusted to be in the range of 2 nm to 5 μm, more preferably, it is in the range of 2 nm to 500 nm, and still most preferably, it is in the range of 5 nm to 200 nm.

Each light emitting layer is preferably adjusted to be in the range of 2 nm to 1 μm, more preferably, it is in the range of 2 nm to 200 nm, and still most preferably, it is in the range of 3 nm to 150 nm.

It is preferable that the light emitting layer of the present invention incorporates a light emitting dopant (a light emitting dopant compound, a dopant compound, or simply called as a dopant) and a host compound (a matrix material, a light emitting host compound, or simply called as a host).

<<Light Emitting Dopant>>

A light emitting dopant according to the present invention will be described.

As a light emitting dopant, it is preferable to employ: a fluorescence emitting dopant (also referred to as a fluorescent dopant and a fluorescent compound) and a phosphorescence emitting dopant (also referred to as a phosphorescent dopant and a phosphorescent emitting material). In the present invention, it is preferable that at least one light emitting layer contains a phosphorescence emitting dopant.

A concentration of a light emitting dopant in a light emitting layer may be arbitrarily decided based on the specific dopant employed and the required conditions of the device. A concentration of a light emitting dopant may be uniform in a thickness direction of the light emitting layer, or it may have any concentration distribution.

It may be used plural light emitting dopants according to the present invention. It may use a combination of dopants each having a different structure, or a combination of a fluorescence emitting dopant and a phosphorescence emitting dopant. Any required emission color will be obtained by this.

Figure 4:
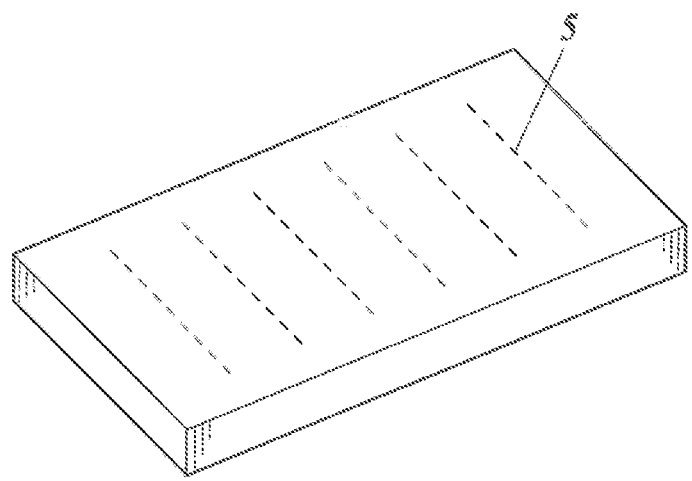
FIG. 4 is a schematic drawing of a full color display device according to a passive matrix mode.
Figure 4:
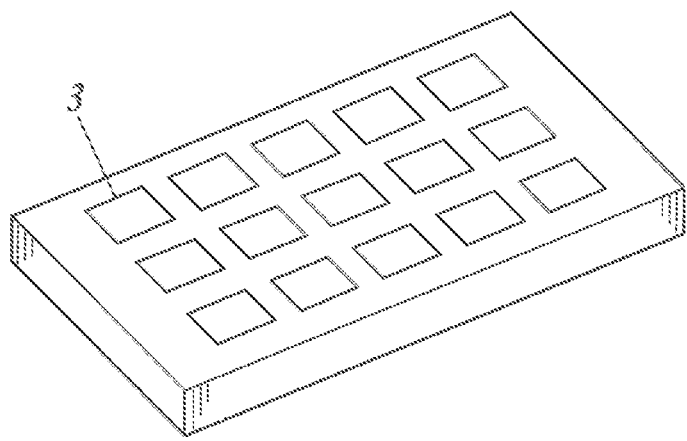
Figure 4:
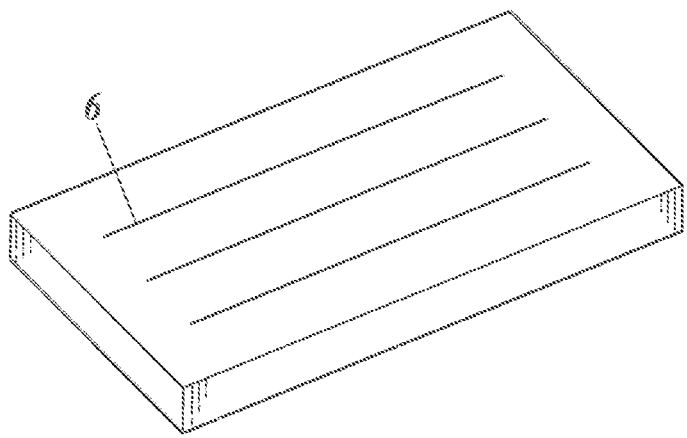

Color of light emitted by an organic EL element or a compound of the present invention is specified as follows. In FIG. 4.16 on page 108 of "Shinpen Shikisai Kagaku Handbook (New Edition Color Science Handbook)" (edited by The Color Science Association of Japan, Tokyo Daigaku Shuppan Kai, 1985), values determined via a spectroradiometric luminance meter CS-1000 (produced by Konica Minolta, Inc.) are applied to the CIE chromaticity coordinate, whereby the color is specified.

In the present invention, it is preferable that the organic EL element of the present invention exhibits white emission by incorporating one or plural light emitting layers containing plural emission dopants having different emission colors.

The combination of emission dopants producing white is not specifically limited. It may be cited, for example, combinations of: blue and orange; and blue, green and red.

It is preferable that "white" in the organic EL element of the present invention shows chromaticity in the CIE 1931 Color Specification System at 1,000 cd/m$^2$ in the region of x=0.39±0.09 and y=0.38±0.08, when measurement is done to 2-degree viewing angle front luminance via the aforesaid method.

(1.1) Fluorescence Emitting Dopant

A fluorescence emitting dopant (hereafter, it is also called as "a fluorescence dopant") according to the present invention will be described.

A fluorescence emitting dopant according to the present invention is a compound which is capable of emitting light from an excited singlet. It is not specifically limited as long as an emission from an excited singlet is observed.

As fluorescence emitting dopants, listed are compounds such as: an anthracene derivative, a pyrene derivative, a chrysene derivative, a fluoranthene derivative, a perylene derivative, a fluorene derivative, an arylacetylene derivative, a styrylarylene derivative, a styrylamine derivative, an arylamine derivative, a boron complex, a coumarin derivative, a pyran derivative, a cyanine derivative, a croconium derivative, a squarium derivative, an oxobenzanthracene derivative, a fluorescein derivative, a rhodamine derivative, a pyrylium derivative, a perylene derivative, a polythiophene derivative, and a rare earth complex compound.

In addition, it has been developed a light emitting dopant utilizing delayed fluorescence. It may be used a light emitting dopant utilizing this type of fluorescence.

Specific examples of utilizing delayed fluorescence are compounds described in: WO 2011/156793, JP-A 2011-213643, and JP-A 2010-93181. However, the present invention is not limited to them.

(1.2) Phosphorescence Emitting Dopant

A phosphorescence emitting dopant (hereafter, it is also called as "a phosphorescence dopant") according to the present invention will be described.

The phosphorescence emitting dopant is a compound which is observed emission from an excited triplet state thereof. Specifically, it is a compound which emits phosphorescence at room temperature (25° C.) and exhibits a phosphorescence quantum yield of at least 0.01 at 25° C. The phosphorescence quantum yield is preferably at least 0.1.

The phosphorescence quantum yield will be determined via a method described in page 398 of Bunko II of Dai 4 Han Jikken Kagaku Koza 7 (Spectroscopy II of 4th Edition Lecture of Experimental Chemistry 7) (1992, published by Maruzen Co. Ltd.). The phosphorescence quantum yield in a solution will be determined using appropriate solvents. However, it is only necessary for the phosphorescent dopant of the present invention to exhibit the above phosphorescence quantum yield (0.01 or more) using any of the appropriate solvents.

Two kinds of principles regarding emission of a phosphorescence emitting dopant are cited. One is an energy transfer-type, wherein carriers recombine on a host compound on which the carriers are transferred to produce an excited state of the host compound, and then, via transfer of this energy to a phosphorescent dopant, emission from the phosphorescence emitting dopant is realized. The other is a carrier trap-type, wherein a phosphorescence emitting dopant serves as a carrier trap and then carriers recombine on the phosphorescent dopant to generate emission from the phosphorescent dopant. In each case, the excited state energy of the phosphorescent dopant is required to be lower than that of the host compound.

A phosphorescence dopant may be suitably selected and employed from the known materials used for a light emitting layer for an organic EL element.

Examples of a known phosphorescence dopant are compound described in the following publications.

Nature 395, 151 (1998), Appl. Phys. Lett. 78, 1622 (2001), Adv. Mater. 19, 739 (2007), Chem. Mater. 17, 3532 (2005), Adv. Mater. 17, 1059 (2005), WO 2009/100991, WO 2008/101842, WO 2003/040257, US 2006/835469, US 2006/0202194, US 2007/0087321, US 2005/0244673, Inorg. Chem. 40, 1704 (2001), Chem. Mater. 16, 2480 (2004), Adv. Mater. 16, 2003 (2004), Angew. Chem. Int. Ed. 2006, 45, 7800, Appl. Phys. Lett. 86, 153505 (2005), Chem. Lett. 34, 592 (2005), Chem. Commun. 2906 (2005), Inorg. Chem. 42, 1248 (2003), WO 2009/050290, WO 2002/015645, WO 2009/000673, US 2002/0034656, U.S. Pat. No. 7,332,232, US 2009/0108737, US 2009/0039776, U.S. Pat. No. 6,921,915, U.S. Pat. No. 6,687,266, US 2007/0190359, US 2006/0008670, US 2009/0165846, US 2008/0015355, U.S. Pat. No. 7,250,226, U.S. Pat. No. 7,396,598, US 2006/0263635, US 2003/0138657, US 2003/0152802, U.S. Pat. No. 7,090,928, Angew. Chem. Int. Ed. 47, 1 (2008), Chem. Mater. 18, 5119 (2006), Inorg. Chem. 46, 4308 (2007), Organometallics 23, 3745 (2004), Appl. Phys. Lett. 74, 1361 (1999), WO 2002/002714, WO 2006/009024, WO 2006/056418, WO 2005/019373, WO 2005/123873, WO 2005/123873, WO 2007/004380, WO 2006/082742, US 2006/0251923, US 2005/0260441, U.S. Pat. No. 7,393,599, U.S. Pat. No. 7,534,505, U.S. Pat. No. 7,445,855, US 2007/0190359, US 2008/0297033, U.S. Pat. No. 7,338,722, US 2002/0134984, and U.S. Pat. No. 7,279,704, US 2006/098120, US 2006/103874, WO 2005/076380, WO 2010/032663, WO 2008/140115, WO 2007/052431, WO 2011/134013, WO 2011/157339, WO 2010/086089, WO 2009/113646, WO 2012/020327, WO 2011/051404, WO 2011/004639, WO 2011/073149, JP-A 2012-069737, JP Application No. 2011-181303, JP-A 2009-114086, JP-A 2003-81988, JP-A 2002-302671 and JP-A 2002-363552.

Among them, preferable phosphorescence emitting dopants are organic metal complexes containing Ir as a center metal. More preferable are complexes containing at least one coordination mode selected from a metal-carbon bond, a metal-nitrogen bond, a metal-oxygen bond and a metal-sulfur bond.

Specific examples of a known phosphorescence emitting dopant applicable to the present invention are cited in the following. The phosphorescence emitting dopants are not limited to them.

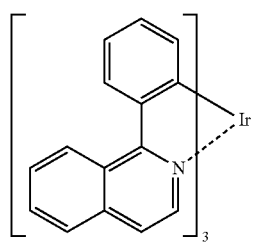

D-1

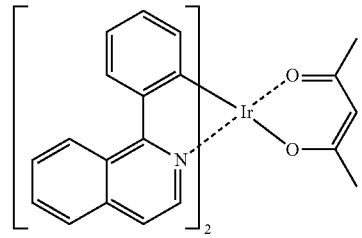

D-2

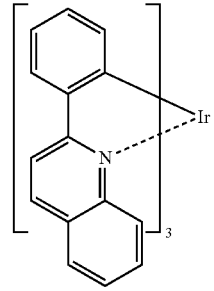

D-3

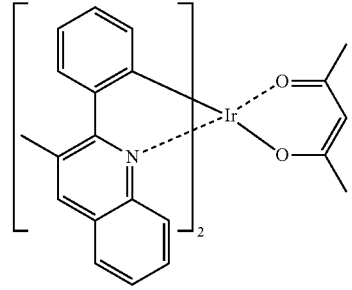

D-4

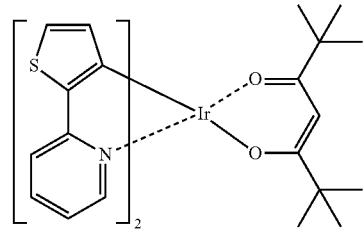

D-5

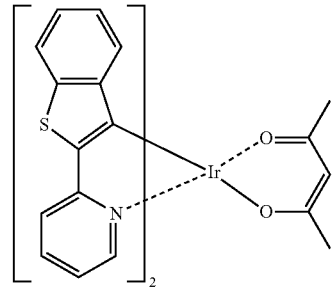

D-6

D-7
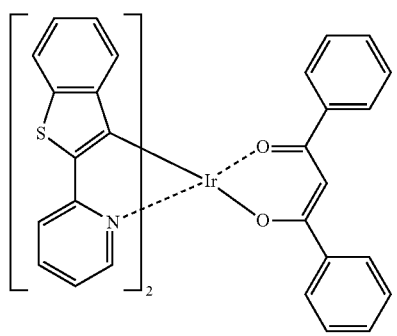
D-8
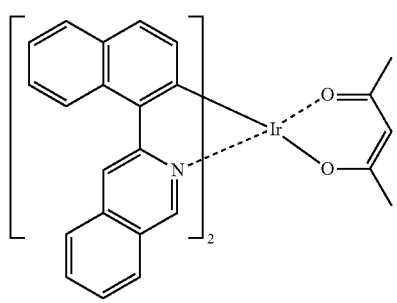
D-9
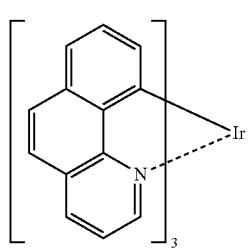
D-10
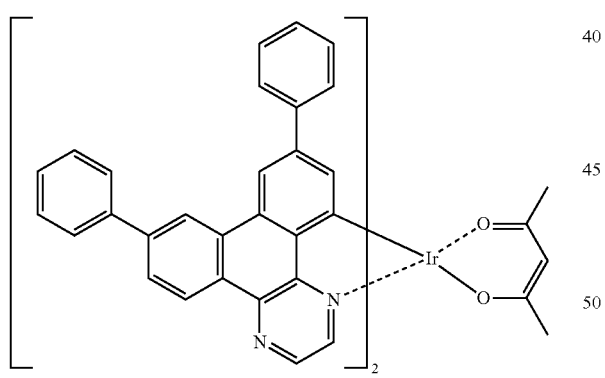
D-11
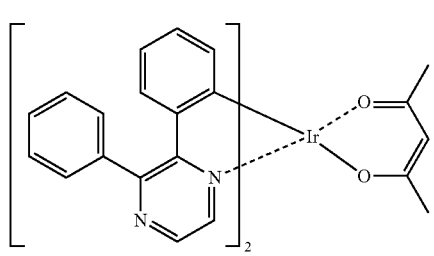
D-12
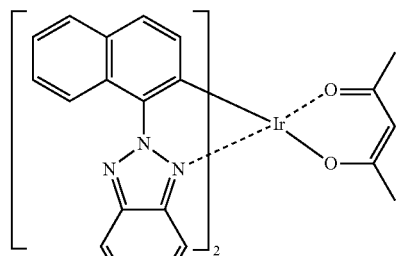
D-13
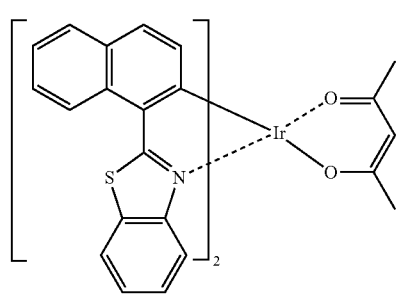
D-14
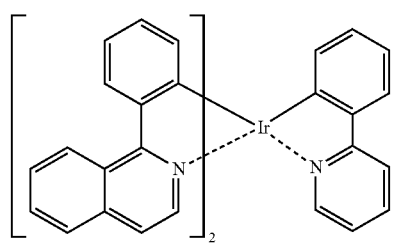
D-15
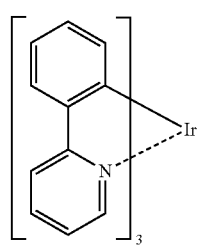
D-16
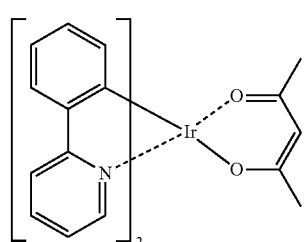
D-17
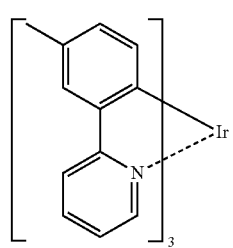

D-18
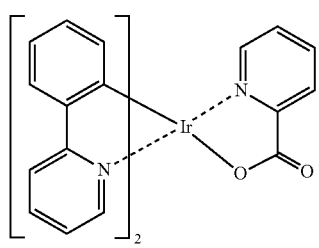
D-19
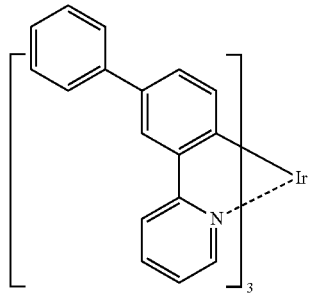
D-20
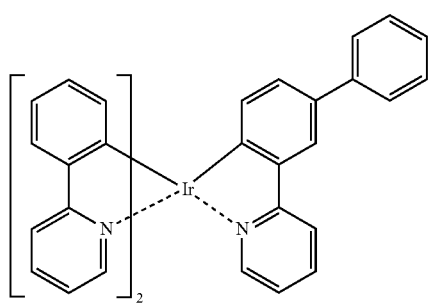
D-23
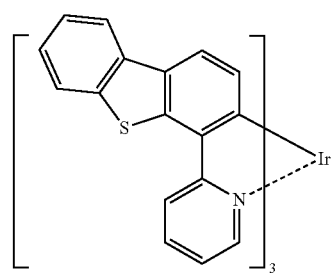
D-24
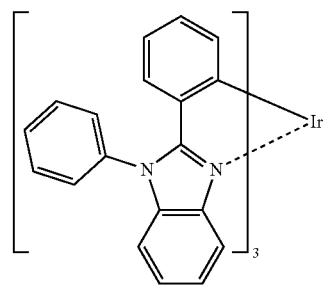
D-25
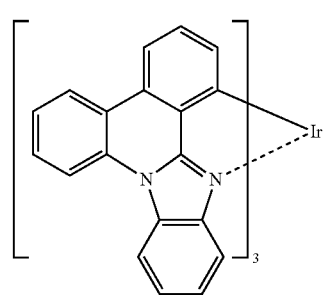
D-21
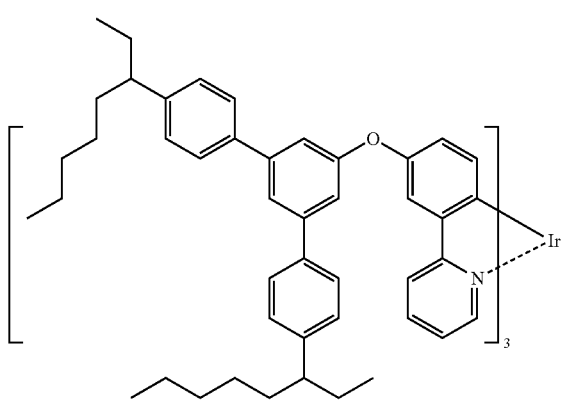
D-26
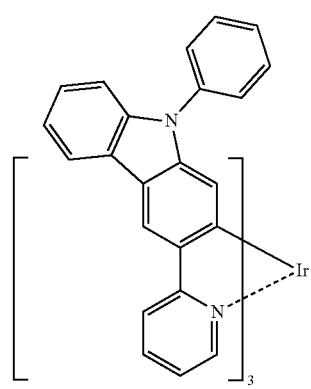
D-22
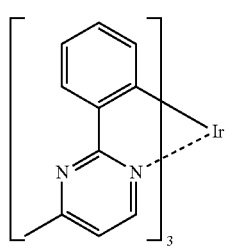
D-27
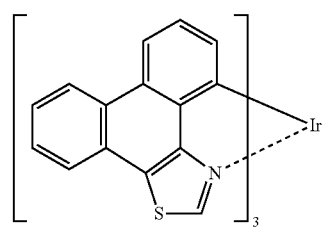

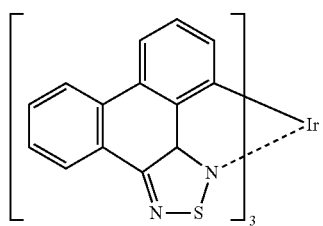
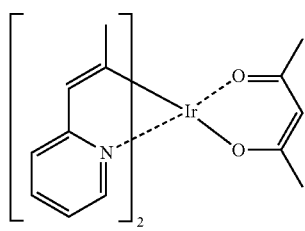
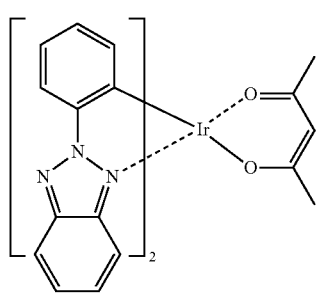
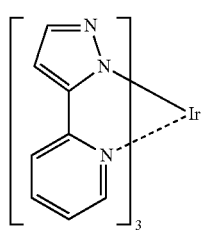
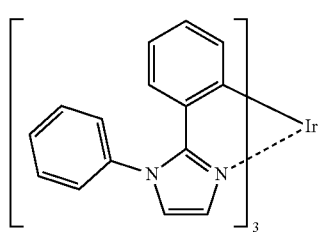
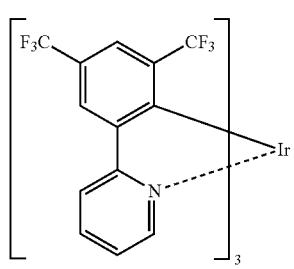
D-28
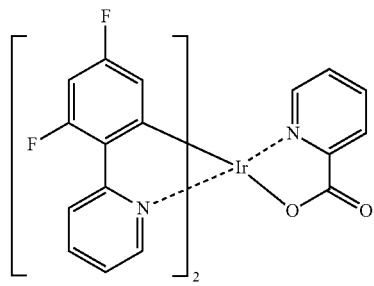
D-29
D-30
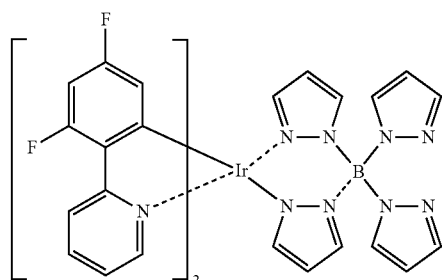
D-31
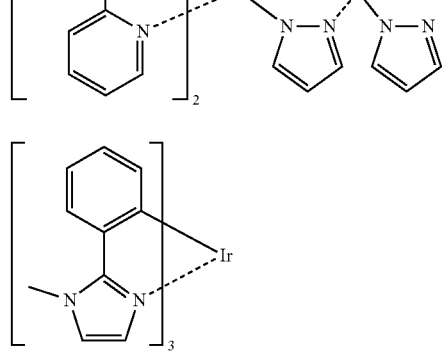
D-32
D-33
D-34
D-35
D-36
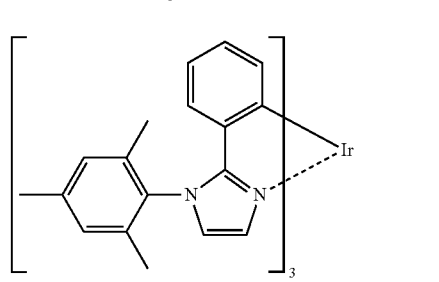
D-37
D-38
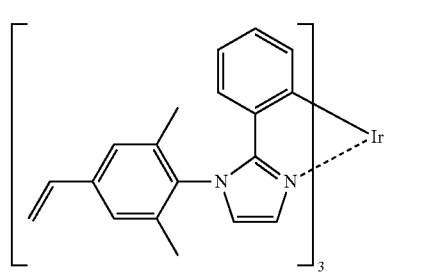
D-39

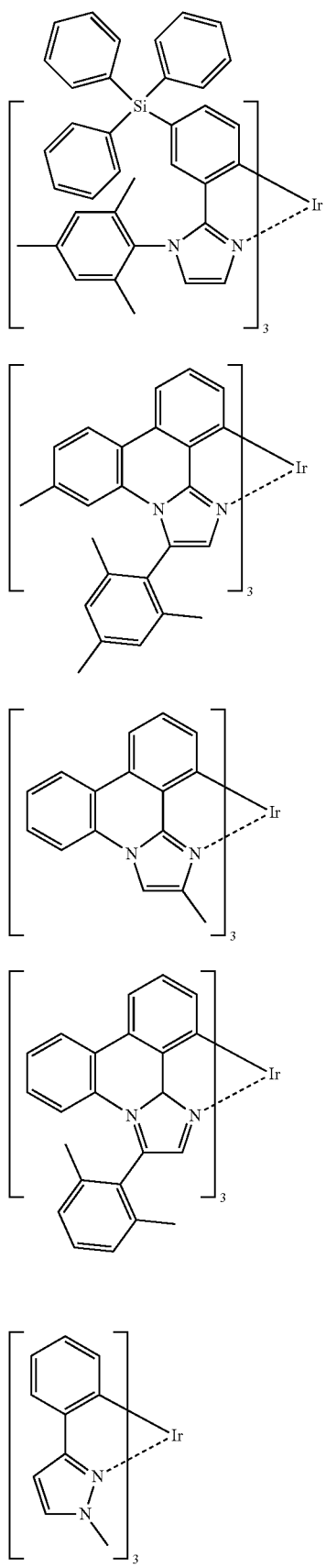
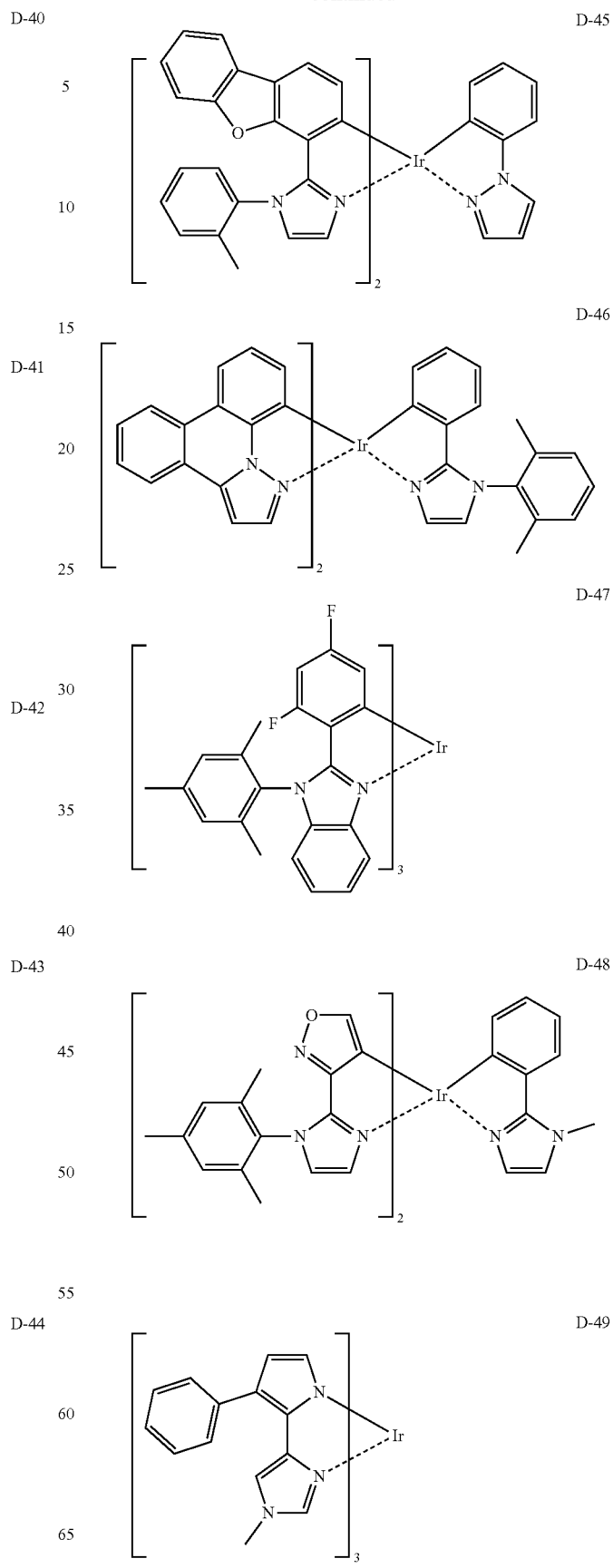

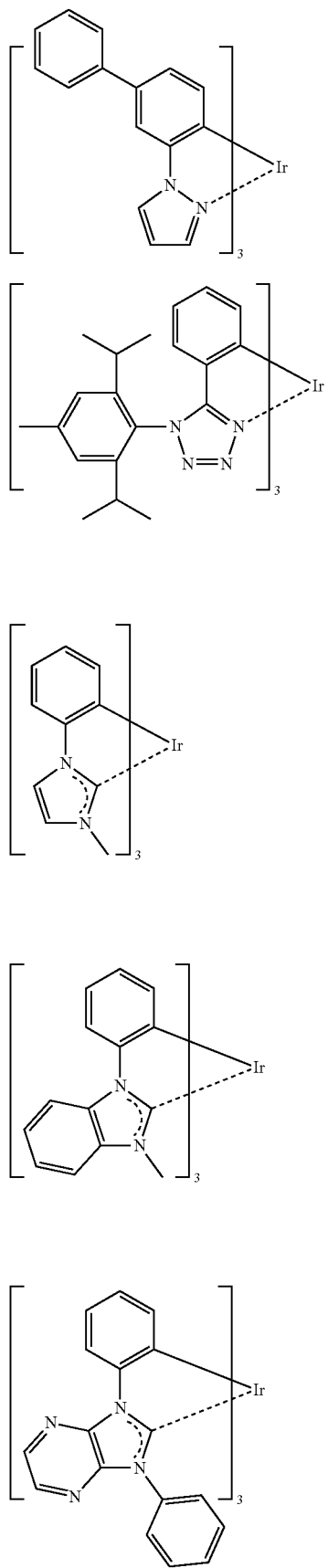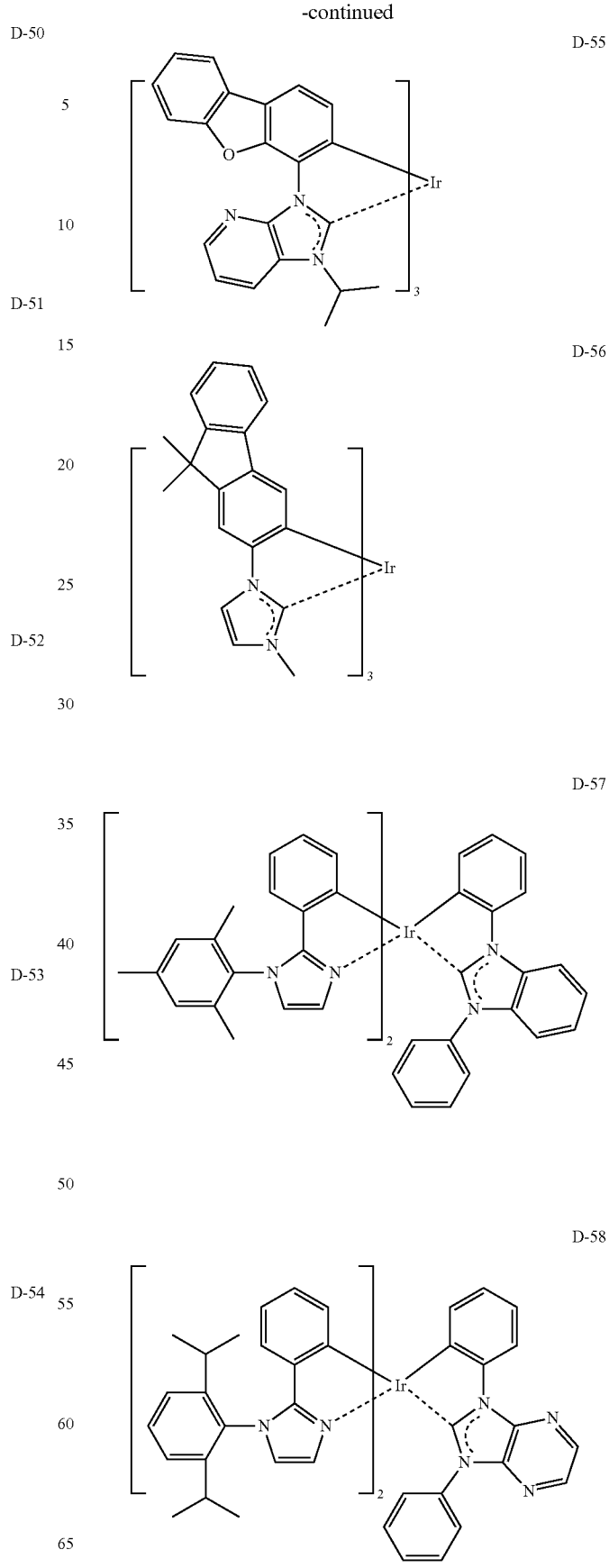

D-59
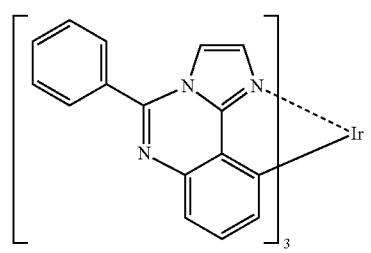
D-60
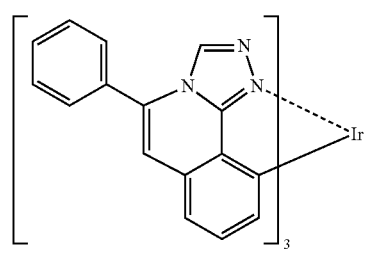
D-61
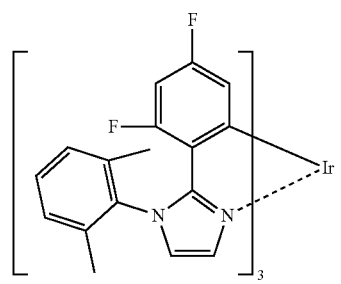
D-62
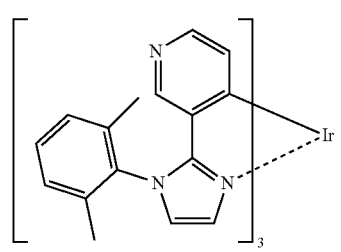
D-63
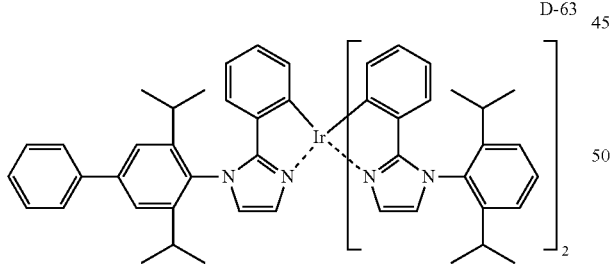
D-64
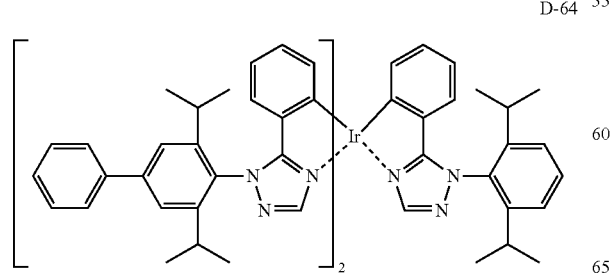
D-65
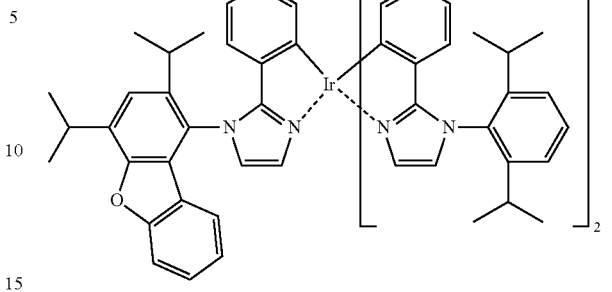
D-66
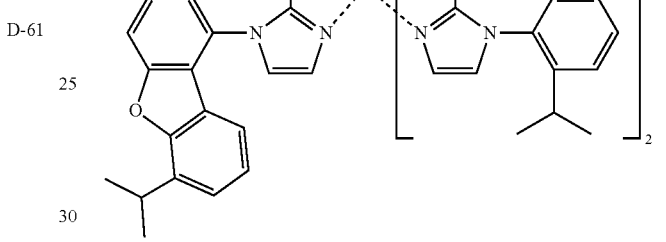
D-67
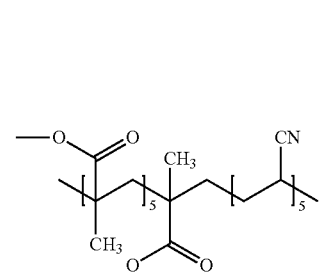
D-68
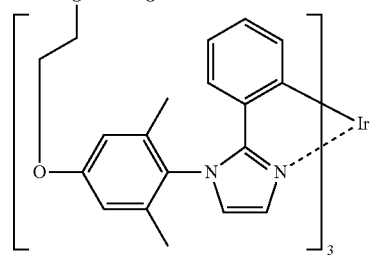

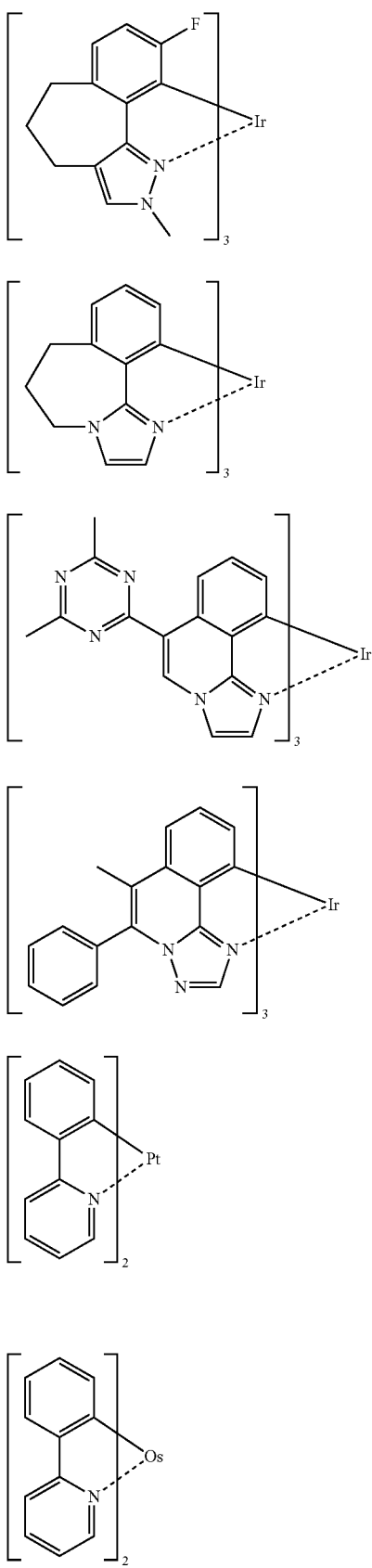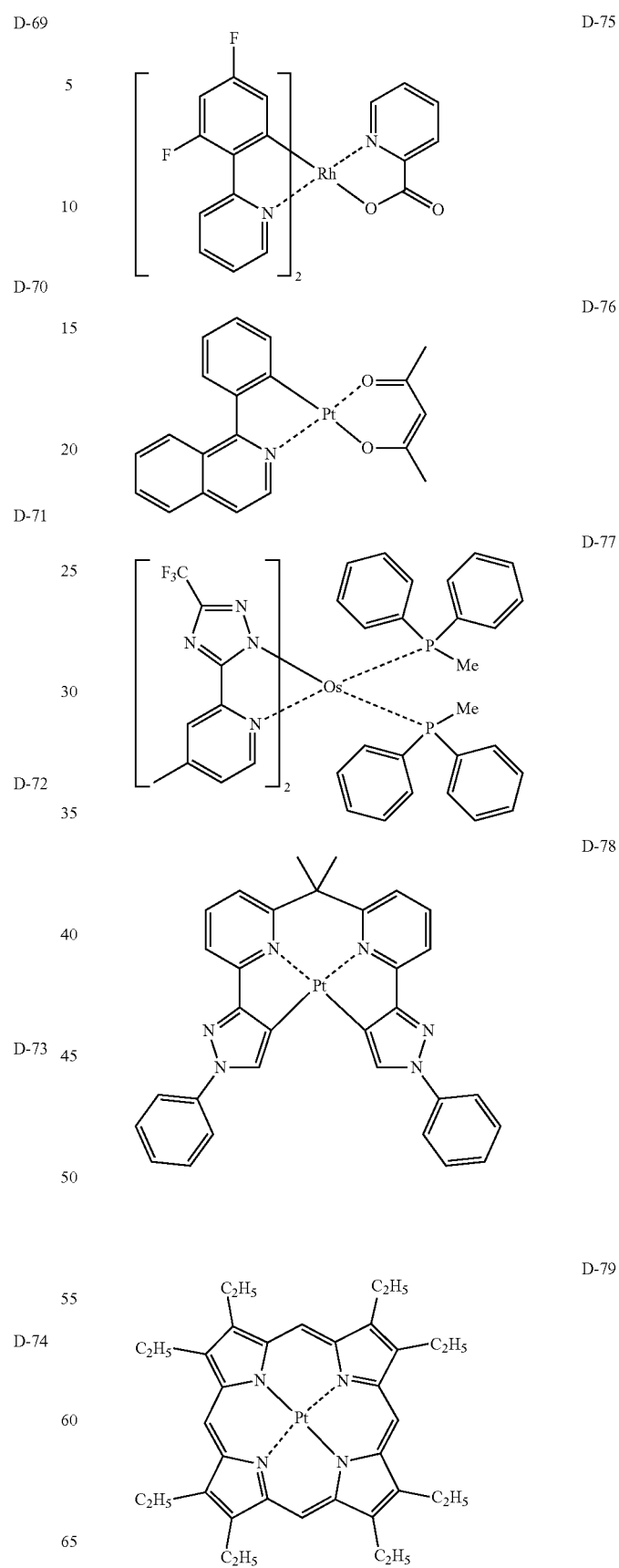

-continued

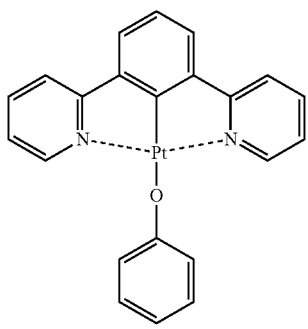

D-80

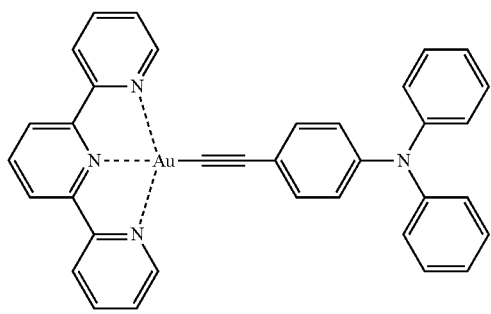

D-81

(2) Host Compound

A host compound according to the present invention is a compound which mainly plays a role of injecting or transporting a charge in a light emitting layer. In an organic EL element, an emission from the host compound itself is substantially not observed.

Preferably, a host compound is a compound exhibiting a phosphorescent quantum yield of the phosphorescence emission of less than 0.1 at room temperature (25° C.). More preferably, it is a compound exhibiting a phosphorescent quantum yield of less than 0.01. Further, among the compounds incorporated in the light emitting layer, a mass ratio of the host compound in the aforesaid layer is preferably at least 20%.

It is preferable that an exited energy level of a host compound is higher than an exited energy level of a light emitting dopant incorporated in the same layer.

Host compounds may be used singly or may be used in combination of two or more compounds. By using plural host compounds, it is possible to adjust transfer of charge, thereby it is possible to achieve high efficiency of an organic EL element.

A host compound used in the present invention is not specifically limited, and known compounds used in known organic EL elements may be used. For example, it may be either a low molecular weight compound or a polymer compound having a repeating unit. Further, it may be a compound provided with a reactive group such as a vinyl group and an epoxy group.

A known light emitting host which may be used in the present invention is preferably a compound having a hole transporting ability and an electron transporting ability, as well as preventing elongation of an emission wavelength and having a high Tg (a glass transition temperature). It is preferable that a host compound has a Tg of 90° C. or more, more preferably, has a Tg of 120° C. or more.

Here, a glass transition temperature (Tg) is a value obtained using DCS (Differential Scanning Colorimetry) based on the method in conformity to JIS-K-7121.

As specific examples of known host compounds used in an organic EL element of the present invention, the compounds described in the following Documents are cited. However, the present invention is not to them.

Japanese patent application publication (JP-A) Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837; US Patent Application Publication (US) Nos. 2003/0175553, 2006/0280965, 2005/0112407, 2009/0017330, 2009/0030202, 2005/0238919; WO 2001/039234, WO 2009/021126, WO 2008/056746, WO 2004/093 207, WO 2005/089025, WO 2007/063796, WO 2007/063754, WO 2004/107822, WO 2005/030900, WO 2006/114966, WO 2009/086028, WO 2009/003898, WO 2012/023947, JP-A 2008-074939, JP-A 2007-254297 and EP 2034538.

<<Electron Transport Layer>>

An electron transport layer of the present invention is composed of a material having a function of transferring an electron. It is only required to have a function of transporting an injected electron from a cathode to a light emitting layer.

A total layer thickness of the electron transport layer is not specifically limited, however, it is generally in the range of 2 nm to 5 μm, and preferably, it is in the range of 2 to 500 nm, and more preferably, it is in the range of 5 to 200 nm.

In an organic EL element of the present invention, it is known that there occurs interference between the light directly taken from the light emitting layer and the light reflected at the electrode located at the opposite side of the electrode from which the light is taken out at the moment of taking out the light which is produced in the light emitting layer. When the light is reflected at the cathode, it is possible to use effectively this interference effect by suitably adjusting the total thickness of the electron transport layer in the range of several nm to several μm.

On the other hand, the voltage will be increased when the layer thickness of the electron transport layer is made thick. Therefore, especially when the layer thickness is large, it is preferable that the electron mobility in the electron transport layer is $10^{-5}$ cm$^2$/Vs or more.

As a material used for an electron transport layer (hereafter, it is called as an electron transport material), it is only required to have either a property of ejection or transport of electrons, or a barrier to holes. Any of the conventionally known compounds may be selected and they may be employed.

Cited examples include: a nitrogen-containing aromatic heterocyclic derivative (a carbazole derivative, an azacarbazole derivative (a compound in which one or more carbon atoms constituting the carbazole ring are substitute with nitrogen atoms), a pyridine derivative, a pyrimidine derivative, a pyrazine derivative, a pyridazine derivative, a triazine derivative, a quinoline derivative, a quinoxaline derivative, a phenanthroline derivative, an azatriphenylene derivative, an oxazole derivative, a triazole derivative, an oxadiazole derivative, a thiadiazole derivative, a triazole derivative, a benzimidazole derivative, a benzoxazole derivative, and a benzothiazole derivative); a dibenzofuran derivative, a dibenzothiophene derivative, a silole derivative; and an aromatic hydrocarbon ring derivative (a naphthalene derivative, an anthracene derivative and a triphenylene derivative).

Further, metal complexes having a ligand of a 8-quinolinol structure or dibnenzoquinolinol structure such as tris(8-quinolinol)aluminum ($Alq_3$), tris(5,7-dichloro-8-quinolinol) aluminum, tris(5,7-dibromo-8-quinolinol)aluminum, tris(2-methyl-8-quinolinol)aluminum, tris(5-methyl-8-quinolinol) aluminum and bis(8-quinolinol)zinc (Znq); and metal complexes in which a central metal of the aforesaid metal complexes is substituted by In, Mg, Cu, Ca, Sn, Ga or Pb, may be also utilized as an electron transport material.

Further, a metal-free or metal phthalocyanine, or a compound whose terminal is substituted by an alkyl group or a sulfonic acid group, may be preferably utilized as an electron transport material. A distyryl pyrazine derivative, which is exemplified as a material for a light emitting layer, may be used as an electron transport material. Further, in the same manner as used for a hole injection layer and a hole transport layer, an inorganic semiconductor such as an n-type Si and an n-type SiC may be also utilized as an electron transport material.

It may be used a polymer compound having incorporating any one of these compound in a polymer side chain, or a compound having any one of these compound in a polymer main chain.

In an electron transport layer according to the present invention, it is possible to employ an electron transport layer of a higher n property (electron rich) which is doped with impurities as a guest material. As examples of a dope material, listed are those described in each of JP-A Nos. 4-297076, 10-270172, 2000-196140, 2001-102175, as well as in J. Appl. Phys., 95, 5773 (2004).

Although the present invention is not limited thereto, preferable examples of a known electron transport material used in an organic EL element of the present invention are compounds described in the following publications.

U.S. Pat. No. 6,528,187, U.S. Pat. No. 7,230,107, US 2005/0025993, US 2004/0036077, US 2009/0115316, US 2009/0101870, US 2009/0179554, WO 2003/060956, WO 2008/132085, Appl. Phys. Lett. 75, 4 (1999), Appl. Phys. Lett. 79, 449 (2001), Appl. Phys. Lett. 81, 162 (2002), Appl. Phys. Lett. 81, 162 (2002), Appl. Phys. Lett. 79, 156 (2001), U.S. Pat. No. 7,964,293, US 2009/030202, WO 2004/080975, WO 2004/063159, WO 2005/085387, WO 2006/067931, WO 2007/086552, WO 2008/114690, WO 2009/069442, WO 2009/066779, WO 2009/054253, WO 2011/086935, WO 2010/150593, WO 2010/047707, EP 2311826, JP-A 2010-251675, JP-A 2009-209133, JP-A 2009-124114, JP-A 2008-277810, JP-A 2006-156445, JP-A 2005-340122, JP-A 2003-45662, JP-A 2003-31367, JP-A 2003-282270, and WO 2012/115034.

Examples of a more preferable electron transport material of the present invention are: a pyridine derivative, a pyrimidine derivative, a pyrazine derivative, a triazine derivative, a dibenzofuran derivative, a dibenzothiophene derivative, a carbazole derivative, an azacarbazole derivative, and a benzimidazole derivative.

An electron transport material may be used singly, or may be used in combination of plural kinds of compounds.

<<Hole Blocking Layer>>

A hole blocking layer is a layer provided with a function of an electron transport layer in a broad meaning. Preferably, it contains a material having a function of transporting an electron, and having very small ability of transporting a hole. It can improve the recombination probability of an electron and a hole by blocking a hole while transporting an electron.

Further, a composition of an electron transport layer described above may be appropriately utilized as a hole blocking layer of the present invention when needed.

A hole blocking layer placed in an organic EL element of the present invention is preferably arranged at a location in the light emitting layer adjacent to the cathode side.

A thickness of a hole blocking layer according to the present invention is preferably in the range of 3 to 100 nm, and more preferably, in the range of 5 to 30 nm.

With respect to a material used for a hole blocking layer, the material used in the aforesaid electron transport layer is suitably used, and further, the material used as the aforesaid host compound is also suitably used for a hole blocking layer.

<<Electron Injection Layer>>

An electron injection layer (it is also called as "a cathode buffer layer") according to the present invention is a layer which is arranged between a cathode and a light emitting layer to decrease an operating voltage and to improve an emission luminance. An example of an electron injection layer is detailed in volume 2, chapter 2 "Electrode materials" (pp. 123-166) of "Organic EL Elements and Industrialization Front thereof (Nov. 30, 1998, published by N.T.S. Co. Ltd.)".

In the present invention, an electron injection layer is provided according to necessity, and as described above, it is placed between a cathode and a light emitting layer, or between a cathode and an electron transport layer.

An electron injection layer is preferably a very thin layer. The layer thickness thereof is preferably in the range of 0.1 nm to 5 nm depending on the materials used. In addition, the layer may be an unequal layer in which the composing material exists intermittently.

An election injection layer is detailed in JP-A Nos. 6-325871, 9-17574, and 10-74586. Examples of a material preferably used in an election injection layer include: a metal such as strontium and aluminum; an alkaline metal compound such as lithium fluoride, sodium fluoride, or potassium fluoride; an alkaline earth metal compound such as magnesium fluoride; a metal oxide such as aluminum oxide; and a metal complex such as lithium 8-hydroxyquinolate (Liq). It is possible to use the aforesaid electron transport materials.

The above-described materials may be used singly or plural kinds may be used in an election injection layer.

<<Hole Transport Layer>>

In the present invention, a hole transport layer contains a material having a function of transporting a hole. A hole transport layer is only required to have a function of transporting a hole injected from an anode to a light emitting layer.

The total layer thickness of a hole transport layer of the present invention is not specifically limited, however, it is generally in the range of 5 nm to 5 μm, preferably in the range of 2 to 500 nm, and more preferably in the range of 5 to 200 nm.

A material used in a hole transport layer (hereafter, it is called as a hole transport material) is only required to have any one of properties of injecting and transporting a hole, and a barrier property to an electron. A hole transport material may be suitably selected from the conventionally known compounds. A hole transport material may be used singly, or plural kinds may be used.

Examples of a hole transport material include: a porphyrin derivative, a phthalocyanine derivative, an oxazole derivative, an oxadiazole derivative, a triazole derivative, an imidazole derivative, a pyrazoline derivative, a pyrazolone derivative, a phenylenediamine derivative, a hydrazone derivative, a stilbene derivative, a polyarylalkane derivative, a triarylamine derivative, a carbazole derivative, an indolocarbazole derivative, an isoindole derivative, an acene derivative of anthracene or naphthalene, a fluorene derivative, a fluorenone derivative, polyvinyl carbazole, a polymer or an oligomer containing an aromatic amine in a side chain or a main chain, polysilane, and a conductive polymer or oligomer (e.g., PEDOT: PSS, aniline type copolymer, polyaniline and polythiophene).

Examples of a triarylamine derivative include: a benzidine type represented by α-NPD (4,4'-bis[N-(1-naphthyl)-N-phenylamino]biphenyl), a star burst type represented by MTDATA (4,4',4"-tris(N-(3-methylphenyl)-N-phenylamino)triphenylamine), a compound having fluorenone or anthracene in a triarylamine bonding core.

A hexaazatriphenylene derivative described in JP-A Nos. 2003-519432 and 2006-135145 may be also used as a hole transport material.

In addition, it is possible to employ an electron transport layer of a higher p property which is doped with impurities. As its example, listed are those described in each of JP-A Nos. 4-297076, 2000-196140, and 2001-102175, as well as in J. Appl. Phys., 95, 5773 (2004).

Further, it is possible to employ so-called p-type hole transport materials, and inorganic compounds such as p-type Si and p-type SiC, as described in JP-A No. 11-251067, and J. Huang et al. reference (Applied Physics Letters 80 (2002), p. 139). Moreover, an orthometal compounds having Ir or Pt as a center metal represented by Ir(ppy)$_3$ are also preferably used.

Although the above-described compounds may be used as a hole transport material, preferably used are: a triarylamine derivative, a carbazole derivative, an indolocarbazole derivative, an azatriphenylene derivative, an organic metal complex, a polymer or an oligomer incorporated an aromatic amine in a main chain or in a side chain.

Specific examples of a known hole transport material used in an organic EL element of the present invention are compounds in the aforesaid publications and in the following publications. However, the present invention is not limited to them.

Appl. Phys. Lett. 69, 2160(1996), J. Lumin. 72-74, 985 (1997), Appl. Phys. Lett. 78, 673(2001), Appl. Phys. Lett. 90, 183503(2007), Appl. Phys. Lett. 51, 913(1987), Synth. Met. 87, 171(1997), Synth. Met. 91, 209(1997), Synth. Met. 111, 421(2000), SID Symposium Digest, 37, 923(2006), J. Mater. Chem. 3, 319(1993), Adv. Mater. 6, 677(1994), Chem. Mater. 15, 3148(2003), US 2003/0162053, US 2002/0158242, US 2006/0240279, US 2008/0220265, U.S. Pat. No. 5,061,569, WO 2007/002683, WO 2009/018009, EP 650955, US 2008/0124572, US 2007/0278938, US 2008/0106190, US 2008/0018221, WO 2012/115034, JP-A 2003-519432, JP-A 2006-135145, and U.S. patent application Ser. No. 13/585,981.

A hole transport material may be used singly or may be used in combination of plural kinds of compounds.

<<Electron Blocking Layer>>

An electron blocking layer is a layer provided with a function of a hole transport layer in a broad meaning. Preferably, it contains a material having a function of transporting a hole, and having very small ability of transporting an electron. It can improve the recombination probability of an electron and a hole by blocking an electron while transporting a hole. Further, a composition of a hole transport layer described above may be appropriately utilized as an electron blocking layer of an organic EL element of the present invention when needed.

An electron blocking layer placed in an organic EL element of the present invention is preferably arranged at a location in the light emitting layer adjacent to the anode side.

A thickness of an electron blocking layer is preferably in the range of 3 to 100 nm, and more preferably, in the range of 5 to 30 nm.

With respect to a material used for an electron blocking layer, the material used in the aforesaid hole transport layer is suitably used, and further, the material used as the aforesaid host compound is also suitably used for an electron blocking layer.

<<Hole Injection Layer>>

A hole injection layer (it is also called as "an anode buffer layer") is a layer which is arranged between an electrode and a light emitting layer to decrease an operating voltage and to improve an emission luminance. An example of a hole injection layer is detailed in volume 2, chapter 2 "Electrode materials" (pp. 123-166) of "Organic EL Elements and Industrialization Front thereof (Nov. 30, 1998, published by N.T.S. Co. Ltd.)".

A hole injection layer is provided according to necessity, and as described above, it is placed between an anode and a light emitting layer, or between an anode and a hole transport layer.

A hole injection layer is also detailed in JP-A Nos. 9-45479, 9-260062 and 8-288069. Materials used in the hole injection layer are the same materials used in the aforesaid hole transport layer.

Among them, preferable materials are: a phthalocyanine derivative represented by copper phthalocyanine; a hexaazatriphenylene derivative described in JP-A Nos. 2003-519432 and 2006-135145; a metal oxide represented by vanadium oxide; a conductive polymer such as amorphous carbon, polyaniline (or called as emeraldine) and polythiophene; an orthometalated complex represented by tris(2-phenylpyridine) iridium complex; and a triarylamine derivative.

The above-described materials used in a hole injection layer may be used singly or plural kinds may be used.

<<Additive>>

The above-described organic layer of the present invention may further contain other additive.

Examples of an additive are: halogen elements such as bromine, iodine and chlorine, and a halide compound; and a compound, a complex and a salt of an alkali metal, an alkaline earth metal and a transition metal such as Pd, Ca and Na.

Although a content of an additive may be arbitrarily decided, preferably, it is 1,000 ppm or less based on the total mass of the layer containing the additive, more preferably, it is 500 ppm or less, and still more preferably, it is 50 ppm or less.

In order to improve a transporting ability of an electron or a hole, or to facilitate energy transport of an exciton, the content of the additive is not necessarily within these range, and other range of content may be used.

<<Forming Method of Organic Layers>>

It will be described forming methods of organic layers according to the present invention (hole injection layer, hole transport layer, light emitting layer, hole blocking layer, electron transport layer, and electron injection layer).

Forming methods of organic layers according to the present invention are not specifically limited. They may be formed by using a known method such as a vacuum vapor deposition method and a wet method (wet process).

Examples of a wet process include: a spin coating method, a cast method, an inkjet method, a printing method, a die coating method, a blade coating method, a roll coating method, a spray coating method, a curtain coating method, and a LB method (Langmuir Blodgett method). From the viewpoint of getting a uniform thin layer with high productivity, preferable are method highly appropriate to a roll-to-roll method such as a die coating method, a roll coating method, an inkjet method, and a spray coating method.

Examples of a liquid medium to dissolve or to disperse a material for organic layers according to the present invention include: ketones such as methyl ethyl ketone and cyclohexanone; aliphatic esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; organic solvents such as DMF and DMSO.

These will be dispersed with a dispersion method such as an ultrasonic dispersion method, a high shearing dispersion method and a media dispersion method.

A different film forming method may be applied to every organic layer. When a vapor deposition method is adopted for forming each layer, the vapor deposition conditions will change depending on the compounds used. Generally, the following ranges are suitably selected for the conditions, heating temperature of boat: 50 to 450° C., level of vacuum: $10^{-6}$ to $10^{-2}$ Pa, vapor deposition rate: 0.01 to 50 nm/sec, temperature of substrate: −50 to 300° C., and layer thickness: 0.1 nm to 5 µm, preferably 5 to 200 nm.

Formation of organic layers of the present invention is preferably continuously carried out from a hole injection layer to a cathode with one time vacuuming. It may be taken out on the way, and a different layer forming method may be employed. In that case, the operation is preferably done under a dry inert gas atmosphere.

<<Anode>>

As an anode of an organic EL element, a metal having a large work function (4 eV or more, preferably, 4.5 eV or more), an alloy, and a conductive compound and a mixture thereof are utilized as an electrode substance.

Specific examples of an electrode substance are: metals such as Au, and an alloy thereof; transparent conductive materials such as CuI, indium tin oxide (ITO), $SnO_2$, and ZnO. Further, a material such as IDIXO ($In_2O_3$—ZnO), which can form an amorphous and transparent electrode, may also be used.

As for an anode, these electrode substances may be made into a thin layer by a method such as a vapor deposition method or a sputtering method; followed by making a pattern of a desired form by a photolithography method. Otherwise, in the case of requirement of pattern precision is not so severe (about 100 µm or more), a pattern may be formed through a mask of a desired form at the time of layer formation with a vapor deposition method or a sputtering method using the above-described material.

Alternatively, when a coatable substance such as an organic conductive compound is employed, it is possible to employ a wet film forming method such as a printing method or a coating method. When emitted light is taken out from the anode, the transmittance is preferably set to be 10% or more. A sheet resistance of a first electrode is preferably a few hundred Ω/sq or less.

Further, although a layer thickness of the anode depends on a material, it is generally selected in the range of 10 nm to 1 µm, and preferably in the range of 10 to 200 nm.

<<Cathode>>

As a cathode, a metal having a small work function (4 eV or less) (it is called as an electron injective metal), an alloy, a conductive compound and a mixture thereof are utilized as an electrode substance. Specific examples of the aforesaid electrode substance includes: sodium, sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, aluminum, and a rare earth metal. Among them, with respect to an electron injection property and durability against oxidation, preferable are: a mixture of election injecting metal with a second metal which is stable metal having a work function larger than the electron injecting metal. Examples thereof are: a magnesium/silver mixture, a magnesium/aluminum mixture, a magnesium/indium mixture, an aluminum/aluminum oxide ($Al_2O_3$) mixture, a lithium/aluminum mixture and aluminum.

A cathode may be made by using these electrode substances with a method such as a vapor deposition method or a sputtering method to form a thin film. A sheet resistance of the a cathode is preferably a few hundred Ω/sq or less. A layer thickness of the cathode is generally selected in the range of 10 nm to 5 µm, and preferably in the range of 50 to 200 nm.

In order to transmit emitted light, it is preferable that one of an anode and a cathode of an organic EL element is transparent or translucent for achieving an improved luminescence.

Further, after forming a layer of the aforesaid metal having a thickness of 1 to 20 nm on the cathode, it is possible to prepare a transparent or translucent cathode by providing with a conductive transparent material described in the description for the anode thereon. By applying this process, it is possible to produce an element in which both an anode and a cathode are transparent.

<<Support Substrate>>

A support substrate which may be used for an organic EL element of the present invention is not specifically limited with respect to types of such as glass and plastics. Hereafter, the support substrate may be also called as substrate body, substrate, substrate substance, or support. They me be transparent or opaque. However, a transparent support substrate is preferable when the emitting light is taken from the side of the support substrate. Support substrates preferably utilized includes such as glass, quartz and transparent resin film. A specifically preferable support substrate is a resin film capable of providing an organic EL element with a flexible property.

Examples of a resin film include: polyesters such as polyethylene terephthalate (PET) and polyethylene naphthalate (PEN), polyethylene, polypropylene, cellophane, cellulose esters and their derivatives such as cellulose diacetate, cellulose triacetate (TAC), cellulose acetate butyrate, cellulose acetate propionate (CAP), cellulose acetate phthalate, and cellulose nitrate, polyvinylidene chloride, polyvinyl alcohol, polyethylene vinyl alcohol, syndiotactic polystyrene, polycarbonate, norbornene resin, polymethyl pentene, polyether ketone, polyimide, polyether sulfone (PES), polyphenylene sulfide, polysulfones, polyether imide, polyether ketone imide, polyamide, fluororesin, Nylon, polymethyl methacrylate, acrylic resin, polyarylates and cycloolefin resins such as ARTON (trade name, made by JSR Co. Ltd.) and APEL (trade name, made by Mitsui Chemicals, Inc.).

On the surface of a resin film, it may be formed a film incorporating an inorganic or an organic compound or a hybrid film incorporating both compounds. Barrier films are preferred at a water vapor permeability of 0.01 g/(m²·24 h) or less (at 25±0.5° C., and 90±2% RH) determined based on JIS K 7129-1992. Further, high barrier films are preferred to have an oxygen permeability of $1\times10^{-3}$ cm³/(m²·24 h·atm) or less determined based on JIS K 7126-1987, and a water vapor permeability) of $1\times10^{-5}$ g/(m²·24 h) or less.

As materials forming a barrier film, employed may be those which retard penetration of moisture and oxygen, which deteriorate the element. For example, it is possible to employ silicon oxide, silicon dioxide, and silicon nitride. Further, in order to improve the brittleness of the aforesaid film, it is more preferable to achieve a laminated layer structure of inorganic layers and organic layers. The laminating order of the inorganic layer and the organic layer is not particularly limited, but it is preferable that both are alternatively laminated a plurality of times.

Barrier film forming methods are not particularly limited, and examples of employable methods include a vacuum deposition method, a sputtering method, a reactive sputtering method, a molecular beam epitaxy method, a cluster ion beam method, an ion plating method, a plasma polymerization method, a plasma CVD method, a laser CVD method, a thermal CVD method, and a coating method. Of these, specifically preferred is a method employing an atmospheric pressure plasma polymerization method, described in JP-A No. 2004-68143.

Examples of opaque support substrates include metal plates such aluminum or stainless steel films, opaque resin substrates, and ceramic substrates.

The external taking out quantum efficiency of light emitted by the organic EL element of the present invention is preferably at least 1% at room temperature, but is more preferably at least 5%.

External taking out quantum efficiency (%)=(Number of photons emitted by the organic EL element to the exterior/Number of electrons fed to organic EL element)×100.

Further, it may be used simultaneously a color hue improving filter such as a color filter, or it may be used simultaneously a color conversion filter which convert emitted light color from the organic EL element to multicolor by employing fluorescent materials.

<<Sealing>>

As sealing means employed in the present invention, listed may be, for example, a method in which sealing members, electrodes, and a supporting substrate are subjected to adhesion via adhesives. The sealing members may be arranged to cover the display region of an organic EL element, and may be a concave plate or a flat plate. Neither transparency nor electrical insulation is limited.

Specifically listed are glass plates, polymer plate-films, metal plate-films. Specifically, it is possible to list, as glass plates, soda-lime glass, barium-strontium containing glass, lead glass, aluminosilicate glass, borosilicate glass, barium borosilicate glass, and quartz. Further, listed as polymer plates may be polycarbonate, acryl, polyethylene terephthalate, polyether sulfide, and polysulfone. As a metal plate, listed are those composed of at least one metal selected from the group consisting of stainless steel, iron, copper, aluminum magnesium, nickel, zinc, chromium, titanium, molybdenum, silicon, germanium, and tantalum, or alloys thereof.

In the present invention, since it is possible to achieve a thin organic EL element, it is preferable to employ a polymer film or a metal film. Further, it is preferable that the polymer film has an oxygen permeability of $1\times10^{-3}$ cm³/m²/24 h or less determined by the method based on JIS K 7126-1987, and a water vapor permeability of $1\times10^{-3}$ g/(m²24 h) or less (at 25±0.5° C., and 90±2% RH) or less determined by the method based on JIS K 7129-1992.

Conversion of the sealing member into concave is carried out employing a sand blast process or a chemical etching process.

In practice, as adhesives, listed may be photo-curing and heat-curing types having a reactive vinyl group of acrylic acid based oligomers and methacrylic acid, as well as moisture curing types such as 2-cyanoacrylates. Further listed may be thermal and chemical curing types (mixtures of two liquids) such as epoxy based ones. Still further listed may be hot-melt type polyamides, polyesters, and polyolefins. Yet further listed may be cationically curable type UV curable epoxy resin adhesives.

In addition, since an organic EL element is occasionally deteriorated via a thermal process, those are preferred which enable adhesion and curing between room temperature and 80° C. Further, desiccating agents may be dispersed into the aforesaid adhesives. Adhesives may be applied onto sealing portions via a commercial dispenser or printed on the same in the same manner as screen printing.

Further, it is appropriate that on the outside of the aforesaid electrode which interposes the organic layer and faces the support substrate, the aforesaid electrode and organic layer are covered, and in the form of contact with the support substrate, inorganic and organic material layers are formed as a sealing film. In this case, as materials forming the aforesaid film may be those which exhibit functions to retard penetration of moisture or oxygen which results in deterioration. For example, it is possible to employ silicon oxide, silicon dioxide, and silicon nitride.

Still further, in order to improve brittleness of the aforesaid film, it is preferable that a laminated layer structure is formed, which is composed of these inorganic layers and layers composed of organic materials. Methods to form these films are not particularly limited. It is possible to employ, for example, a vacuum deposition method, a sputtering method, a reactive sputtering method, a molecular beam epitaxy method, a cluster ion beam method, an ion plating method, a plasma polymerization method, an atmospheric pressure plasma polymerization method, a plasma CVD method, a thermal CVD method, and a coating method.

It is preferable to inject a gas phase and a liquid phase material of inert gases such as nitrogen or argon, and inactive liquids such as fluorinated hydrocarbon or silicone oil into the space between the space formed with the sealing member and the display region of the organic EL element. Further, it is possible to form vacuum in the space. Still further, it is possible to enclose hygroscopic compounds in the interior of the space.

Examples of hygroscopic compounds include: metal oxides (for example, sodium oxide, potassium oxide, calcium oxide, barium oxide, magnesium oxide, and aluminum oxide); sulfates (for example, sodium sulfate, calcium sulfate, magnesium sulfate, and cobalt sulfate); metal halides (for example, calcium chloride, magnesium chloride, cesium fluoride, tantalum fluoride, cerium bromide, magnesium bromide, barium iodide, and magnesium iodide); perchlorates (for example, barium perchlorate and magnesium perchlorate). In sulfates, metal halides, and perchlorates, suitably employed are anhydrides. For sulfate salts, metal halides and perchlorates, suitably used are anhydrous salts.

<<Protective Film and Protective Plate>>

On the aforesaid sealing film which interposes the organic layer and faces the support substrate or on the outside of the aforesaid sealing film, a protective or a protective plate may be arranged to enhance the mechanical strength of the element. Specifically, when sealing is achieved via the aforesaid sealing film, the resulting mechanical strength is not always high enough, whereby it is preferable to arrange the protective film or the protective plate described above. Usable materials for these include glass plates, polymer plate-films, and metal plate-films which are similar to those employed for the aforesaid sealing. However, in terms of light weight and decrease in thickness, it is preferable to employ a polymer film.

<<Light Extraction>>

It is generally known that an organic EL element emits light in the interior of the layer exhibiting the refractive index (being about 1.6 to 2.1) which is greater than that of air, whereby only about 15% to 20% of light generated in the light emitting layer is extracted. This is due to the fact that light incident to an interface (being an interlace of a transparent substrate to air) at an angle of θ which is at least critical angle is not extracted to the exterior of the element due to the resulting total reflection, or light is totally reflected between the transparent electrode or the light emitting layer and the transparent substrate, and light is guided via the transparent electrode or the light emitting layer, whereby light escapes in the direction, of the element side surface.

Means to enhance the efficiency of the aforesaid light extraction include, for example: a method in which roughness is formed on the surface of a transparent substrate, whereby total reflection is minimized at the interface of the transparent substrate to air (U.S. Pat. No. 4,774,435), a method in which efficiency is enhanced in such a manner that a substrate results in light collection (JP-A No. 63-314795), a method in which a reflection surface is formed on the side of the element (JP-A No. 1-220394), a method in which a flat layer of a middle refractive index is introduced between the substrate and the light emitting body and an antireflection film is formed (JP-A No. 62-172691), a method in which a flat layer of a refractive index which is equal to or less than the substrate is introduced between the substrate and the light emitting body (JP-A No. 2001-202827), and a method in which a diffraction grating is formed between the substrate and any of the layers such as the transparent electrode layer or the light emitting layer (including between the substrate and the outside) (JP-A No. 11-283751).

In the present invention, it is possible to employ these methods while combined with the organic EL element of the present invention. Of these, it is possible to appropriately employ the method in which a flat layer of a refractive index which is equal to or less than the substrate is introduced between the substrate and the light emitting body and the method in which a diffraction grating is formed between any layers of a substrate, and a transparent electrode layer and a light emitting layer (including between the substrate and the outside space).

By combining these means, the present invention enables the production of elements which exhibit higher luminance or excel in durability.

When a low refractive index medium of a thickness, which is greater than the wavelength of light, is formed between the transparent electrode and the transparent substrate, the extraction efficiency of light emitted from the transparent electrode to the exterior increases as the refractive index of the medium decreases.

As materials of the low refractive index layer, listed are, for example, aerogel, porous silica, magnesium fluoride, and fluorine based polymers. Since the refractive index of the transparent substrate is commonly about 1.5 to 1.7, the refractive index of the low refractive index layer is preferably approximately 1.5 or less. More preferably, it is 1.35 or less.

Further, thickness of the low refractive index medium is preferably at least two times of the wavelength in the medium. The reason is that, when the thickness of the low refractive index medium reaches nearly the wavelength of light so that electromagnetic waves escaped via evanescent enter into the substrate, effects of the low refractive index layer are lowered.

The method in which the interface which results in total reflection or a diffraction grating is introduced in any of the media is characterized, in that light extraction efficiency is significantly enhanced. The above method works as follows. By utilizing properties of the diffraction grating capable of changing the light direction to the specific direction different from diffraction via so-called Bragg diffraction such as primary diffraction or secondary diffraction of the diffraction grating, of light emitted from the light entitling layer, light, which is not emitted to the exterior due to total reflection between layers, is diffracted via introduction of a diffraction grating between any layers or in a medium (in the transparent substrate and the transparent electrode) so that light is extracted to the exterior.

It is preferable that the introduced diffraction grating exhibits a two-dimensional periodic refractive, index. The reason is as follows. Since light emitted in the light emitting layer is randomly generated to all directions, in a common one-dimensional diffraction grating exhibiting a periodic refractive index distribution only in a certain direction, light which travels to the specific direction is only diffracted, whereby light extraction efficiency is not sufficiently enhanced.

However, by changing the refractive index distribution to a two-dimensional one, light, which travels to all directions, is diffracted, whereby the light extraction efficiency is enhanced.

A position to introduce a diffraction grating may be between any layers or in a medium (in a transparent substrate or a transparent electrode). However, a position near the organic light emitting layer, where light is generated, is preferable. In this case, the cycle of the diffraction grating is preferably from about ½ to 3 times of the wavelength of light in the medium. The preferable arrangement of the diffraction grating is such that the arrangement is two-dimensionally repeated in the form of a square lattice, a triangular lattice, or a honeycomb lattice.

<<Light Collection Sheet>>

Via a process to arrange a structure such as a micro-lens array shape on the light extraction side of the organic EL element of the present invention or via combination with a so-called light collection sheet, light is collected in the specific direction such as the front direction with respect to the light emitting element surface, whereby it is possible to enhance luminance in the specific direction.

In an example of the micro-lens array, square pyramids to realize a side length of 30 μm and an apex angle of 90 degrees are two-dimensionally arranged on the light extraction side of the substrate. The side length is preferably 10 to 100 μm. When it is less than the lower limit, coloration occurs due to generation of diffraction effects, while when it exceeds the upper limit, the thickness increases undesirably.

It is possible to employ, as a light collection sheet, for example, one which is put into practical use in the LED backlight of liquid crystal display devices. It is possible to employ, as such a sheet, for example, the luminance enhancing film (BEF), produced by Sumitomo 3M Limited. As shapes of a prism sheet employed may be, for example, Δ shaped stripes of an apex angle of 90 degrees and a pitch of 50 μm formed on a base material, a shape in which the apex angle is rounded, a shape in which the pitch is randomly changed, and other shapes.

Further, in order to control the light radiation angle from the light emitting element, simultaneously employed may be a light diffusion plate-film. For example, it is possible to employ the diffusion film (LIGHT-UP), produced by Kimoto Co., Ltd.

<<Applications>>

It is possible to employ the organic EL element of the present invention as display devices, displays, and various types of light emitting sources.

Examples of light emitting sources include: lighting apparatuses (home lighting and car lighting), clocks, backlights for liquid crystals, sign advertisements, signals, light sources of light memory media, light sources of electrophotographic copiers, light sources of light communication processors, and light sources of light sensors. The present invention is not limited to them. It is especially effectively employed as a backlight of a liquid crystal display device and a lighting source.

If needed, the organic EL element of the present, invention may undergo patterning via a metal mask or an ink-jet printing method during film formation. When the patterning is carried out, only an electrode may undergo patterning, an electrode and a light emitting layer may undergo patterning, or all element layers may undergo patterning. During preparation of the element, it is possible to employ conventional methods.

In the following, one example of a display device provided with an organic EL element of the present invention will be explained with reference to figures.

FIG. 1 is a schematic drawing to show an example of a display device constituted of an organic EL element. It is a schematic drawing of a display, which displays image information by emission of an organic EL element, such as a mobile phone.

Display 1 is constituted of display section A having plural number of pixels and control section B which performs image scanning of display section A based on image information.

Control section B, which is electrically connected to display section A, sends a scanning signal and an image data signal to plural number of pixels based on image information from the outside and pixels of each scanning line successively emit depending on the image data signal by a scanning signal to perform image scanning, whereby image information is displayed on display section A.

Figure 2:
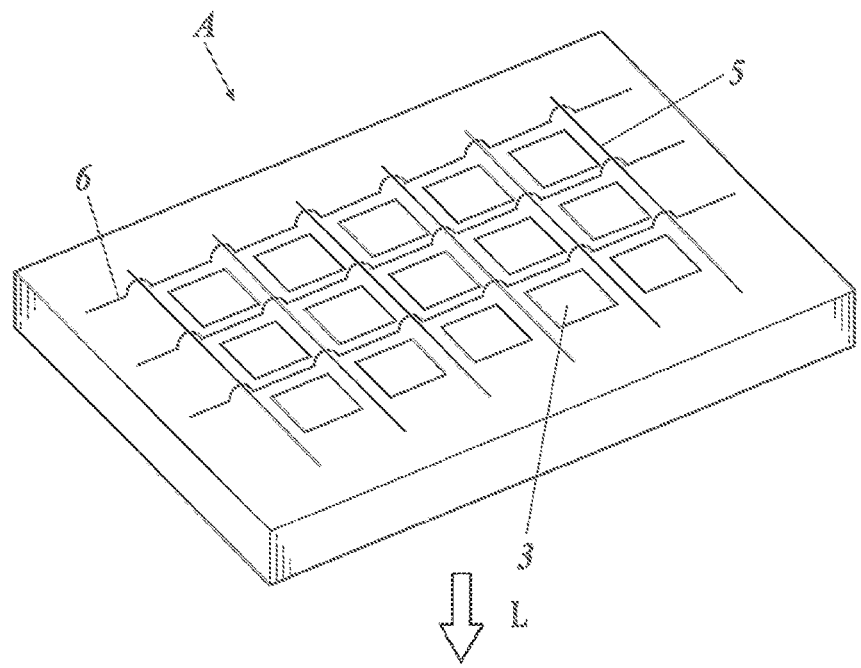
FIG. 2 is a schematic drawing of display section.

FIG. 2 is a schematic drawing of display section A.

Display section A is provided with such as a wiring section, which contains plural scanning lines 5 and data lines 6, and plural pixels 3 on a substrate. Primary part materials of display section A will be explained in the following.

In the drawing, shown is the case that light emitted by pixel 3 is taken out along the white allow (downward).

Scanning lines 5 and plural data lines 6 in a wiring section each are comprised of a conductive material, and scanning lines 5 and data lines 6 are perpendicular in a grid form and are connected to pixels 3 at the right-angled crossing points (details are not shown in the drawing).

Pixel 3 receives an image data from data line 6 when a scanning signal is applied from scanning line 5 and emits according to the received image data.

Full-color display is possible by appropriately arranging pixels having an emission color in a red region, pixels in a green region and pixels in a blue region, side by side on the same substrate.

Next, an emission process of a pixel will be explained.

Figure 3:
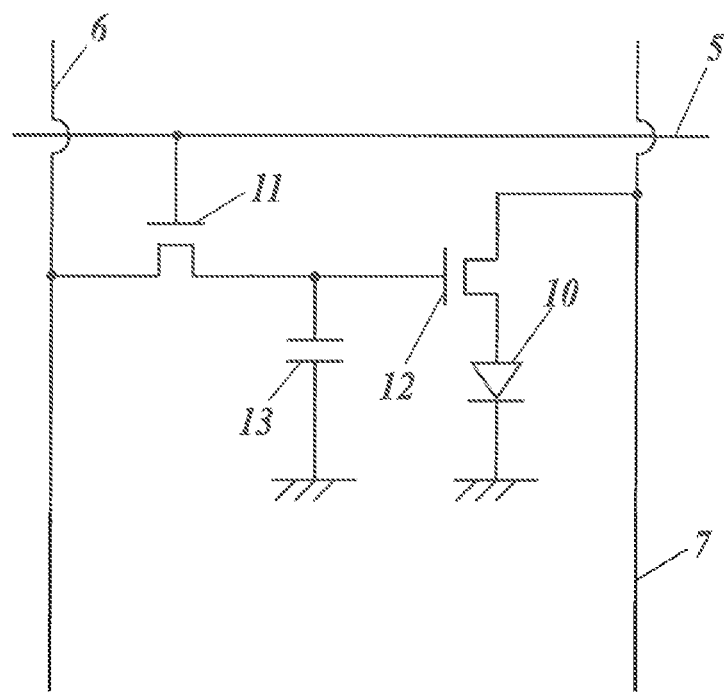
FIG. 3 is a circuit diagram of an image pixel.

FIG. 3 is a schematic drawing of a pixel.

A pixel is equipped with such as organic EL element 10, switching transistor 11, operating transistor 12 and capacitor 13. Red, green and blue emitting organic EL elements are utilized as organic EL element 10 for plural pixels, and full-color display device is possible by arranging these side by side on the same substrate.

In FIG. 3, an image data signal is applied on the drain of switching transistor 11 via data line 6 from control section B. Then when a scanning signal is applied on the gate of switching transistor 11 via scanning line 5 from control section B, operation of switching transistor is on to transmit the image data signal applied on the drain to the gates of capacitor 13 and operating transistor 12.

Operating transistor 12 is on, simultaneously with capacitor 13 being charged depending on the potential of an image data signal, by transmission of an image data signal. In operating transistor 12, the drain is connected to electric source line 7 and the source is connected to the electrode of organic EL element 10, and an electric current is supplied from electric source line 7 to organic EL element 10 depending on the potential of an image data applied on the gate.

When a scanning signal is transferred to next scanning line 5 by successive scanning of control section B, operation of switching transistor 11 is off.

However, since condenser 13 keeps the charged potential of an image data signal even when operation of switching transistor 11 is of operation of operating transistor 12 is kept on to continue emission of organic EL element 10 until the next scanning signal is applied.

When the next scanning signal is applied by successive scanning, operating transistor 12 operates depending on the potential of an image data signal synchronized to the scanning signal and organic EL element 10 emits.

That is, emission of each organic EL element 10 of plural pixels 3 is performed by providing switching transistor 11 and operating transistor 12 against each organic EL element 10 of plural pixels 3. Such an emission method is called as an active matrix mode.

Herein, emission of organic EL element 10 may be either emission of plural gradations based on a multiple-valued image data signal having plural number of gradation potentials or on and off of a predetermined emission quantity based on a binary image data signal. Further, potential hold of capacitor 13 may be either continuously maintained until the next scanning signal application or discharged immediately before the next scanning signal application.

In the present invention, emission operation is not necessarily limited to the above-described active matrix mode but may be a passive matrix mode in which organic EL element is emitted based on a data signal only when a scanning signal is scanned.

FIG. 4 is a schematic drawing of a display device based on a passive matrix mode. In FIG. 4, plural number of scanning lines 5 and plural number of image data lines 6 are arranged grid-wise, opposing to each other and sandwiching pixels 3.

When a scanning signal of scanning line 5 is applied by successive scanning, pixel 3 connected to scanning line 5 applied with said signal emits depending on an image data signal.

Since pixel 3 is provided with no active element in a passive matrix mode, decrease of manufacturing cost is possible.

<<One Embodiment of Lighting Device of the Present Invention>>

One embodiment of lighting devices provided with an organic EL element of the present invention will be described.

The non-light emitting surface of the organic EL element of the present invention was covered with a glass case, and a 300 μm thick glass substrate was employed as a sealing substrate. An epoxy based light curable type adhesive (LUXTRACK LC0629B produced by Toagosei Co., Ltd.) was employed in the periphery as a sealing material. The resulting one was superimposed on the aforesaid cathode to be brought into close contact with the aforesaid transparent support substrate, and curing and sealing were carried out via exposure of UV radiation onto the glass substrate side, whereby the lighting device shown in FIG. 5, R1 to R8, was formed.

Figure 5:
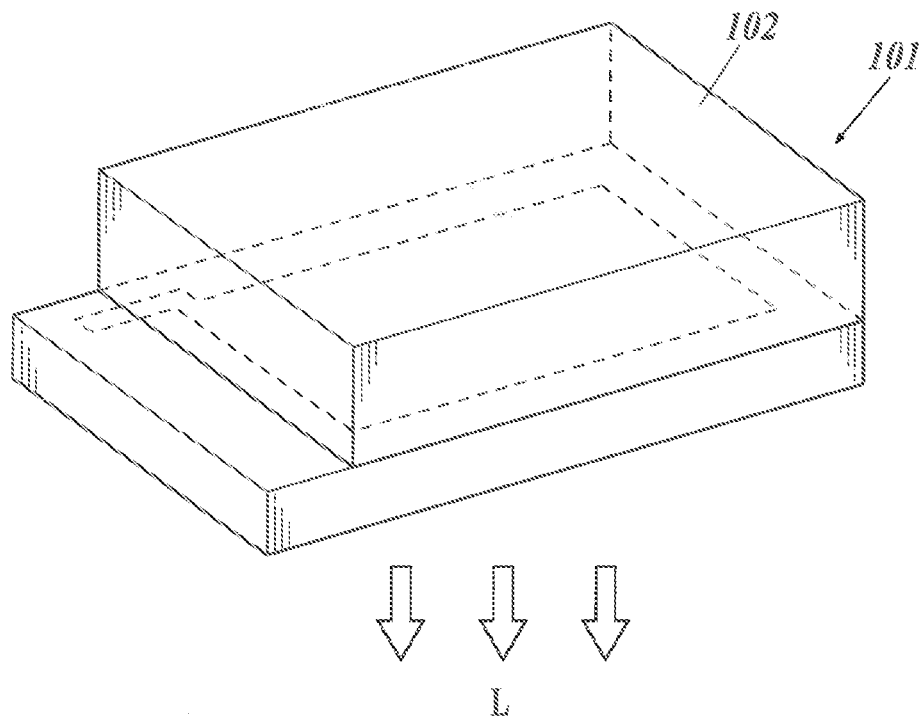
FIG. 5 is a schematic drawing of a lighting device.

FIG. 5 is a schematic view of a lighting device and Organic EL element 101 is covered with glass cover 102 (incidentally, sealing by the glass cover was carried out in a globe box under nitrogen ambience (under an ambience of high purity nitrogen gas at a purity of at least 99.999%) so that Organic EL Element 101 was not brought into contact with atmosphere).

Figure 6:
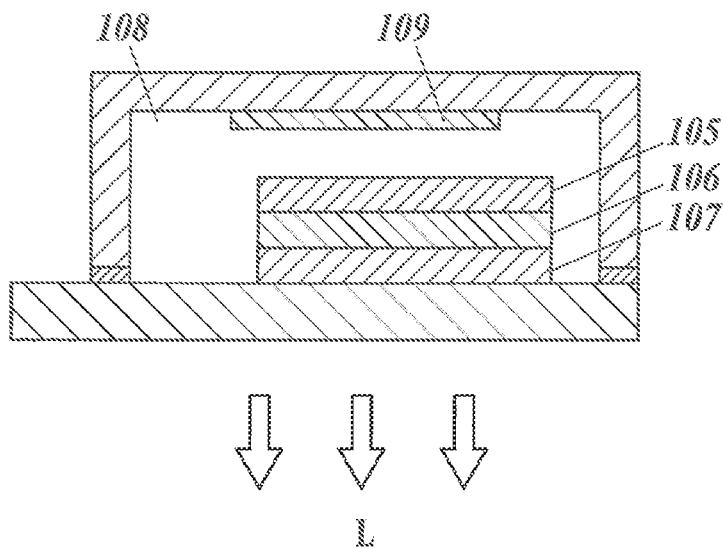
FIG. 6 is a cross-sectional drawing of a lighting device.

FIG. 6 is a cross-sectional view of a lighting device, and in FIG. 6, 105 represents a cathode, 106 represents an organic EL layer, and 107 represents a glass substrate fitted with a transparent electrode. Further, the interior of glass cover 102 is filled with nitrogen gas 108 and water catching agent 109 is provided.

<Example of Measurement of Thin Film Resistance with Impedance Spectroscopy Method>

An impedance spectroscopy method is a method of analysis by performing either converting or amplifying a subtle physical property change of an organic EL element. It is characterized in achieving measurement of resistance (R) and capacitance (C) with high sensitivity without destructing an organic EL element. It is commonly practiced to measure electric properties by using Z plot, M plot and ∈ plot for impedance spectroscopy analysis. The analysis method thereof is described in detail in pp. 423 to 425 of "Handbook of Thin film evaluation" published by Techno System, Co. Ltd, for example.

It will be described a method of obtaining resistance of a specified layer of an organic EL element by applying the impedance spectroscopy. Here, the organic EL element has a constitution of: [ITO/HIL (hole injection layer)/HTL (hole transport layer)/EML (light emitting layer)/ETL (electron transport layer)/EIL (electron injection layer)/Al]. When a resistance value of an electron transport layer (ETL) is measured, for example, there are prepared EL samples each having only a different thickness of ETL. By comparing M plot of each EL samples (refer to FIG. 7), it can determine the portion which correspond to ETL in the curve of M plot.

Figure 7:
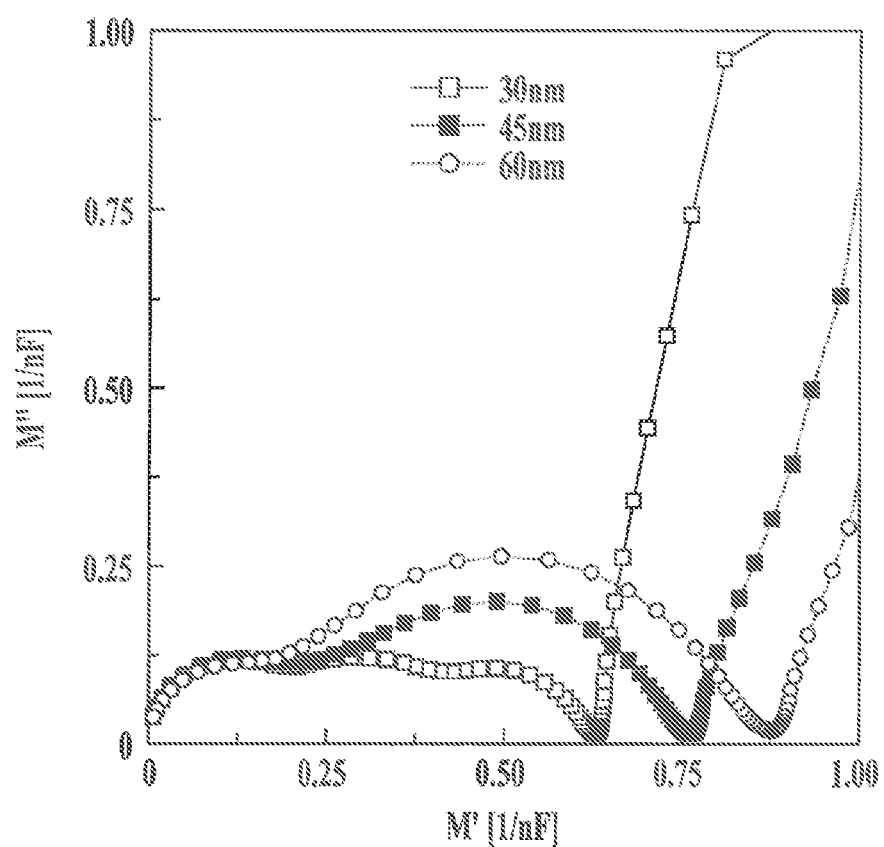
FIG. 7 is an example showing M plots of electron transport layers each having a different thickness.

FIG. 7 is an example showing M plots of electron transport layers each having a different thickness. It shows an example of the cases having a thickness of 30, 45 and 60 nm.

Figure 8:
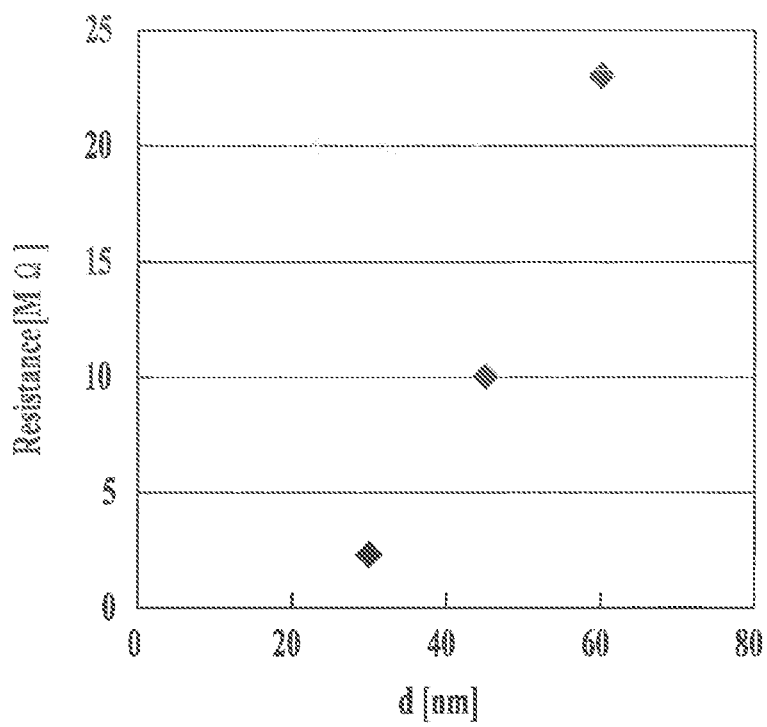
FIG. 8 is an example showing a relationship between a layer thickness and a resistance.

The resistance values (R) obtained from these plots are plotted with respect to the thickness of ETL in FIG. 8. The resistance value of each thickness can be determined since the plots having a ETL thickness and a resistance value are approximately on a straight line as shown in FIG. 8.

Figure 9:
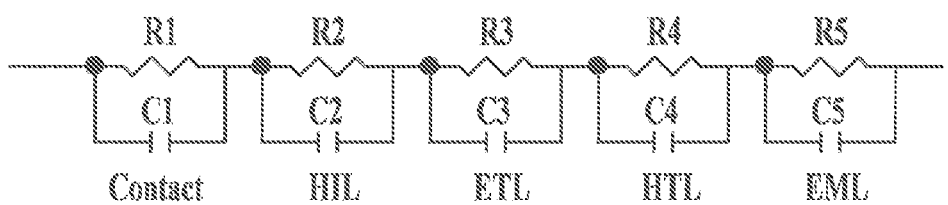
FIG. 9 is an example showing an equivalent circuit model of an organic electroluminescent element.
Figure 10:
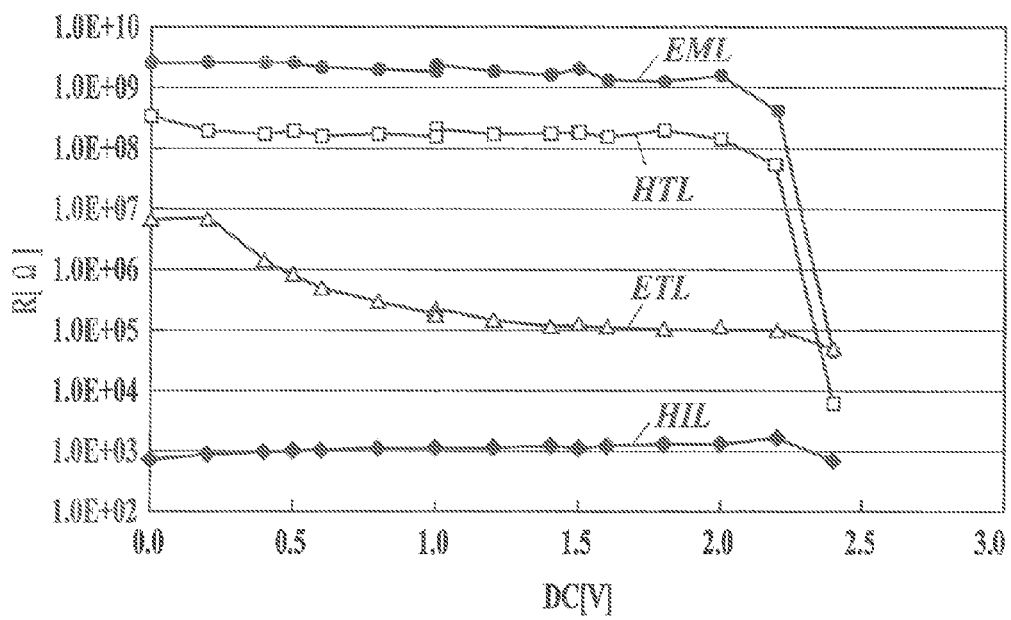
FIG. 10 is an example showing a relationship between a resistance and a voltage.

An organic EL element having an element constitution of: [ITO/HIL/HTL/EML/ETL/EIL/Al] was analyzed for each layer as an example of an equivalent circuit model (FIG. 9). The results of analysis are shown in FIG. 10. FIG. 10 is an example showing a relationship between a resistance and a voltage for each layer.

FIG. 9 shows an equivalent circuit model of an organic electroluminescent element having an element constitution of: [ITO/HIL/HTL/EML/ETL/EIL/Al].

FIG. 10 is an example of analysis results of an organic electroluminescent element having an element constitution of: [ITO/HIL/HTL/EML/ETL/EIL/Al].

Figure 11:
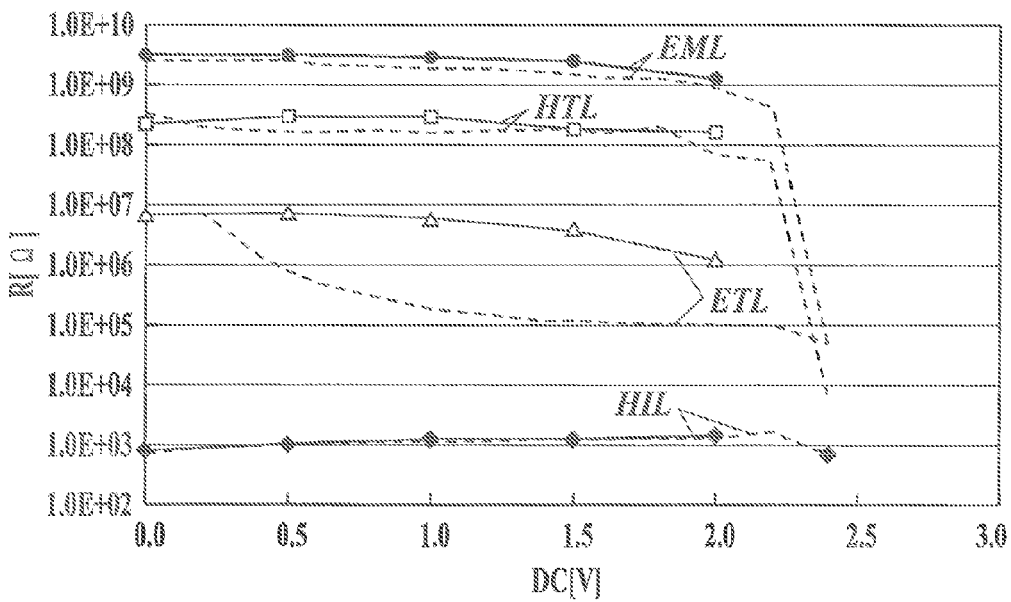
FIG. 11 is an example showing an analytical result of an organic electroluminescent element after deterioration.

On the other hand, FIG. 11 shows the measurement results obtained in the same conditions by using the same organic EL element with emitting light for a prolonged time and being deteriorated. The measurement results are superposed. The results at 1 V for each layer are shown in Table 1.

FIG. 11 is an example showing an analytical result of an organic electroluminescent element after deterioration.

TABLE 1

|  | HIL (Ω) | ETL (Ω) | HTL (Ω) | HML (Ω) |
|---|---|---|---|---|
| Before driving | 1.1k | 0.2M | 0.2 G | 1.9 G |
| After deterioration | 1.2k | 5.7M | 0.3 G | 2.9 G |

From the analysis results on the relation between the resistance value of each layer of an organic EL element and DC voltage, it was found the following. Among HIL (hole injection layer), ETL (electron transport layer), HTL (hole transport layer), and EML (light emitting layer) in the deteriorated organic EL element, only the resistance value of ETL (electron transport layer) was largely increased, and it became about 30 times larger at 1 V of DC voltage.

By using the method described above, the change of resistance before and after applying current can be measured as described in Examples of the present specification.

EXAMPLES

Hereafter, the present invention will be described specifically by referring to Examples, however, the present invention is not limited to them. In Examples, the term "parts" or "%" is used. Unless particularly mentioned, it represents "mass parts" or "mass %".

[Example 1](Vapor Deposition System)

The structures of the compounds used in the examples described below are shown in the following. In addition, Comparative compound A and Comparative compound B are compounds respectively described in WO 2007/142083 and WO 2012/087007.

Comparative compound A
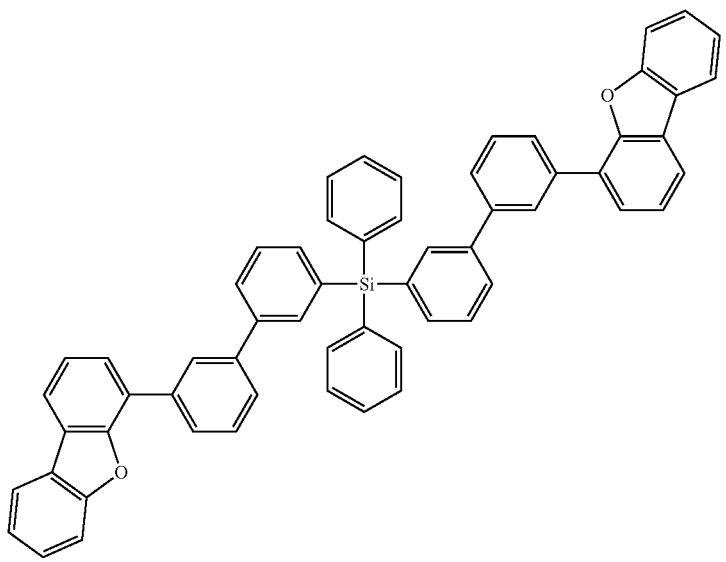
Comparative compound B
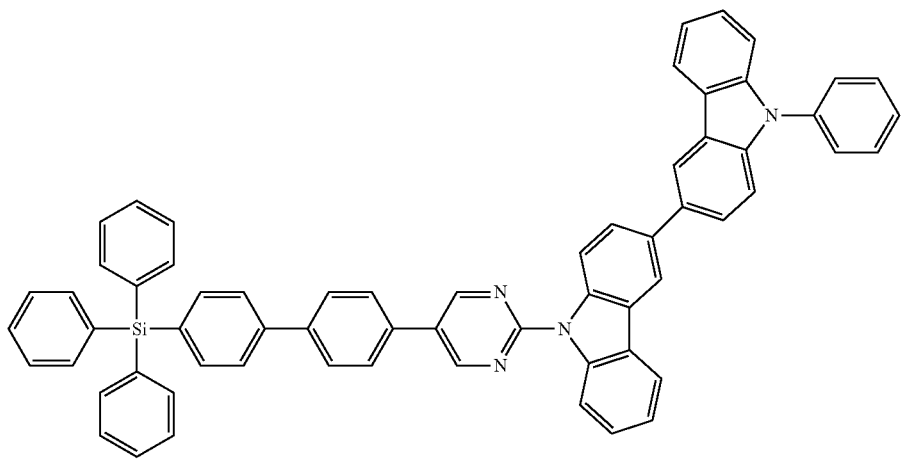
Comparative compound C
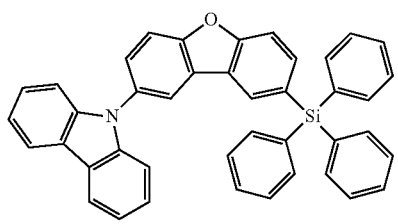
Comparative compound D
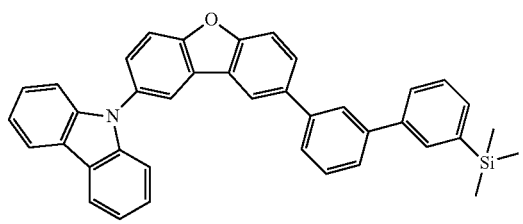
Implement DP
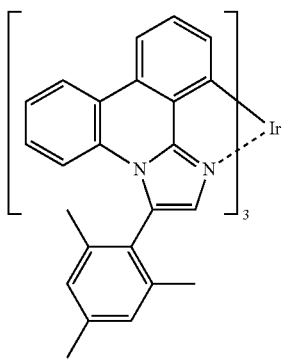
Implement-6
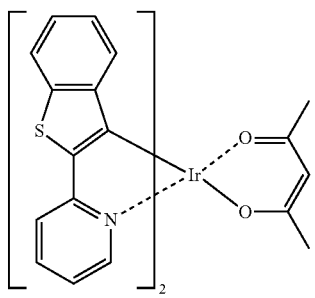

Implement-15

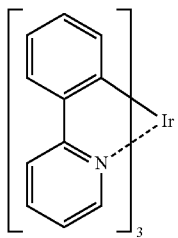

Implement-53

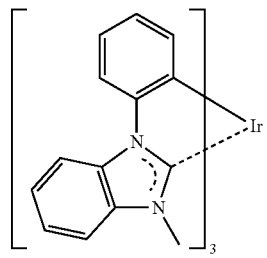

<<Preparation of Organic EL Element 1-1>>

An anode was prepared by making patterning to a glass substrate of 100 mm×100 mm×1.1 mm (NA45, produced by NH Techno Glass Corp.) on which ITO (indium tin oxide) was formed with a thickness of 100 nm. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

On the transparent support substrate thus prepared was applied a 70% solution of poly(3,4-ethylenedioxythiphene)-polystyrene sulfonate (PEDOT/PSS, Baytron P AI4083, made by Bayer AG.) diluted with water by using a spin coating method at 3,000 rpm for 30 seconds to form a film and then it was dried at 200° C. for one hour. A first hole injection layer having a thickness of 20 nm was prepared.

The resulting transparent support substrate was fixed to a substrate holder of a commercial vacuum deposition apparatus. Separately, 200 mg of α-NPD was placed in a molybdenum resistance heating boat, 200 mg of CBP (4,4'-N,N'-dicarbazolebiphenyl) was placed in another molybdenum resistance heating boat, 200 mg of light emitting dopant D-9 was placed in another molybdenum resistance heating boat, and 200 mg of BCP (2,9-dimethyl-4,7-diphenyl-1,10-phenanthroline) was placed in another molybdenum resistance heating boat. The resulting boats were fitted in the vacuum deposition apparatus.

Subsequently, after reducing the pressure of a vacuum tank to 4×10$^{-4}$ Pa, the aforesaid heating boat containing α-NPD was heated via application of electric current and deposition was made onto the aforesaid hole injection layer at a deposition rate of 0.1 nm/second, whereby it was produced a hole transport layer having a thickness of 30 nm.

Further, the aforesaid heating boats each respectively containing Comparative compound A and D-9 were heated via application of electric current and co-deposition was carried out onto the aforesaid hole transport layer at a respective deposition rate of 0.1 nm/second and 0.010 nm/second, whereby it was produced a light emitting layer having a thickness of 40 nm.

Further, the aforesaid heating boat containing BCP was heated via application of electric current and deposition was carried out onto the aforesaid hole blocking layer at a deposition rate of 0.1 nm/second, whereby it was produced an electron transport layer having a thickness of 30 nm.

Subsequently, 0.5 nm thick lithium fluoride was vapor deposited as a cathode buffer layer, and then, 110 nm thick aluminum was vapor deposited to form a cathode, whereby Organic EL element 1-1 was prepared.

<<Preparation of Organic EL Elements 1-2 to 1-30>>

Organic EL elements 1-2 to 1-30 were prepared in the same manner as preparation of Organic EL element 1-1 except that the light emitting dopant and the host compound were changed with the compounds described in Table 2.

<<Evaluation of Organic EL Elements 1-1 to 1-30>>

When the prepared organic EL elements were evaluated, the lighting device was formed as described below and evaluated. The non-light emitting surface of the prepared organic EL element was covered with a glass cover. An epoxy based light curable adhesive (LUXTRACK LC0629B, produced by Toagosei Co., Ltd.) was employed as a sealing material in the periphery of the glass cover contacting with the glass substrate on which the organic EL element was formed. The resulting one was superimposed on the aforesaid cathode to be brought into close contact with the aforesaid transparent support substrate, and curing and sealing were carried out via exposure of UV rays onto the glass substrate side, whereby the lighting device shown in FIG. 5 and FIG. 6 was formed.

The resistance value of the light emitting layer, the change of half bandwidth of the emission spectrum, and the chromaticity of the organic EL element were measured using an impedance spectroscopy apparatus.

(1) Rate of Change in Resistance Before and after Driving Organic EL Element

By referring to the description in pp. 423 to 425 of "Handbook of Thin film evaluation" published by Techno System, Co. Ltd, and by using a 1260 type impedance analyzer with a 1296 type dielectric interface (made by Solartronanalytical Co.), the resistance value of the light emitting layer of the prepared organic EL element at a bias voltage of 1 V was measured.

Each organic EL element was driven with a constant electric current of 2.5 mA/cm$^2$ at room temperature (about 23° C. to 25° C.) for 1,000 hours. The resistance values of the light emitting layer of each Organic EL element were measured at the moment of before and after driving. The rate of change in resistance was obtained according to the following calculating formula. In Table 2, the results were described as a relative value when the rate of change in resistance for Organic EL element 1-1 was set to be 100.

Rate of change in resistance before and after driving=[(Resistance after driving/Resistance before driving)−1]×100

The case showing nearer to zero indicates that the rate of change of before and after driving is smaller.

(2) Rate of Change in Half Bandwidth of Emission Spectrum Before and after Driving Organic EL Element Each organic EL element was driven with a constant electric current of 2.5 mA/cm$^2$ at room temperature (about 23° C. to 25° C.) for 1,000 hours. The emission spectra of initial and after driving were measured using CS-1000

(made by Konica Minolta Optics, Inc.). The rate of change in half bandwidth was obtained according to the following calculating formula. In Table 2, the results were described as a relative value when the rate of change in half bandwidth for Organic EL element 1-1 was set to be 100.

Rate of change in half bandwidth before and after driving=[(Half bandwidth after driving/Half bandwidth of initial driving)−1]×100

The case showing nearer to zero indicates t that the rate of change of before and after driving is smaller.

(3) Chromaticity of Organic EL Element

By using a spectroradiometric luminance meter CS-1000 (made by Konica Minolta Optics, Inc.), the chromaticity (x and y) of an organic EL element was measured with 2-degree viewing angle front luminance. The y value was taken as an indicator. When the y value is low, the purity of the blue emission is excellent.

[Example 2] (Coating System)

<<Preparation of Organic EL Element 2-1>>

An anode was prepared by making patterning to a glass substrate of 100 mm×100 mm×1.1 mm (NA45, produced by NH Techno Glass Corp.) on which ITO (indium tin oxide) was formed with a thickness of 100 nm. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

On the transparent support substrate thus prepared was applied a 70% solution of poly(3,4-ethylenedioxythiphene)-polystyrene sulfonate (PEDOT/PSS, Baytron P AI4083, made by Bayer AG.) diluted with water by using a spin coating method at 3,000 rpm for 30 seconds to form a film

TABLE 2

| Organic EL element No. | Host compound | Light emitting dopant | Rate of change in Resistance (Relative value) | Rate of change in Half bandwidth (Relative value) | Chromaticity (y value) | Remarks |
|---|---|---|---|---|---|---|
| 1-1 | Comparative compound A | Implement DP | 100 | 100 | 0.46 | *1 |
| 1-2 | Comparative compound B | Implement DP | 89 | 82 | 0.52 | *1 |
| 1-3 | Comparative compound C | Implement DP | 116 | 56 | 0.32 | *1 |
| 1-4 | Comparative compound D | Implement DP | 120 | 206 | 0.47 | *1 |
| 1-5 | SH-1 | Implement DP | 6 | 33 | 0.33 | *2 |
| 1-6 | SH-3 | Implement DP | 10 | 40 | 0.36 | *2 |
| 1-7 | SH-12 | Implement DP | 7 | 31 | 0.34 | *2 |
| 1-8 | SH-15 | Implement DP | 15 | 39 | 0.37 | *2 |
| 1-9 | SH-16 | Implement DP | 8 | 35 | 0.35 | *2 |
| 1-10 | SH-17 | Implement DP | 5 | 29 | 0.31 | *2 |
| 1-11 | SH-22 | Implement DP | 11 | 48 | 0.38 | *2 |
| 1-12 | SH-23 | Implement DP | 12 | 45 | 0.35 | *2 |
| 1-13 | SH-26 | Implement DP | 14 | 44 | 0.37 | *2 |
| 1-14 | SH-27 | Implement DP | 7 | 34 | 0.34 | *2 |
| 1-15 | SH-28 | Implement DP | 15 | 35 | 0.33 | *2 |
| 1-16 | SH-29 | Implement DP | 13 | 30 | 0.38 | *2 |
| 1-17 | SH-34 | Implement DP | 9 | 32 | 0.35 | *2 |
| 1-18 | SH-35 | Implement DP | 16 | 39 | 0.33 | *2 |
| 1-19 | SH-38 | Implement DP | 15 | 40 | 0.34 | *2 |
| 1-20 | SH-40 | Implement DP | 17 | 42 | 0.36 | *2 |
| 1-21 | SH-43 | Implement DP | 7 | 33 | 0.35 | *2 |
| 1-22 | SH-50 | Implement DP | 20 | 43 | 0.33 | *2 |
| 1-23 | SH-1 | Implement D-53 | 8 | 35 | 0.31 | *2 |
| 1-24 | SH-12 | Implement D-53 | 9 | 33 | 0.31 | *2 |
| 1-25 | SH-17 | Implement D-53 | 7 | 31 | 0.29 | *2 |
| 1-26 | SH-19 | Implement D-53 | 15 | 34 | 0.37 | *2 |
| 1-27 | SH-22 | Implement D-53 | 12 | 49 | 0.35 | *2 |
| 1-28 | SH-52 | Implement D-53 | 17 | 36 | 0.32 | *2 |
| 1-29 | SH-67 | Implement DP | 14 | 42 | 0.35 | *2 |
| 1-30 | SH-69 | Implement DP | 18 | 40 | 0.36 | *2 |

*1: Comparative example
*2: Inventive example

From the results in Table 2, it was shown that Organic EL elements 1-5 to 1-30 of the present invention exhibited a small rate of change in resistance of the light emitting layer and in half bandwidth of emission spectrum. Thus, it has been achieved to obtain an organic EL element having a small change of physical properties in the light emitting layer. Further, the comparative organic EL elements 1-1, 1-2 and 1-4 each exhibited a high y value and the color purity was inferior, while Organic EL elements 1-5 to 1-30 of the present invention were found to be excellent in chromaticity (color purity).

and then it was dried at 200° C. for one hour. A first hole transport layer having a thickness of 20 nm was prepared.

The aforesaid substrate was transferred in a nitrogen atmosphere, a solution containing 50 mg of ADS254BE (made by American Dye Source, Inc.) dissolved in 10 ml of monochlorobenzene was applied on the aforesaid first hole transport layer by using a spin coating method at 2,500 rpm for 30 seconds to form a film. The film was further dried under vacuum at 130° C. for one hour. Thus, a second hole hole transport layer was formed.

Onto the aforesaid second hole transport layer was applied a solution containing 100 mg of Comparative compound A and 13 mg of Implement DP dissolved in 10 ml of butyl acetate by using a spin coating method at 1,000 rpm for 30 seconds to form a film. The film was further dried under vacuum at 60° C. for one hour. Thus, a light emitting layer having a thickness of 45 nm was formed.

Subsequently, onto the aforesaid light emitting layer was applied a solution containing 50 mg of BCP dissolved in 10 ml of hexafluoro isopropanol (HFIP) by using a spin coating method at 1,000 rpm for 30 seconds to form a film. The film was further dried under vacuum at 60° C. for one hour. Thus, an electron transport layer having a thickness of 25 nm was formed.

Subsequently, the aforesaid substrate was fixed to a substrate holder of a vacuum deposition apparatus. After reducing the pressure of a vacuum tank to $4 \times 10^{-4}$ Pa, 0.4 nm thick potassium fluoride was vapor deposited as a cathode buffer layer, and then, 110 nm thick aluminum was vapor deposited to form a cathode, whereby Organic EL element 2-1 was prepared.

<<Preparation of Organic EL Elements 2-2 to 2-20>>

Organic EL elements 2-2 to 2-20 were prepared in the same manner as preparation of Organic EL element 2-1 except that the light emitting dopant and the host compound were changed with the compounds described in Table 3.

<<Evaluation of Organic EL Elements 2-1 to 2-20>>

When the prepared organic EL elements were evaluated, they were sealed in the same manner as Organic EL element 1 in Example 1. The lighting device was formed as illustrated in FIG. 5 and FIG. 6 and it was evaluated.

Each sample thus prepared was subjected to evaluations for the rate of change in resistance of the light emitting layer, the rate of change in half bandwidth of emission spectrum and chromaticity as performed in Example 1. The evaluation results are shown in Table 3.

Thus, it has been achieved to obtain an organic EL element having a small change of physical properties in the light emitting layer. Further, the comparative organic EL elements 2-1, 2-2, 2-3 and 2-4 each exhibited a high y value and the color purity was inferior, while Organic EL elements 2-5 to 2-20 of the present invention were found to be excellent in chromaticity (color purity).

[Example 2] (White System)

<<Preparation of Organic EL Element 3-1>>

An anode was prepared by making patterning to a glass substrate of 100 mm×100 mm×1.1 mm (NA45, produced by NH Techno Glass Corp.) on which ITO (indium tin oxide) was formed with a thickness of 100 nm. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

The resulting transparent support substrate was fixed to a substrate holder of a commercial vacuum deposition apparatus. Separately, 200 mg of TPD was placed in a molybdenum resistance heating boat, 200 mg of Comparative compound A was placed in another molybdenum resistance heating boat, 200 mg of Implement DP was placed in another molybdenum resistance heating boat, 200 mg of Implement D-15 was placed in another molybdenum resistance heating boat, 200 mg of Implement D-6 was placed in another molybdenum resistance heating boat, and 200 mg of BCP was placed in another molybdenum resistance heating boat. The resulting boats were fitted in the vacuum deposition apparatus.

TABLE 3

| Organic EL element No. | Host compound | Light emitting dopant | Rate of change in Resistance (Relative value) | Rate of change in Half bandwidth (Relative value) | Chromaticity (y value) | Remarks |
| --- | --- | --- | --- | --- | --- | --- |
| 2-1 | Comparative compound A | Implement DP | 100 | 100 | 0.47 | *1 |
| 2-2 | Comparative compound B | Implement DP | 92 | 85 | 0.55 | *1 |
| 2-3 | Comparative compound C | Implement DP | 121 | 57 | 0.36 | *1 |
| 2-4 | Comparative compound D | Implement DP | 123 | 204 | 0.49 | *1 |
| 2-5 | SH-1 | Implement DP | 9 | 34 | 0.34 | *2 |
| 2-6 | SH-3 | Implement DP | 12 | 41 | 0.36 | *2 |
| 2-7 | SH-5 | Implement DP | 12 | 40 | 0.38 | *2 |
| 2-8 | SH-8 | Implement DP | 8 | 35 | 0.38 | *2 |
| 2-9 | SH-11 | Implement DP | 9 | 39 | 0.40 | *2 |
| 2-10 | SH-12 | Implement DP | 7 | 35 | 0.35 | *2 |
| 2-11 | SH-15 | Implement DP | 16 | 38 | 0.36 | *2 |
| 2-12 | SH-17 | Implement DP | 9 | 33 | 0.34 | *2 |
| 2-13 | SH-19 | Implement DP | 17 | 41 | 0.36 | *2 |
| 2-14 | SH-20 | Implement DP | 13 | 37 | 0.39 | *2 |
| 2-15 | SH-30 | Implement DP | 18 | 42 | 0.41 | *2 |
| 2-16 | SH-31 | Implement DP | 11 | 39 | 0.39 | *2 |
| 2-17 | SH-45 | Implement DP | 16 | 42 | 0.42 | *2 |
| 2-18 | SH-49 | Implement DP | 14 | 39 | 0.39 | *2 |
| 2-19 | SH-55 | Implement DP | 12 | 40 | 0.38 | *2 |
| 2-20 | SH-66 | Implement DP | 14 | 44 | 0.37 | *2 |

*1: Comparative example
*2: Inventive example

From the results in Table 3, it was shown that Organic EL elements 2-5 to 2-20 of the present invention exhibited a small rate of change in resistance of the light emitting layer and in half bandwidth of emission spectrum in contrast with Comparative organic EL elements 2-1, 2-2, 2-3 and 2-4.

Subsequently, after reducing the pressure of a vacuum tank to $4 \times 10^{-4}$ Pa, the aforesaid heating boat containing TPD was heated via application of electric current and deposition was made onto the aforesaid transparent support substrate at a deposition rate of 0.1 nm/second, whereby it was produced a hole transport layer having a thickness of 10 nm.

Further, the aforesaid heating boats each respectively containing Comparative compound A, Implement DP, Implement D-15 and Implement D-6 were heated via application of electric current and co-deposition was carried out onto the aforesaid hole transport layer at a respective deposition rate of 0.1 nm/second, 0.025 nm/second, 0.0007 nm/second, and 0.0002 nm/second, whereby it was produced a light emitting layer having a thickness of 60 nm.

Further, the aforesaid heating boat containing BCP was heated via application of electric current and deposition was carried out onto the aforesaid light emitting layer at a deposition rate of 0.1 nm/second, whereby it was produced an electron transport layer having a thickness of 320 nm.

Subsequently, 0.5 nm thick potassium fluoride was vapor deposited as a cathode buffer layer, and then, 110 nm thick aluminum was vapor deposited to form a cathode, whereby Organic EL element 3-1 was prepared.

An electric current was applied to the prepared Organic EL element 3-1 to result in producing white light. It was revealed that this element was applicable to a lighting device. In addition, it was found out that white light emission was obtained with organic EL elements by using other exemplary compounds of the present invention.

<<Preparation of Organic EL Elements 3-2 to 3-15>>

Organic EL elements 3-2 to 3-15 were prepared in the same manner as preparation of Organic EL element 3-1 except that the host compound was changed with the compounds described in Table 4.

<<Evaluation of Organic EL Elements 3-1 to 3-15>>

The rate of change in resistance of the light emitting layer was measured in the same manner as in Example 1. It was confirmed that the Organic EL elements of the present invention showed the rate of change of less than half of the comparative organic EL elements.

(Measurement of Chromaticity)

Further, the emission color of the Organic EL elements 3-1 to 3-15 was measured with a spectroradiometric luminance meter CS-1000 (produced by Konica Minolta Optics, Inc.). The 2-degree viewing angle front luminance was measured, and it was found that chromaticity in the CIE 1931 Color Specification System at 1,000 cd/m$^2$ was within the region of x=0.33±0 0.07 and y=0.33±0.1. It was confirmed that the emission light was white color.

TABLE 4

| Organic EL element No. | Host compound | Rate of change in Half bandwidth (Relative value) | Remarks |
| --- | --- | --- | --- |
| 3-1 | Comparative compound A | 100 | Comparative example |
| 3-2 | Comparative compound B | 95 | Comparative example |
| 3-3 | Comparative compound C | 144 | Comparative example |
| 3-4 | SH-1 | 18 | Inventive example |
| 3-5 | SH-12 | 21 | Inventive example |
| 3-6 | SH-16 | 24 | Inventive example |
| 3-7 | SH-17 | 15 | Inventive example |
| 3-8 | SH-19 | 30 | Inventive example |
| 3-9 | SH-22 | 11 | Inventive example |
| 3-10 | SH-36 | 42 | Inventive example |
| 3-11 | SH-37 | 43 | Inventive example |
| 3-12 | SH-42 | 40 | Inventive example |
| 3-13 | SH-52 | 34 | Inventive example |
| 3-14 | SH-65 | 38 | Inventive example |
| 3-15 | SH-71 | 36 | Inventive example |

As shown by the results in Table 4, Organic EL elements 3-4 to 3-15 of the present invention were found to have a small rate of change in resistance of the light emitting layer compared with comparative organic EL elements 3-1 to 3-3. Thus, it has been achieved to obtain organic EL elements having a small change in physical property of the thin film in the light emitting layer.

[Example 4] (Color)

<<Preparation of Organic EL Element 4-1>>
(Preparation of Blue Light Emitting Element)

Organic EL element 1-5 in Example 1 was used as a blue light emitting element.

(Preparation of Green Light Emitting Element)

A green light emitting element was prepared in the same manner as preparation of Organic EL element 1-5 in Example 1 except that the compound of Implement DP was replaced with the compound of Implement D-15. The prepared element was used as a green light emitting element (Preparation of Red Light Emitting Element)

A red light emitting element was prepared in the same manner as preparation of Organic EL element 1-5 in Example 1 except that the compound of Implement DP was replaced with the compound of Implement D-6. The prepared element was used as a red light emitting element The red, green and blue light emitting elements prepared above were placed side by side on the same substrate to produce a full color active matrix display device having a structure as illustrated in FIG. 1. FIG. 2 is a schematic drawing of only a display section A of the aforesaid produced display device.

That is, a wiring section containing plural scanning line 5 and data lines 6, and plural pixels 3 (such as a pixel having an emission color of a red region, a pixel of a green region and a pixel of a blue region) arranged in parallel are provided on the same substrate. The scanning lines 5 and data lines 6 in a wiring section, which are respectively composed of a conductive material, cross each other at a right angle in a grid form and are connected to the pixels 3 at the right-angled crossing points (details are not shown in the drawing).

The aforesaid plural pixels 3 each are operated in an active matrix mode, in which an organic EL element, a switching transistor and an operating transistor are provided corresponding to each emission color, and receive an image data signal from the date line 6 when a scanning signal is applied from the scanning line 5 to emit based on the received image data. Each red, green and blue pixel was suitably arranged in parallel in this manner, whereby a full-color display device was prepared. It was found that the produced organic EL element exhibited emission colors of red, green and blue by applying voltage to the electrode and can be used as a full color display device.

As described above, the present invention can provide an organic electroluminescent element achieving a small resistance change of the light emitting layer when applying current over time. As a side effect of this property, the present invention can provide an organic electroluminescent element excellent in chromaticity of the light emission spectrum with exhibiting a small change of light emission properties over time. The present invention can provide a lighting device and a display device provided with that organic electroluminescent element. Further, the present invention can produce an organic electroluminescent element having the aforesaid properties with a wet process.

INDUSTRIAL APPLICABILITY

It can provide an organic electroluminescent element achieving a small resistance change of the light emitting layer when applying current over time by the present invention. As a side effect of this property, it can provide an organic electroluminescent element excellent in chromaticity of the light emission spectrum with exhibiting a small change of light emission properties over time. It can also provide a lighting device and a display device provided with that organic electroluminescent element.

DESCRIPTION OF SYMBOLS

1: Display
3: Pixel
5: Scanning line
6: Data line
7: Electric source line
10: Organic EL element
11: Switching transistor
12: Operating transistor
13: Capacitor
101: Organic EL element
102: Glass cover
105: Cathode
106: Organic EL layer
107: Glass substrate having a transparent electrode
108: Nitrogen gas
109: Water catching agent
201: Glass substrate
202: ITO transparent electrode
203: Dividing wall
204: Hole injection layer
205B, 205G and 205R: Light emitting layer
206: Cathode
A: display section
B: control diction
L: Light

The invention claimed is:
1. An organic electroluminescent element comprising a pair of electrodes having therebetween one or a plurality of organic layers,
wherein one or more of the organic layers contain a compound having a structure represented by Formula (1),

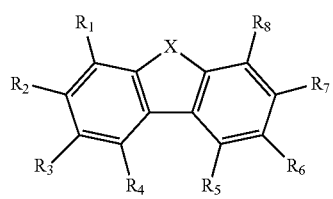

Formula (1)

in Formula (1),
X represents O, S or $NR_9$;
$R_1$ to $R_8$ each represent: a hydrogen atom, a deuterium atom, a halogen atom, a cyano group, an alkyl group, an alkenyl group, an alkynyl group, an alkoxy group, a carbonyl group, an amino group, a silyl group, a phosphine oxide group, an aromatic hydrocarbon ring group, an aromatic heterocyclic group, a non-aromatic hydrocarbon ring group, a non-aromatic heterocyclic group, or a substituent represented by Formula (2);
at least one of $R_1$ to $R_8$ contains an aromatic heterocyclic group having 14 or more π electrons, and at least one of $R_1$ to $R_8$ is represented by Formula (2), provided that $R_1$ to $R_8$ may be further substituted with a substituent, and $R_1$ to $R_8$ may be the same or different; and
$R_9$ represents: a hydrogen atom, a deuterium atom, an alkyl group, an alkenyl group, an alkynyl group, an arylalkyl group, an aromatic hydrocarbon ring group, an aromatic heterocyclic group, a non-aromatic hydrocarbon ring group, or a non-aromatic heterocyclic group,

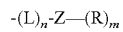 Formula (2)

in Formula (2),
L represents a linking group selected from the group consisting of an alkylene group, an alkenylene group, a m-phenylene group and a single ring aromatic heterocyclic group, the linking group may be substituted with a substituent;
Z represents C, Si, Ge, or P;
R represents an alkyl group, or an aromatic hydrocarbon ring group each having a total carbon atom number of 1 to 20, provided that R may be further substituted with a substituent;
"n" represents an integer of 2 to 8;
"m" represents an integer of 2 to 3;
when the compound contains a plurality of groups represented by Formula (2), a plurality of Ls, Zs an Rs each may be the same or different with each other, provided that adjacent Ls and adjacent Rs are not joined to form a ring.
2. The organic electroluminescent element described in claim 1, wherein L in Formula (2) represents the m-phenylene group.
3. The organic electroluminescent element described in claim 1, wherein Z in Formula (2) represents Si.
4. The organic electroluminescent element described in claim 1, wherein the compound represented by Formula (1) is a compound represented by Formula (3),

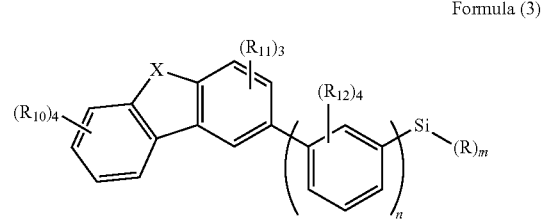

Formula (3)

in Formula (3),
R, n, m and X each are synonymous with R, n, m and X in Formula (1) or Formula (2);
$R_{10}$, $R_{11}$ and $R_{12}$ each represent: a hydrogen atom, a deuterium atom, a halogen atom, a cyano group, an alkyl group, an alkenyl group, an alkynyl group, an alkoxy group, a carbonyl group, an amino group, a silyl group, a phosphine oxide group, an aromatic hydrocarbon ring group, an aromatic heterocyclic group, a non-aromatic hydrocarbon ring group, or a non-aromatic heterocyclic group, provided that $R_{10}$, $R_{11}$, and $R_{12}$ may be further substituted with a substituent, $R_{10}$, $R_{11}$, and $R_{12}$ may be the same or different, and at least one of $R_{10}$ and $R_{11}$ is an aromatic heterocyclic group having 14 or more π electrons.

5. The organic electroluminescent element described in claim 1, wherein the compound having a structure represented by Formula (1) is a compound represented by Formula (4) or Formula (5), Formula (4)

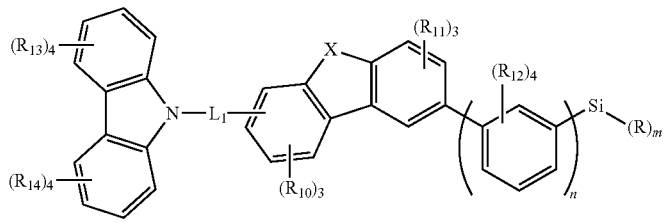

Formula (5)

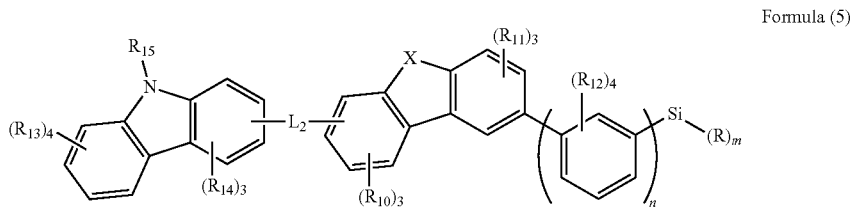

in Formula (4) and Formula (5),

R, n, m and X each are synonymous with R, n, m and X in Formula (1) or Formula (2);

$R_{10}$ to $R_{14}$ each represent: a hydrogen atom, a deuterium atom, a halogen atom, a cyano group, an alkyl group, an alkenyl group, an alkynyl group, an alkoxy group, a carbonyl group, an amino group, a silyl group, a phosphine oxide group, an aromatic hydrocarbon ring group, an aromatic heterocyclic group, a non-aromatic hydrocarbon ring group, or a non-aromatic heterocyclic group, provided that $R_{10}$ to $R_{14}$ may be further substituted with a substituent, and $R_{10}$ to $R_{14}$ may be the same or different;

$R_{15}$ represent: a hydrogen atom, a deuterium atom, an alkyl group, an alkenyl group, an alkynyl group, an arylalkyl group, an aromatic hydrocarbon ring group, an aromatic heterocyclic group, a non-aromatic hydrocarbon ring group, or a non-aromatic heterocyclic group; and $L_1$ and $L_2$ each represent a single bond or a divalent linking group.

6. The organic electroluminescent element described in claim 1, wherein the compound having a structure represented by Formula (1) is a compound represented by Formula (6), Formula (6)

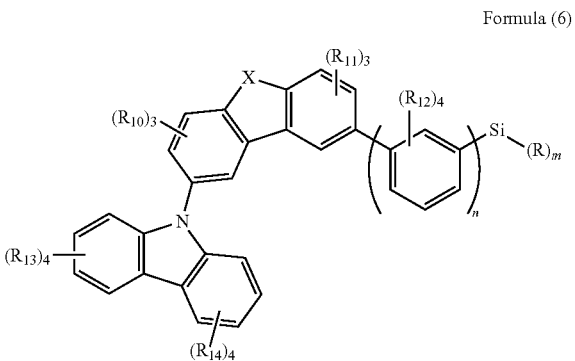

in Formula (6),

R, n, m and X each are synonymous with R, n, m and X in Formula (1) or Formula (2);

$R_{10}$ to $R_{14}$ each represent: a hydrogen atom, a deuterium atom, a halogen atom, a cyano group, an alkyl group, an alkenyl group, an alkynyl group, an alkoxy group, a carbonyl group, an amino group, a silyl group, a phosphine oxide group, an aromatic hydrocarbon ring group, an aromatic heterocyclic group, a non-aromatic hydrocarbon ring group, or a non-aromatic heterocyclic group, provided that $R_{10}$ to $R_{14}$ may be further substituted with a substituent, and $R_{10}$ to $R_{14}$ may be the same or different.

7. The organic electroluminescent element described in claim 1, wherein one of the organic layers is a light emitting layer, and the light emitting layer contains the aforesaid compound as a host compound for organic electroluminescence.

8. The organic electroluminescent element described in claim 7, wherein the aforesaid light emitting layer contains an iridium complex or a platinum complex, and the complex emits phosphorescence by applying current.

9. The organic electroluminescent element described in claim 1, emitting white light.

10. A lighting device provided with the organic electroluminescent element described in claim 1.

11. A display device provided with the organic electroluminescent element described in claim 1.

* * * * *